US00RE48651E

(19) United States
(12) Reissued Patent
Chen et al.

(10) Patent Number: US RE48,651 E
(45) Date of Reissued Patent: Jul. 20, 2021

(54) PRODUCTION CELL LINE ENHANCERS

(71) Applicant: Regeneron Pharmaceuticals, Inc., Tarrytown, NY (US)

(72) Inventors: Gang Chen, Yorktown Heights, NY (US); Darya Burakov, Yonkers, NY (US); Dipali Deshpande, White Plains, NY (US)

(73) Assignee: REGENERON PHARMACEUTICALS, INC., Tarrytown, NY (US)

(21) Appl. No.: 16/387,134

(22) Filed: Apr. 17, 2019

Related U.S. Patent Documents

Reissue of:
(64) Patent No.: 9,688,751
Issued: Jun. 27, 2017
Appl. No.: 15/201,104
Filed: Jul. 1, 2016

U.S. Applications:
(60) Division of application No. 14/555,220, filed on Nov. 26, 2014, now Pat. No. 9,382,315, which is a division of application No. 13/904,587, filed on May 29, 2013, now Pat. No. 9,079,954, which is a continuation-in-part of application No. PCT/US2013/043116, filed on May 29, 2013.

(60) Provisional application No. 61/652,549, filed on May 29, 2012.

(51) Int. Cl.

| | |
|---|---|
| ***C07K 16/22*** | (2006.01) |
| ***C12N 15/85*** | (2006.01) |
| ***C07K 14/47*** | (2006.01) |
| ***C12N 15/79*** | (2006.01) |
| ***C07K 16/00*** | (2006.01) |
| ***C12N 9/24*** | (2006.01) |
| ***C12N 15/09*** | (2006.01) |
| ***C12N 15/63*** | (2006.01) |

(52) U.S. Cl.
CPC ..... *C12N 15/09* (2013.01); *C07K 14/47* (2013.01); *C07K 14/4705* (2013.01); *C07K 16/00* (2013.01); *C07K 16/22* (2013.01); *C12N 9/2488* (2013.01); *C12N 15/79* (2013.01); *C12N 15/85* (2013.01); *C12Y 302/01* (2013.01); *C07K 2317/14* (2013.01); *C07K 2317/51* (2013.01); *C07K 2317/515* (2013.01); *C12N 15/63* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 7,479,379 | B2 | 1/2009 | Rycyzyn et al. |
| 7,514,237 | B2 | 4/2009 | Gao et al. |
| 9,079,954 | B2 | 7/2015 | Chen et al. |
| 9,193,786 | B2 | 11/2015 | Chen et al. |
| 9,228,012 | B2 | 1/2016 | Chen et al. |
| 9,382,315 | B2 | 7/2016 | Chen et al. |
| 9,476,081 | B2 | 10/2016 | Cain et al. |
| 9,688,751 | B2 | 6/2017 | Chen et al. |
| 9,950,047 | B2 | 4/2018 | Kawaoka et al. |
| 10,227,401 | B2 | 3/2019 | Chen et al. |
| 2004/0170622 | A1 | 9/2004 | Glimcher et al. |
| 2005/0106222 | A1 | 5/2005 | Ailor et al. |
| 2010/0144013 | A1 | 6/2010 | Goedegebuur et al. |
| 2011/0027286 | A1 | 2/2011 | Thurston et al. |
| 2011/0142799 | A1 | 6/2011 | Glimcher et al. |
| 2011/0159015 | A1 | 6/2011 | Sleeman et al. |
| 2011/0293630 | A1 | 12/2011 | Stitt et al. |
| 2013/0323788 | A1 | 12/2013 | Chen et al. |
| 2015/0175688 | A1 | 6/2015 | Chen et al. |
| 2015/0299309 | A1 | 10/2015 | Chen et al. |
| 2015/0299310 | A1 | 10/2015 | Chen et al. |
| 2015/0353634 | A1 | 12/2015 | Chen et al. |
| 2017/0291938 | A1 | 10/2017 | Chen et al. |

FOREIGN PATENT DOCUMENTS

| | | | |
|---|---|---|---|
| CN | 101426812 | A | 5/2009 |
| JP | 2007-537728 | A | 12/2007 |
| JP | 2008-507531 | A | 3/2008 |
| JP | 2008-513465 | A | 5/2008 |
| JP | 2011-504096 | A | 2/2011 |
| JP | 2012-504943 | A | 3/2012 |
| WO | 2004/111194 | A2 | 12/2004 |

(Continued)

OTHER PUBLICATIONS

Becker E. et al., "Evaluation of a Combinatorial Cell Engineering Approach to Overcome Apoptotic Effects in XBP-1(s) Expressing Cells", Journal of Biotechnology, doi:10.1016/j.jpiotec.2009.11.018 (2008).

Becker E. et al., "A XBP-1 Dependent Bottle-Neck in Production of IgG Subtype Antibodies in Chemically Defined Serum-Free Chinese Hamster Ovary (CHO) Fed-Batch Processes", Journal of Biotechnology, doi:10.1016/j.biotec.2008.03.008 (2007).

Byun H-M et al., "Plasmid Vectors Harboring Cellular Promoters Can Induce Prolonged Gene Expression in Hematopoietic and Mesenchymal Progenitor Cells", Biochemical and Biophysical Research Communications 332:518-523 (2005).

(Continued)

*Primary Examiner* — Celine X Qian
(74) *Attorney, Agent, or Firm* — Scully, Scott, Murphy & Presser, P.C.; Todd R. Samelman

(57) ABSTRACT

The present invention relates to discovery of the ectopic expression of EDEM2 in a production cell to improve the yield of a useful multi-subunit protein. Thus, the present invention provides for production cell lines, such as the canonical mammalian biopharmaceutical production cell—the CHO cell, containing recombinant polynucleotides encoding EDEM2. Also disclosed is a production cell containing both an EDEM2-encoding polynucleotide as well an XBP1-encoding polynucleotide. Improved titers of antibodies produced by these cell lines are disclosed, as well as the improved cell densities attained by these cells in culture.

38 Claims, 3 Drawing Sheets

Specification includes a Sequence Listing.

(56) References Cited

FOREIGN PATENT DOCUMENTS

| | | | |
|---|---|---|---|
| WO | 2005/094355 | A2 | 10/2005 |
| WO | 2006/014678 | A2 | 2/2006 |
| WO | 2006/031931 | A2 | 3/2006 |
| WO | 2009/058346 | A1 | 5/2009 |
| WO | 2009/062789 | A1 | 5/2009 |
| WO | 2009/155008 | A1 | 12/2009 |
| WO | 2010/040508 | A1 | 4/2010 |
| WO | 2011079257 | A2 | 6/2011 |
| WO | 2011150008 | A1 | 12/2011 |

OTHER PUBLICATIONS

Gain K. et al., "A CHO Cell Line Engineered to Express XBP1 and ERO1-Lα Has Increased Levels of Transient Protein Expression", Biotechnol. Prog. 29(3):697-706 (May-Jun. 2013).
Eriksson K.K. et al., "EDEM Contributes to Maintenance of Protein Folding Efficiency and Secretary Capacity", The Journal of Biological Chemistry 279(43):44600-44605 (Oct. 22, 2004).
Gulis G. et al., "Optimization of Heterologous Protein Production in Chinese Hamster Ovary Cells Under Overexpression of Spliced Form of Human X-Box Binding Protein", BMC Biotechnology 14:26 (2014).
Hansen J. et al., "A Large-Scale, Gene-Driven Mutagenesis Approach for the Functional Analysis of the Mouse Genome", PNAS 100(17):9918-9922 (Aug. 19, 2003).
Ma Y. et al., "The Stressful Road to Antibody Secretion", Nature 4(4):310-311 (Apr. 2003).
Mast S.W. et al., "Human EDEM2, a Novel Homolog of Family 47 Glycosidases, is Involved in ER-Associated Degradation of Glycoproteins", Glycobiology 15(4):421-436 (2005).
Olivari S. et al., "A Novel Stress-Induced EDEM Variant Regulating Endoplasmic Reticulum-Associated Glycoprotein Degradation", The Journal of Biological Chemistry 280(4):2424-2428 (Jan. 28, 2005).
Olivari S. et al., "Glycoprotein Folding and the Role of EDEM1, EDEM2 and EDEM3 in Degradation of Folding-Defective Glycoproteins", FEBS Letters 581:3658-3664 (2007).
Schorpp M. et al., "The Human Ubiquitin C Promoter Directs High Ubiquitous Expression of Transgenes in Mice", Nucleic Acids Research 24(9):1787-1788 (1996).
Strausberg RL et al., "Generation and Initial Analysis of More than 15,000 Full-Length Human and Mouse cDNA Sequences", PNAS 99(26):16899-16903 (Dec. 24, 2002).
Vembar S.S. et al., "One Step at a Time: Endoplasmic Reticulum-Associated Degradation", Nature Reviews Molecular Cell Biology 9:944-957 (Dec. 2008).
Yoshida H. et al., "A Time-Dependent Phase Shift in the Mammalian Unfolded Protein Response", Developmental Cell 4:265-271 (Feb. 2003).
NCBI GenBank Accession No. NM_145537.2 (Feb. 15, 2015).
Canadian Office Action dated Jun. 29, 2018 received in Canadian Patent Application No. 2,873,131.
Japanese Notice of Reasons for Rejection dated Mar. 20, 2019 received in Japanese Patent Application No. 2018-030324, together with an English-language translation.
Gunn K.E. et al., "A Role for the Unfolded Protein Response in Optimizing Antibody Secretion", Molecular Immunology 41:919-927 (2004).
Iwakoshi N.N. et al., "Plasma Cell Differentiation and the Unfolded Protein Response Intersect at the Transcription Factor XBP-1", Nature Immunology 4(4):321-329 (Apr. 2003).
Tirosh B. et al., "XBP-1 Specifically Promotes IgM Synthesis and Secretion, But is Dispensable for Degradation of Glycoproteins in Primary B Cells", JEM 202(4):505-516 (Apr. 15, 2005).
Australian Examination Report dated Jul. 17, 2020 received in Australian Application No. 2019203780.
Tigges M. et al., "Xbp1-Based Engineering of Secretory Capacity Enhances the Productivity of Chinese Hamster Ovary Cells", Metabolic Engineering 8:264-272 (2006).
Japanese Notice of Reasons for Rejection dated Jan. 25, 2021 received in Japanese Patent Application No. 2019-210124, together with an English-language translation.
Byun et al., Biochem. Biophys. Res. Comm. Jul. 1, 2005; 332(2): 518-23.
Schorpp et al., Nucleic Acids Research, 1996, vol. 24, No. 9, pp. 1787-1788.
Strausberg, RL, et al., 2002, "Generation and initial analysis of more than 15,000 full-length human and mouse cDNA sequences", Proc Nail Acad Sci U.S.A. 99(26): 16899-903. Epub Dec. 1, 2002.
Vembar, S.S. and Brodsky, J.L. 2008, "One step at a time: endoplasmic reticulum-associated degradation", Nature Rev Mol Cell Bio 9(12): 944-957. Published online Nov. 12, 2008.
Yoshida, H. et al., 2006, "XBP1 is critical to protect cells from endoplasmic reticulum stress: evidence from Site-2 protease-deficient Chinese hamster ovary cells", Cell Structure and Function 31(2): 117-125. Epub Nov. 17, 2006.
Ma, Y. and Hendershot, L.M. 2003, "The stressful road to antibody secretion." Nature 4(4):310-311.
Slominska-Wojewodzka M, The role of EDEM2 compared with EDEM1 in ricin transport from the endoplasmic reticulum to the cytosol, NCBI GenBank Accession ID:NM_145537.2, Feb. 15, 2015.

Titer distribution for clones from RGC91 and RGC92

ICD distribution for clones from RGC91 and RGC92

Fig. 2A Clone stability of XBP1-expressing cells
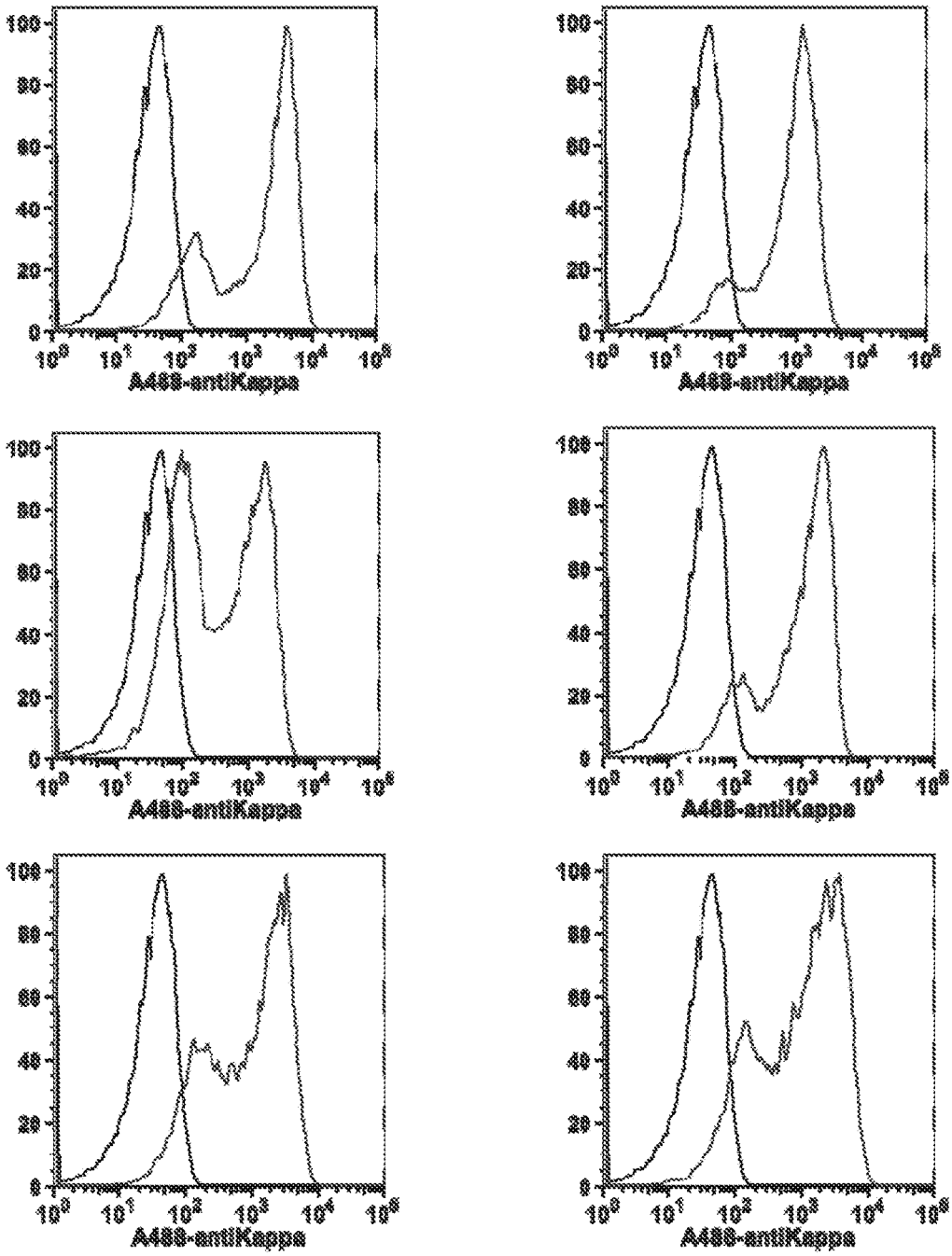

Fig. 2B Clone stability of EDEM2-expressing cells
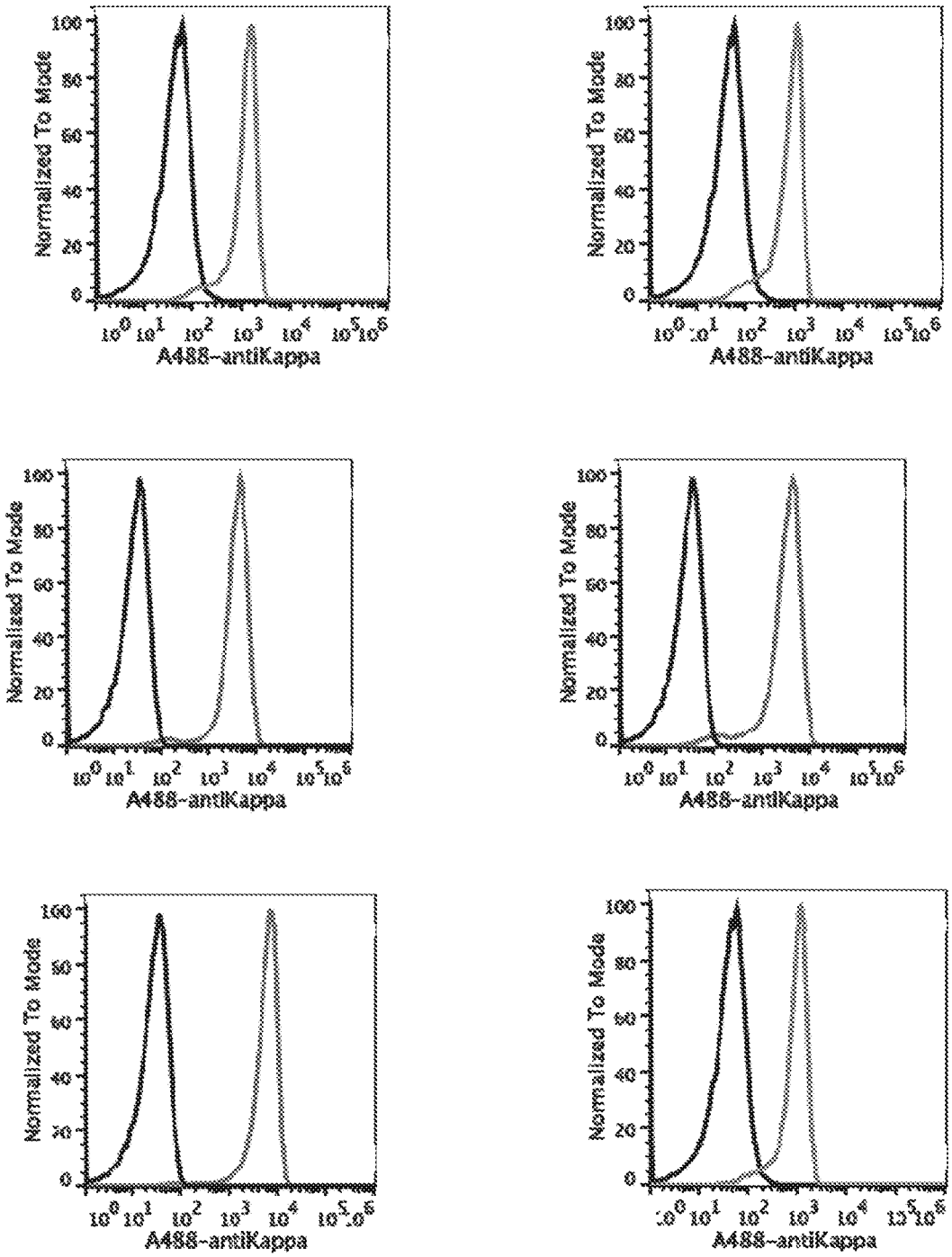

PRODUCTION CELL LINE ENHANCERS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is *a reissue application of U.S. Pat. No. 9,688,751 B2, which issued on Jun. 27, 2017 having U.S. Ser. No. 15/201,104, which is a* divisional of U.S. patent application Ser. No. 14/555,220 filed 26 Nov. 2014, *now U.S. Pat. No. 9,382,315,* which is divisional of U.S. patent application Ser. No. 13/904,587 filed 29 May 2013, now U.S. Pat. No. 9,079,954, and which is a continuation-in-part of PCT International Application No. PCT/US2013/043116, filed 29 May 2013, which claims the benefit of U.S. patent application Ser. No. 13/904,587, filed 29 May 2013, and claims the benefit under 35 U.S.C. §119(e) of U.S. Provisional Patent Application No. 61/652,549 filed 29 May 2012, all of which are herein specifically incorporated by reference in their entirety.

SEQUENCE LISTING

[This application incorporates by reference the sequence listing submitted in computer readable form as file 8150US02_ST25.txt created on Nov. 26, 2014 (206,400 bytes).] *The Sequence Listing in the ASCII text file, named as 35463ZA_REI_8150U507_REI_SequenceListing.txt of 202 KB, created on Apr. 16, 2019, and submitted to the United States Patent and Trademark Office via EFS-Web, is incorporated herein by reference.*

FIELD OF THE INVENTION

The invention relates to a cell or cells expressing a recombinant stress-response lectin for the improved production of a multi-subunit protein. Specifically, the invention provides a mammalian cell and cell-line derived therefrom containing a gene encoding EDEM2, and which yields antibody at a high titer.

BACKGROUND OF THE INVENTION

The manufacture of therapeutically active proteins requires proper folding and processing prior to secretion. Proper folding is particularly relevant for proteins, such as antibodies, which consist of multiple subunits that must be properly assembled before secretion. Eukaryotic cells have adapted a system that ensures the proper folding of proteins and the removal of misfolded proteins from the secretory pathway. This system is called the unfolded protein response (UPR) pathway, and it is triggered by the accumulation of misfolded proteins in the endoplasmic reticulum (ER).

An early event of the UPR is the activation of the transcription factor Xbp1, which in turn activates the transcription of endoplasmic reticulum degradation-enhancing alpha-mannosidase-like protein 2 (EDEM2), a member of the endoplasmic reticulum associated degradation (ERAD) pathway. EDEM2 facilitates the removal of misfolded proteins. The ERAD pathway comprises five steps: (1) chaperone-mediated recognition of malformed proteins, (2) targeting of malformed proteins to the retrotranslocation machinery or E3-ligases, which involves EDEM2, (3) initiation of retrotranslocation; (4) ubiquitylation and further retrotranslocation; and (5) proteosome targeting and degradation.

Antibodies are multi-subunit proteins comprising two heavy chains and two light chains, which must be properly folded and associated to form a functional heterotetramer. Any improvement in the efficient and accurate processing of the heavy and light chains to improve the yield or titer of functional antibody heterotetramers is desired.

SUMMARY OF THE INVENTION

Applicants made the surprising discovery that the ectopic expression of EDEM2 in a protein-manufacturing cell line increases the average output of protein per cell, increases the titer of protein secreted into the media, and increases the integrated cell density of production cell lines.

Thus, in one aspect, the invention provides a cell containing (a) a recombinant polynucleotide that encodes a stress-induced mannose-binding lectin and (b) a polynucleotide that encodes a multi-subunit protein. In some embodiments, the stress-induced mannose-binding lectin is an EDEM2 protein, non-limiting examples of which are provided in Table 1, and the multi-subunit protein is an antibody. In other embodiments, the cell also contains a polynucleotide that encodes the active spliced form of XBP1, non-limiting examples of which are provided in Table 2. In one embodiment, the cell is a mammalian cell, such as a CHO cell used in the manufacture of biopharmaceuticals.

In another aspect, the invention provides a cell line derived from the cell described in the previous aspect. By "derived from", what is meant is a population of cells clonally descended from an individual cell and having some select qualities, such as the ability to produce active protein at a given titer, or the ability to proliferate to a particular density. In some embodiments, the cell line, which is derived from a cell harboring the recombinant polynucleotide encoding a stress-induced mannose-binding lectin and a polynucleotide encoding a multi-subunit protein, is capable of producing the multi-subunit protein at a titer of at least 3 grams per liter of media (g/L), at least 5 g/L, or at least 8 g/L. In some embodiments, the cell line can attain an integrated cell density (ICD) that is at least 30% greater, at least 50% greater, at least 60% greater, or at least 90% greater than the integrated cell density attainable by a cell line derived from what is essentially the same cell but without the recombinant polynucleotide encoding the stress-induced mannose-binding lectin.

In another aspect, the invention provides an isolated or recombinant polynucleotide comprising a nucleic acid sequence encoding an EDEM2 protein, which is operably linked (cis) to a constitutive and ubiquitously expressed mammalian promoter, such as the ubiquitin C promoter. In some embodiments, the EDEM2 protein has the amino acid of SEQ ID NO: 8, or an amino acid sequence that is at least 92% identical to any one of SEQ ID NO: 1-7. In some embodiments, the polynucleotide comprises a nucleic acid sequence of SEQ ID NO: 16. In one particular embodiment, the polynucleotide consists of a nucleic acid sequence of SEQ ID NO: 14; and in another particular embodiment, SEQ ID NO: 15.

In another aspect, the invention provides an isolated or recombinant polynucleotide comprising a nucleic acid sequence encoding an XBP1 protein, which is operably linked to (in cis) a constitutive and ubiquitously expressed mammalian promoter, such as the ubiquitin C promoter. In some embodiments, the XBP1 protein has the amino acid of SEQ ID NO: 13, or an amino acid sequence that is at least 86% identical to any one of SEQ ID NO: 9-12. In some embodiments, the polynucleotide comprises a nucleic acid sequence of SEQ ID NO: 18. In one particular embodiment, the polynucleotide consists of a nucleic acid sequence of SEQ ID NO: 17.

In another aspect, the invention provides a cell that contains an EDEM2-encoding polynucleotide, as described in the prior aspect, and a polynucleotide that encodes a multi-subunit protein, such as an antibody. In some embodiments, the cell also contains an XBP1-encoding polynucleotide, as described in the preceding aspect. In one embodiment, the multi-subunit protein is an antibody, and the heavy chain of the antibody comprises an amino acid sequence of SEQ ID NO: 43 and SEQ ID NO: 44, and the light chain of the antibody comprises an amino acid sequence of SEQ ID NO: 45 and SEQ ID NO: 46. In this and several embodiments, each polypeptide subunit of the multi-subunit protein is encoded by a separate polynucleotide. Thus, for example, a polynucleotide encoding an antibody may include a polynucleotide encoding a heavy chain and a polynucleotide encoding a light chain, hence two subunits. In some embodiments, the cell is a Chinese hamster ovary (CHO) cell.

In one embodiment, the encoded multi-subunit protein is an anti-GDF8 antibody having a heavy chain variable region amino acid sequence of SEQ ID NO: 20 and a light chain variable region amino acid sequence of SEQ ID NO: 22. In one embodiment, the anti-GDF8 antibody comprises a heavy chain having an amino acid sequence of SEQ ID NO: 19 and a light chain having an amino acid sequence of SEQ ID NO: 21. In one embodiment, the polynucleotide that encodes the heavy chain of the anti-GDF8 antibody comprises a nucleic acid sequence of SEQ ID NO: 23; and the polynucleotide that encodes the light chain of the anti-GDF8 antibody comprises a nucleic acid sequence of SEQ ID NO: 25. In one embodiment, the polynucleotide that encodes the heavy chain of the anti-GDF8 antibody consists of a nucleic acid sequence of SEQ ID NO: 24; and the polynucleotide that encodes the light chain of the anti-GDF8 antibody consists of a nucleic acid sequence of SEQ ID NO: 25.

In another embodiment, the encoded multi-subunit protein is an anti-ANG2 antibody having a heavy chain variable region amino acid sequence of SEQ ID NO: 28 and a light chain variable region amino acid sequence of SEQ ID NO: 30. In one embodiment, the anti-ANG2 antibody comprises a heavy chain having an amino acid sequence of SEQ ID NO: 27 and a light chain having an amino acid sequence of SEQ ID NO: 29. In one embodiment, the polynucleotide that encodes the heavy chain of the anti-ANG2 antibody comprises a nucleic acid sequence of SEQ ID NO: 31; and the polynucleotide that encodes the light chain of the anti-ANG2 antibody comprises a nucleic acid sequence of SEQ ID NO: 33. In one embodiment, the polynucleotide that encodes the heavy chain of the anti-ANG2 antibody consists of a nucleic acid sequence of SEQ ID NO: 32; and the polynucleotide that encodes the light chain of the anti-ANG2 antibody consists of a nucleic acid sequence of SEQ ID NO: 34.

In another embodiment, the encoded multi-subunit protein is an anti-ANGPTL4 antibody having a heavy chain variable region amino acid sequence of SEQ ID NO: 36 and a light chain variable region amino acid sequence of SEQ ID NO: 38. In one embodiment, the anti-ANGPTL4 antibody comprises a heavy chain having an amino acid sequence of SEQ ID NO: 35 and a light chain having an amino acid sequence of SEQ ID NO: 37. In one embodiment, the polynucleotide that encodes the heavy chain of the anti-ANGPTL4 antibody comprises a nucleic acid sequence of SEQ ID NO: 39; and the polynucleotide that encodes the light chain of the anti-ANGPTL4 antibody comprises a nucleic acid sequence of SEQ ID NO: 41. In one embodiment, the polynucleotide that encodes the heavy chain of the anti-ANGPTL4 antibody consists of a nucleic acid sequence of SEQ ID NO: 40; and the polynucleotide that encodes the light chain of the anti-ANGPTL4 antibody consists of a nucleic acid sequence of SEQ ID NO: 42.

In another aspect, the invention provides a method of manufacturing a multi-subunit protein, by culturing a cell of the previous aspect in a medium, wherein the multi-subunit protein is synthesized in the cell and subsequently secreted into the medium. In some embodiments, the multi-subunit protein is an antibody, such as for example anti-GDF8, anti-ANG2, anti-ANGPTL4, or an antibody having a heavy chain sequence of SEQ ID NO: 43 and 44, and a light chain sequence of SEQ ID NO: 45 and 46. In some embodiments, the multi-subunit protein attains a titer of at least 3 g/L, at least 5 g/L, at least 6 g/L, or at least 8 g/L. In some embodiments, the cell proliferates in the medium and establishes an integrated cell density of about $\geq 5\times10^7$ cell-day/mL, about $\geq 1\times10^8$ cell-day/mL, or about $\geq 1.5\times10^8$ cell-day/mL.

In another aspect, the invention provides a multi-subunit protein, which is manufactured according to the method described in the preceding aspect. In one embodiment, the manufactured protein is an antibody. In some embodiments, the antibody consists of a heavy chain, which comprises an amino acid sequence of SEQ ID NO: 43 and SEQ ID NO: 44, and a light chain, which comprises an amino acid sequence of SEQ ID NO: 45 and SEQ ID NO: 46. In one specific embodiment, the manufactured multi-subunit protein is an anti-GDF8 antibody having a heavy chain variable region amino acid sequence of SEQ ID NO: 20 and a light chain variable region amino acid sequence of SEQ ID NO: 22. In another specific embodiment, the manufactured multi-subunit protein is an anti-ANG2 antibody having a heavy chain variable region amino acid sequence of SEQ ID NO: 28 and a light chain variable region amino acid sequence of SEQ ID NO: 30. In yet another specific embodiment, the manufactured multi-subunit protein is an anti-ANGPTL4 antibody having a heavy chain variable region amino acid sequence of SEQ ID NO: 36 and a light chain variable region amino acid sequence of SEQ ID NO: 38.

BRIEF DESCRIPTION OF THE DRAWINGS

FIG. 2A shows the FACS scans (flow cytometry-based autologous secretion trap (FASTR)) of several clones expressing XBP1. Inconsistency in the peaks is indicative of unstable growth (i.e. a variable or heterogeneous mixture) of the cells in the clones tested.

FIG. 2B shows the FACS scans of several clones expressing EDEM2, having little to no variation in the peaks representative of clonal stability in the clones tested. FIG. 2B depicts the clonal stability of several clonal cell-lines expressing EDEM2 and an antibody of interest.

DESCRIPTION OF THE INVENTION

Figure 1A:
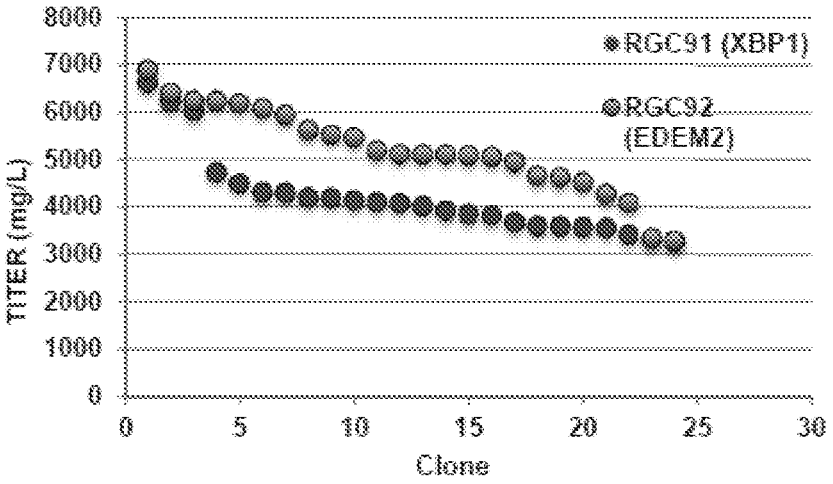
FIG. 1A shows consistently higher protein titer (in mg/L) for EDEM2-expressing clonal cell-lines (gray circles) compared to XBP1-expressing clonal cell-lines (black circles).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

As used herein, the term "recombinant polynucleotide", which is used interchangeably with "isolated polynucleotide", means a nucleic acid polymer such as a ribonucleic acid or a deoxyribonucleic acid, either single stranded or double stranded, originating by genetic engineering manipulations. A recombinant polynucleotide may be a circular plasmid or a linear construct existing in vitro or within a cell as an episome. A recombinant polynucleotide may be a construct that is integrated within a larger polynucleotide molecule or supermolecular structure, such as a linear or circular chromosome. The larger polynucleotide molecule or supermolecular structure may be within a cell or within the nucleus of a cell. Thus, a recombinant polynucleotide may be integrated within a chromosome of a cell.

As used herein, the term "stress-induced mannose-binding lectin" refers to a mannose-binding protein, which means a protein that binds or is capable of binding mannose, derivatives of mannose, such as mannose-6-phosphate, or a glycoprotein that expresses mannose or a mannose derivative in its glycocalyx; and whose activity is upregulated during stress. Cellular stress includes inter alia starvation, DNA damage, hypoxia, poisoning, shear stress and other mechanical stresses, tumor stress, and the accumulation of misfolded proteins in the endoplasmic reticulum. Exemplary stress-induced mannose-binding lectins include the EDEM proteins EDEM1, EDEM2 and EDEM3, Yos 9, OS9, and XTP3-B (see Vembar and Brodsky, Nat. Rev. Mol. Cell. Biol. 9(12): 944-957, 2008, and references cited therein).

As used herein, the term "EDEM2" means any ortholog, homolog, or conservatively substituted variant of endoplasmic reticulum degradation-enhancing alpha-mannosidase-like protein. EDEM2 proteins are generally known in the art to be involved endoplasmic reticulum-associated degradation (ERAD), being up-regulated by Xbp-1 and facilitating the extraction of misfolded glycoproteins from the calnexin cycle for removal. (See Mast et al., Glycobiology 15(4): 421-436, 2004; Olivari and Molinari, FEBS Lett. 581: 3658-3664, 2007; Olivari et al., J. Biol. Chem. 280(4): 2424-2428, 2005; and Vembar and Brodsky 2008, which are herein incorporated by reference.) Exemplary EDEM2 sequences are depicted in Table 1, which is cross-referenced to the Sequence Listing.

TABLE 1

| Animal | SEQ ID NO: | % id human | % id mouse | % id hamster |
|---|---|---|---|---|
| Mouse | 1 | 93 | 100 | 96 |
| Rat | 2 | 94 | 98 | 96 |
| Hamster | 3 | 93 | 96 | 100 |
| Human | 4 | 100 | 93 | 93 |
| Chimpanzee | 5 | 99 | 94 | 93 |
| Orangutan | 6 | 97 | 92 | 92 |
| Zebra fish | 7 | 69 | 70 | 69 |
| Consensus | 8 | 100 | 100 | 100 |

As used herein, the term "Xbp1", also known as XBP1 or X-box binding protein 1, means any ortholog, homolog, or conservatively substituted variant of Xbp1. Xbp1 is a transcription factor and functional element of the UPR. ER stress activates both (1) the transcription factor ATF6, which in turn upregulates the transcription of Xbp1 mRNA, and (2) the ER membrane protein IRE1, which mediates the splicing of the precursor Xbp1 mRNA to produce active Xbp1. As mentioned above, activated Xbp1 in turn upregulates the activity of EDEM2. (See Yoshida et al., Cell Structure and Function 31(2): 117-125, 2006; and Olivari, 2005.) Exemplary Xbp1 amino acid sequences are depicted in Table 2, which is cross-referenced to the Sequence Listing.

TABLE 2

| Alumat | SEQ ID NO | % id human | % id mouse | % id hamster |
|---|---|---|---|---|
| Mouse | 9 | 86 | 100 | 92 |
| Hamster | 10 | 86 | 92 | 100 |
| Human | 11 | 100 | 86 | 86 |
| Zebra fish | 12 | 47 | 47 | 48 |
| Consensus | 13 | 100 | 100 | 100 |

As used herein, the term "antibody" is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. An "isolated antibody" or "purified antibody" may be substantially free of other cellular material or chemicals.

The term "specifically binds", or the like, means that an antibody or antigen-binding fragment thereof forms a complex with an antigen that is relatively stable under physiologic conditions. Specific binding can be characterized by a dissociation constant of at least about $1\times10^{-6}$ M or greater. Methods for determining whether two molecules specifically bind are well known in the art and include, for example, equilibrium dialysis, surface plasmon resonance, and the like. An isolated antibody that specifically binds human GDF8 (for example) may, however, have cross-reactivity to other antigens, such as GDF8 molecules from other species (orthologs).

Various antibodies are used as examples of multi-subunit proteins secreted by cells harboring the polynucleotide encoding a stress-induced mannose-binding lectin. Those examples include anti-GDF8, anti-ANG2, and anti-ANGPTL4 antibodies. These and similar antibodies are described in US Pat. Apps. No. 20110293630, 20110027286, and 20110159015 respectively, which are incorporated herein by reference.

As used herein, the term "cell" refers to a prokaryotic or eukaryotic cell capable of replicating DNA, transcribing RNA, translating polypeptides, and secreting proteins. Cells include animal cells used in the commercial production of biological products, such as insect cells (e.g., Schneider cells, Sf9 cells, Sf21 cells, Tn-368 cells, BTI-TN-5B1-4 cells; see Jarvis, Methods Enzymol. 463: 191-222, 2009; and Potter et al., Int. Rev. Immunol. 10(2-3): 103-112, 1993) and mammalian cells (e.g., CHO or CHO-K1 cells, COS or COS-7 cells, HEK293 cells, PC12 cells, HeLa cells, Hybridoma cells; Trill et al., Curr. Opin. Biotechnol. 6(5): 553-560, 1995; Kipriyanov and Little, Mo. Biotechnol. 12(2): 173-201, 1999). In one embodiment, the cell is a CHO-K1 cell containing the described UPR pathway polynucleotides. For a description of CHO-K1 cells, see also Kao et al., Proc. Nat'l. Acad. Sci. USA 60: 1275-1281, 1968.

As used herein, the term "promoter" means a genetic sequence generally in cis and located upstream of a protein coding sequence, and which facilitates the transcription of the protein coding sequence. Promoters can be regulated (developmental, tissue specific, or inducible (chemical, temperature)) or constitutively active. In certain embodiments, the polynucleotides that encode proteins are operably linked to a constitutive promoter. By "operably linked", what is meant is that the protein-encoding polynucleotide is located three-prime (downstream) and cis of the promoter, and under control of the promoter. In certain embodiments, the promoter is a constitutive mammalian promoter, such as the ubiquitin C promoter (see Schorpp et al., Nucl. Acids Res. 24(9): 1787-1788, 1996); Byun et al., Biochem. Biophys. Res. Comm. 332(2): 518-523, 2005) or the CMV-IE promoter (see Addison et al., J. Gen. Virol. 78(7): 1653-1661, 1997; Hunninghake et al., J. Virol. 63(7): 3026-3033, 1989), or the hCMV-IE promoter (human cytomegalovirus immediate early gene promoter) (see Stinski & Roehr, J. Virol. 55(2): 431-441, 1985; Hunninghake et al., J. Virol. 63(7): 3026-3033, 1989).

As used herein, the phrase "integrated cell density", or "ICD" means the density of cells in a culture medium taken as an integral over a period of time, expressed as cell-days per mL. In some embodiments, the ICD is measured around the twelfth day of cells in culture.

As used herein, the term "culture" means both (1) the composition comprising cells, medium, and secreted multi-subunit protein, and (2) the act of incubating the cells in medium, regardless of whether the cells are actively dividing or not. Cells can be cultured in a vessel as small as a 25 mL flask or smaller, and as large as a commercial bioreactor of 10,000 liters or larger. "Medium" refers to the culture medium, which comprises inter alia nutrients, lipids, amino acids, nucleic acids, buffers and trace elements to allow the growth, proliferation, or maintenance of cells, and the production of the multi-subunit protein by the cells. Cell culture media include serum-free and hydrolysate-free defined media as well as media supplemented with sera (e.g., fetal bovine serum (FBS)) or protein hydrolysates. Non-limiting examples of media, which can be commercially acquired, include RPMI medium 1640, Dulbecco's Modified Eagle Medium (DMEM), DMEM/F12 mixture, F10 nutrient mixture, Ham's F12 nutrient mixture, and minimum essential media (MEM).

As used herein, the phrase "conservatively substituted variant", as applied to polypeptides, means a polypeptide having an amino acid sequence with one of more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-45, herein incorporated by reference. A "moderately conservative" replacement is any change having a nonnegative value in the PAM250 log-likelihood matrix.

Embodiments—The Cell

In one aspect, the invention provides a cell useful in the production of a protein having therapeutic or research utility. In some embodiments, the protein consists of multiple subunits, which must be properly folded and assembled to produce sufficient quantities of active protein. Antibodies are an example of multi-subunit proteins having therapeutic or research utility. In some embodiments, the cell harbors a recombinant genetic construct (i.e., a polynucleotide) that encodes one or more of the individual subunits of the multi-subunit protein. In other embodiments, the genetic construct encoding the individual polypeptide subunits is naturally occurring, such as for example the nucleic acid sequences encoding the subunits of an antibody in a B cell.

To facilitate the proper assembly and secretion of the multi-subunit protein, the cell contains a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant can be successfully employed in the instant invention. Table 1 lists some examples of vertebrate EDEM2 proteins. A multiple pairwise comparison of those protein sequences, which was performed using the Clustal W program of Thompson et al., Nucl. Acids Rev. 22(22): 4673-80, 1994 (see also Yuan et al., Bioinformatics 15(10): 862-3, 1999), revealed that each of the disclosed EDEM2 polynucleotide sequences is at least 69% identical to each other EDEM2 sequence. A Clustal W comparison of the disclosed mammalian EDEM2 sequences revealed that each sequence is at least 92% identical to the other. Thus, in some embodiments, the cell contains a polynucleotide that encodes an EDEM2 polypeptide having a sequence that is at least 92% to any one of a mammalian EDEM2. A consensus EDEM2 amino acid sequence was built by aligning a mouse, rat, hamster, chimpanzee, and human EDEM2 polypeptide amino acid sequences. That consensus sequence is depicted as SEQ ID NO: 8. Thus, in some embodiments, the cell contains a polynucleotide that encodes an EDEM2 polypeptide having an amino acid sequence of SEQ ID NO: 8.

In various embodiments, the cell contains a recombinant polynucleotide that encodes an EDEM2 polypeptide having an amino acid sequence that is at least 92% identical to the mouse EDEM2 (mEDEM2) amino acid sequence; and in a particular embodiment, the polypeptide is mEDEM2 or a conservatively substituted variant thereof.

In some embodiments, the multi-subunit protein is an antibody, and the cell contains a polynucleotide encoding any one or more of a polypeptide comprising an amino acid sequence of SEQ ID NO: 43, SEQ ID NO: 44, SEQ ID NO: 45, and SEQ ID NO: 46. SEQ ID NO: 43 and 44 each represent consensus sequences of the roughly N-terminal and C-terminal portions, respectively, of particular antibody heavy chains. Thus, the polynucleotide encoding a protein subunit in one embodiment encodes a polypeptide comprising both SEQ ID NO: 43 and SEQ ID NO: 44. SEQ ID NO: 45 and 46 each represent consensus sequences of the roughly N-terminal and C-terminal portions, respectively, of particular antibody light chains. Thus, the polynucleotide encoding a protein subunit in one embodiment encodes a polypeptide comprising both SEQ ID NO: 45 and SEQ ID NO: 46. In some embodiments, in addition to the recombinant polynucleotide encoding the EDEM2 protein, the cell contains at least two polynucleotides, each of which encodes a particular subunit of the multi-subunit protein. For example, and as exemplified below, the cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the cell, in addition to containing the stress-response polynucleotide and one or more polynucleotides encoding a polypeptide subunit, as described above, also contains a polynucleotide that encodes an unfolded protein response transcription factor that operates upstream of EDEM2. The upstream transcription factor is in some cases the spliced form of an XBP1. It is envisioned that any encoded XBP1 can be successfully employed in the instant invention. Table 2 lists some examples of sequences of vertebrate XBP1 spliced-form polypeptides. A multiple pairwise comparison of those polypeptide sequences, which was performed using Clustal W (Thompson 1994; Yuan 1999), revealed that each of the disclosed spliced XBP1 polynucleotide sequences is at least 48% identical to each other XBP1 sequence. A Clustal W comparison of the disclosed mammalian XBP1 sequences revealed that each sequence is at least 86% identical to the other. Thus, in some embodiments, the cell contains a polynucleotide that encodes a spliced-form of an XBP1 polypeptide having a sequence that is at least 86% to any one of a mammalian spliced XBP1. A consensus XBP1 amino acid sequence was built by aligning a mouse, hamster, and human XBP1 amino acid sequences. That consensus sequence is depicted as SEQ ID NO: 13. Thus, in some embodiments, the cell contains a polynucleotide that encodes an XBP1 polypeptide having an amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1, or a conservatively substituted variant thereof.

The invention envisions that any cell may be used to harbor the lectin-encoding polypeptide for the production of a properly folded and active multi-subunit protein. Such cells include the well-known protein production cells such as the bacterium Escherichia coli and similar prokaryotic cells, the yeasts Pichia pastoris and other Pichia and non-pichia yeasts, plant cell explants, such as those of Nicotiana, insect cells, such as Schneider 2 cells, Sf9 and Sf21, and the Trichoplusia ni-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell such as that which is taught in U.S. Pat. Nos. 7,435,553, 7,514,545, and 7,771,997, as well as U.S. Published Patent Application No. US 2010-0304436 A1, each of which is incorporated herein by reference in its entirety.

In some particular embodiments, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO:18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The Cell Line

In another aspect, the invention provides a cell line, which comprises a plurality of cells descended by clonal expansion from a cell described above. At least 50%, at least 60%, at least 70%, at least 80%, at least 90%, at least 95%, at least 98%, at least 99%, or about 100% of the constituent cells of the cell line contain a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant thereof can be successfully employed in the instant invention. Table 1, as discussed in the previous section, lists some examples of vertebrate EDEM2 proteins. In some embodiments, the constituent cell contains a polynucleotide that encodes an EDEM2 polypeptide having a sequence that is at least 92% identical to any mammalian EDEM2. In some embodiments, the constituent cell contains a polynucleotide that encodes an EDEM2 polypeptide having the mammalian consensus amino acid sequence of SEQ ID NO: 8. In some embodiments, the constituent cell contains a recombinant polynucleotide of SEQ ID NO: 1 or a conservatively substituted variant thereof.

In some embodiments, the multi-subunit protein that is produced by the cell line is an antibody, and the constituent cell of the cell line contains a polynucleotide encoding any one or more of a polypeptide comprising an amino acid sequence of SEQ ID NO: 43 and SEQ ID NO: 44 (which represent consensus sequences of the N-terminal and C-terminal portions, respectively, of particular antibody heavy chains), and SEQ ID NO: 45 and SEQ ID NO: 46 (which represent consensus sequences of the N-terminal and C-terminal portions, respectively, of particular antibody light chains). In some embodiments, in addition to the recombinant polynucleotide encoding the EDEM2 protein, the constituent cell of the cell line contains at least two polynucleotides, each of which encodes a particular subunit of the multi-subunit protein. For example, the constituent cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the constituent cell, in addition to containing the stress-response polynucleotide and one or more polynucleotides encoding a polypeptide subunit, as described above, also contains a polynucleotide that encodes an unfolded protein response transcription factor, which operates upstream of EDEM2, such as a spliced form of an XBP1. It is envisioned that any encoded XBP1 can be successfully employed in the instant invention. Table 2, as discussed in the preceding section, lists some examples of sequences of vertebrate XBP1 spliced-form polypeptides. Clustal W analysis of those sequences revealed that each of the disclosed spliced XBP1 polynucleotide sequences is at least 48% identical to each other XBP1 sequence; and a comparison of the mammalian XBP1 sequences revealed that each sequence is at least 86% identical to the other. Thus, in some embodiments, the constituent cell of the cell line contains a polynucleotide that encodes a spliced-form of an XBP1 polypeptide having a sequence that is at least 86% to any one of a mammalian spliced XBP1. In some embodiments, the constituent cell contains a polynucleotide that encodes an XBP1 polypeptide having a consensus amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1 of SEQ ID NO: 9, or a conservatively substituted variant thereof.

The invention envisions that the cell line comprises constituent cells whose parent is selected from a list of well-known protein production cells such as, e.g., the bacterium Escherichia coli and similar prokaryotic cells, the yeasts Pichia pastoris and other Pichia and non-pichia yeasts, plant cell explants, such as those of Nicotiana, insect cells, such as Schneider 2 cells, Sf9 and Sf21, and the Trichoplusia ni-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell, such as that which is taught in U.S. Pat. Nos. 7,435,553, 7,514,545, and 7,771,997, as well as U.S. Published Patent Application No. US 2010-0304436 A1.

In some embodiments, the cell line, which is cultured in media, is capable of producing the multi-subunit protein and secreting the properly assembled multi-subunit protein into the media to a titer that is at least 3 g/L, at least 5 g/L, or at least 8 g/L.

Furthermore, the constituent cells of the cell line are capable proliferating in culture to such an extent as to attain an integrated cell density that is about 30% greater than the integrated cell density of a cell line that does not contain the recombinant polynucleotide encoding the stress-induced mannose-binding lectin. In some cases, the cell line is able to attain an integrated cell density that is at least about 50% greater, at least 60% greater, or at least 90% greater than the integrated cell density of a cell line that does not contain the recombinant polynucleotide that encodes a stress-induced mannose-binding lectin. In some embodiments, the integrated cell density of the cell line is assessed after about 12 days in culture.

In some particular embodiments, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The EDEM2 Polynucleotide

In another aspect, the invention provides a polynucleotide that encodes an EDEM2 protein. The EDEM2-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the EDEM2-encoding polynucleotide is within a gene, meaning that it is under the control of and down stream of a promoter, and up stream of a polyadenylation site. The EDEM2-encoding polynucleotide or gene can be within a plasmid or other circular or linear vector. The EDEM2-encoding polynucleotide or gene can be within a circular or linear DNA construct, which can be within a cell as an episome or integrated into the cellular genome.

As described above, the EDEM2-encoding polynucleotide encodes any ortholog, homolog or conservatively substituted EDEM2 polypeptide of Table 1, or an EDEM2 polypeptide having an amino acid sequence that is at least 92% identical to any one of SEQ ID NO: 1-5 and 8, including the mammalian consensus sequence of SEQ ID NO: 8.

In some cases, the recombinant or isolated EDEM2-encoding polynucleotide is operably linked to a mammalian promoter. The promoter can be any promoter, but in some cases it is a mammalian promoter, such as for example a ubiquitin C promoter.

In a particular embodiment, the EDEM2-encoding polynucleotide essentially consists of, from 5' to 3', a promoter, such as a ubiquitin C promoter, followed by an optional intron, such as a beta globin intron, followed by an EDEM2 coding sequence, followed by a polyadenylation sequence, such as an SV40 pA sequence. A specific example, which is also a particular embodiment, of such an EDEM2-encoding polynucleotide is described by SEQ ID NO: 16. Conserved variants of that sequence are also envisioned to be embodiments of the invention.

In some cases, the recombinant EDEM2-encoding polynucleotide is part of a plasmid, which can be linear, circular, episomal, integrated, a static DNA construct, or a vector for delivering the EDEM2 gene or expressing the EDEM2 protein. In one particular embodiment, the plasmid contains (1) an EDEM2 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promoter, a beta globin intron, an EDEM2 coding sequence, an SV40 pA sequence, an SV40 promoter, a neomycin-resistance coding sequence, and a PGK pA sequence. A specific example of this embodiment is exemplified by a plasmid having the sequence of SEQ ID NO: 14. In another particular embodiment, the plasmid comprises, in a circular format running in a 5' to 3' direction, a ubiquitin C promoter, a beta globin intron, an EDEM2 coding sequence, an SV40 pA sequence, an SV40 promoter, a zeocin-resistance coding sequence, and a PGK pA sequence. A specific example of this embodiment is exemplified by a plasmid having the sequence of SEQ ID NO: 15.

The XBP1 Polynucleotide

In another aspect, the invention provides a polynucleotide that encodes an XBP1 protein. The XBP1-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the XBP1-encoding polynucleotide is within a gene, meaning that it is under the control of and down stream of a promoter, and up stream of a polyadenylation site. The XBP1-encoding polynucleotide can be within a plasmid or other circular or linear vector. The XBP1-encoding polynucleotide or gene can be within a circular or linear DNA construct, which can be within a cell as an episome, or integrated into the cellular genome.

As described above, the XBP1-encoding polynucleotide encodes any ortholog, homolog or conservatively substituted XBP1 polypeptide of Table 2, or an XBP1 polypeptide having an amino acid sequence that is at least 86% identical to any one of SEQ ID NO: 9, 10, and 11, including the mammalian consensus sequence of SEQ ID NO: 13.

In some cases, the recombinant or isolated XBP1-encoding polynucleotide is operably linked to a mammalian promoter. The promoter can be any promoter, but in some cases it is a mammalian promoter, such as for example a ubiquitin C promoter.

In a particular embodiment, the XBP1-encoding polynucleotide essentially consists of, from 5' to 3', a promoter, such as a ubiquitin C promoter, followed by an optional intron, such as a beta globin intron, followed by an XBP1 coding sequence, followed by a polyadenylation sequence, such as an SV40 pA sequence. SEQ ID NO: 18 describes an example of an XBP1-encoding polynucleotide. Conserved variants of that exemplary sequence are also envisioned to be embodiments of the invention.

In some cases, the recombinant XBP1-encoding polynucleotide is part of a plasmid, which can be linear, circular, episomal, integrated, a static DNA construct, or a vector for delivering the XBP1 gene or expressing the spliced and active XBP1 protein. In one particular embodiment, the plasmid contains (1) an XBP1 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promoter, a beta globin intron, an XBP1 coding sequence, an SV40 pA sequence, an SV40 promoter, a zeocin-resistance coding sequence, and a PGK pA sequence. A specific example of this embodiment is exemplified by a circular plasmid having the sequence of SEQ ID NO: 17.

The Antibody Heavy and Light Chain-Encoding Polynucleotides

In another aspect, the invention provides a polynucleotide that encodes an antibody heavy chain polypeptide (HC). The HC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the HC-encoding polynucleotide is within a gene, meaning that it is under the control of and down stream from a promoter, and up stream of a polyadenylation site. The HC-encoding polynucleotide may be within a plasmid or other circular or linear vector. The HC-encoding polynucleotide or gene may be within a circular or linear DNA construct, which may be within a cell as an episome or integrated into the cellular genome.

In some cases, the recombinant or isolated HC-encoding polynucleotide is operably linked to a mammalian promoter. The promoter can be any promoter, but in some cases it is a mammalian promoter, such as for example a ubiquitin C promoter or an hCMV-IE promoter.

In a particular embodiment, the HC-encoding polynucleotide is an HC gene, which essentially comprises, from 5' to 3', a promoter, for example an hCMV-IE promoter, followed by an optional intron, such as a beta globin intron, followed by a heavy chain coding sequence, such as for example a sequence encoding an amino acid sequence of SEQ ID NO: 43 and 44, SEQ ID NO: 19, SEQ ID NO: 27, or SEQ ID NO: 35, followed by a polyadenylation sequence, for example an SV40 pA sequence. A specific example of an HC gene is described by SEQ ID NO: 23, SEQ ID NO: 31, or SEQ ID NO: 39. Conserved variants of any one of these sequences are also envisioned to be embodiments of the invention.

In some cases, the recombinant HC-encoding polynucleotide is part of a plasmid, which can be linear, circular, episomal, integrated, a static DNA construct, or a vector for delivering the heavy chain gene or expressing the heavy chain sububunit. In one particular embodiment, the plasmid contains (1) an HC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody heavy chain coding sequence (which encodes a HC having an amino acid of SEQ ID NO: 43 and 44, SEQ ID NO: 19, SEQ ID NO: 27, or SEQ ID NO: 35), an SV40 pA sequence, an SV40 promoter, a hygromycin-resistance coding sequence, and a PGK pA sequence. A specific example and particular embodiment of such a plasmid containing an HC gene is described by SEQ ID NO: 24, SEQ ID NO: 32, or SEQ ID NO: 40. Conserved variants of any one of these sequences are also envisioned to be embodiments of the invention.

In another aspect, the invention provides a polynucleotide that encodes an antibody light chain polypeptide (LC). The LC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the LC-encoding polynucleotide is within a gene, meaning that it is under the control of and down stream from a promoter, and up stream of a polyadenylation site. The LC-encoding polynucleotide or gene may be within a plasmid or other circular or linear vector. The LC-encoding polynucleotide or gene may be within a circular or linear DNA construct, which may be within a cell as an episome or integrated into the cellular genome.

In some cases, the recombinant or isolated LC-encoding polynucleotide is operably linked to a mammalian promoter. The promoter can be any promoter, but in some cases it is a mammalian promoter, such as, e.g., a ubiquitin C promoter or an hCMV-IE promoter.

In a particular embodiment, the LC-encoding polynucleotide is an LC gene, which essentially comprises, from 5' to 3', a promoter, for example an hCMV-IE promoter, followed by an optional intron, such as a beta globin intron, followed by a light chain coding sequence, such as for example a sequence encoding an amino acid sequence of SEQ ID NO: 45 and 46, SEQ ID NO: 21, SEQ ID NO: 29, or SEQ ID NO: 37, followed by a polyadenylation sequence, such as an SV40 pA sequence. A specific example and particular embodiment of such an LC gene is described by SEQ ID NO: 25, SEQ ID NO: 33, or SEQ ID NO: 41. Conserved variants of any one of these sequences are also envisioned to be embodiments of the invention.

In some cases, the recombinant LC-encoding polynucleotide is part of a plasmid, which may be linear, circular, episomal, integrated, a static DNA construct, or a vector for delivering the light chain gene or expressing the light chain sububunit. In one particular embodiment, the plasmid contains (1) an LC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody light chain coding sequence (which encodes a LC having an amino acid of SEQ ID NO: 45 and 46, SEQ ID NO: 21, SEQ ID NO: 29, or SEQ ID NO: 37), an SV40 pA sequence, an SV40 promoter, a hygromycin-resistance coding sequence, and a PGK pA sequence. A specific example and particular embodiment of such a plasmid containing an LC gene is described by SEQ ID NO: 26, SEQ ID NO: 34, or SEQ ID NO: 42. Conserved variants of any one of these sequences are also envisioned to be embodiments of the invention.

Methods of Manufacturing Multi-subunit Proteins

In another aspect, the invention provides a method for manufacturing a multi-subunit protein by culturing a cell, or a constituent cell of a cell line, which is capable of producing and secreting relatively large amounts of a properly assembled multi-subunit protein, in a medium, wherein the multi-subunit component is secreted into the medium at a relatively high titer. The cell utilized in this manufacturing process is a cell described in the foregoing aspects, which contains an ERAD lectin-encoding polynucleotide described herein.

Methods of culturing cells, and in particular mammalian cells, for the purpose of producing useful recombinant proteins is well-known in the art (e.g., see De Jesus & Wurm, Eur. J. Pharm. Biopharm. 78:184-188, 2011, and references cited therein). Briefly, cells containing the described polynucleotides are cultured in media, which may contain sera or hydrolysates, or may be chemically defined and optimized for protein production. The cultures may be fed-batch cultures or continuous cultures, as in a chemostat. The cells may be cultured in lab bench size flasks (~25 mL), production scale-up bioreactors (1-5 L), or industrial scale bioreactors (5,000-25,000 L). Production runs may last for several weeks to a month, during which time the multi-subunit protein is secreted into the media.

The subject cell has an enhanced ability to produce and secrete properly assembled multi-subunit proteins. In some embodiments, the multi-subunit protein, for example an antibody, is secreted into the media at a rate of at least 94 ρg/cell/day, at least 37 ρg/cell/day, or at least 39 ρg/cell/day. In some embodiments, the multi-subunit protein attains a titer of at least at least 3 g/L, at least 5 g/L, at least 6 g/L, or at least 8 g/L after about twelve days of culture.

Furthermore, the subject cell has an enhanced ability to proliferate and attain a relatively high cell density, further optimizing productivity. In some embodiments, the cell or cell-line seed train attains an integrated cell density in culture of at least $5\times10^7$ cell-day/mL, at least $1\times10^8$ cell-day/mL or at least $1.5\times10^8$ cell-day/mL.

Optionally, the secreted multi-subunit protein is subsequently purified from the medium into which it was secreted. Protein purification methods are well-known in the art (see e.g., Kelley, mAbs 1(5):443-452). In some embodiments, the protein is harvested by centrifugation to remove the cells from the liquid media supernatant, followed by various chromatography steps and a filtration step to remove inter alia viruses and other contaminants or adulterants. In some embodiments, the chromatography steps include an ion exchange step, such as cation-exchange or anion-exchange. Various affinity chromatographic media may also be employed, such as protein A chromatography for the purification of antibodies.

Optionally, the manufacturing method may include the antecedent steps of creating the cell. Thus, in some embodiments, the method of manufacturing the multi-subunit protein comprises the step of transfecting the cell with the vector that encodes the stress-induced mannose-binding lectin, as described above, followed by selecting stable integrants thereof. Non-limiting examples of vectors include those genetic constructs that contain a polynucleotide that encodes an EDEM2 having an amino acid sequence of any one of SEQ ID NO: 1-8, an amino acid sequence that is at least 92% identical to any one of SEQ ID NO: 1-8, or any one of a conservatively substituted variant of SEQ ID NO: 1-8. Useful vectors also include, for example, a plasmid harboring the gene of SEQ ID NO: 16, the plasmid of SEQ ID NO: 15, and the plasmid of SEQ ID NO: 14. One should keep in mind that the plasmid sequences (e.g., SEQ ID NO: 14, 15, 17, 24, 26, 32, 34, 40, and 42) are circular sequences described in a linear manner in the sequence listing. Thus, in those cases, the 3-prime-most nucleotide of the written sequence may be considered to be immediately 5-prime of the 5-prime-most nucleotide of the sequence as written. In the example of the plasmid of SEQ ID NO: 14, transformants are selected through resistance to neomycin; for SEQ ID NO: 15, by selection through ZEOCIN resistance.

Detailed methods for the construction of polynucleotides and vectors comprising same, are described in U.S. Pat. Nos. 7,435,553 and 7,771,997, which are incorporated herein by reference, and in, e.g., Zwarthoff et al., J. Gen. Virol. 66(4):685-91, 1985; Mory et al., DNA. 5(3):181-93, 1986; and Pichler et al., Biotechnol. Bioeng. 108(2):386-94, 2011.

The starting cell, into which the vector that encodes the stress-induced mannose-binding lectin is placed, may already contain the constructs or genetic elements encoding or regulating the expression of the subunits of the multi-subunit protein, or XBP1 for those embodiments utilizing XBP1. Alternatively, the vector that encodes the stress-induced mannose-binding lectin may be put inside the cell first, and followed by the other constructs.

Multi-Subunit Proteins Manufactured by the Process

In another aspect, the invention provides a multi-subunit protein that is made according to the process disclosed herein. Given the inclusion of one or more elements that facilitate the proper folding, assembly, and post-translational modification of a multi-subunit protein, such as an antibody, one of ordinary skill in the art would reasonably expect such a protein to have distinct structural and functional qualities. For example, an antibody manufactured by the disclosed process is reasonably believed to have a particular glycosylation pattern and a quantitatively greater proportion of non-aggregated heterotetramers.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, percent concentration (%) means the mass of the solute in grams divided by the volume of the solution in milliliters times 100% (e.g., 10% substance X means 0.1 gram of substance X per milliliter of solution), temperature is in degrees Centigrade, and pressure is at or near atmospheric pressure.

Example 1

Cell Lines

CHO-K1 derived host cell line was transfected with two plasmids encoding heavy and light chain of a human antibody. Both plasmids contain the hph gene conferring resistance to hygromycin B (Asselbergs and Pronk, 1992, Mol. Biol. Rep., 17(1):61-70). Cells were transfected using LIPOFECTAMIN reagent (Invitrogen cat.#18324020). Briefly, one day before transfection 3.5 million cells were plated on a 10 cm plate in complete F12 (Invitrogen cat.#11765) containing 10% fetal bovine serum (FBS) (Invitrogen cat.#10100). On the day of transfection the cells were washed once and medium was replaced with OPTIMEM from (Invitrogen cat.#31985). DNA/Lipofectamin complexes were prepared in OPTIMEM medium and then added to the cells. The medium was changed again to the complete F12 with 10% FBS 6 hours later. The stable integration of the plasmids was selected using hygromycin B selection agent at 400 μg/ml. Clonal antibody expressing cell lines were isolated using the FASTR technology (described in the U.S. Pat. No. 6,919,183, which is herein incorporated by reference).

The antibody expressing lines were then re-transfected with the EDEM2 encoding plasmid. EDEM2 plasmids contained either neomycin phosphotransferase (plasmid construct designated "p3") or sh ble (plasmid "p7") genes to confer resistance to either G418 or zeocin respectively. The same transfection method was used. Depending on the selectable marker, cells were selected with either G418 or zeocin at 400 μg/ml or 250 μg/ml, respectively. The clonal cell lines were then isolated using FASTR technology.

TABLE 3

| Cell Lines | | | |
|---|---|---|---|
| Name | Enhancers | Constructs | Protein |
| C1 | EDEM2 + XBP1 | HC/LC = p1/p2 | αAng2 |
| C2 | XBP1 | EDEM2 = p3<br>XBP1 = p4 | |
| C3 | EDEM2 + XBP1 | HC/LC = p5/p6 | αGDF8 |
| C4 | XBP1 | EDEM2 = p7 | |
| C5 | EDEM2 | XBP1 = p4 | |
| C6 | EDEM2 + XBP1 | HC/LC = p8/p9 | αAngPtl4 |
| C7 | XBP1 | EDE3M2 = p3<br>XBP1 = p4 | |

Example 2

The antibody production was evaluated in a scaled-down 12-day fed batch process using shaker flasks. In this method the cells were seeded in a shaker flask at the density of 0.8 million cells per mL in the production medium (defined media with high amino acid). The culture was maintained for about 12 days, and was supplemented with three feeds as well as glucose. The viable cell density, and antibody titer were monitored throughout the batch.

To determine the effect of mEDEM2 on enhanced protein production, the production of proteins by CHO cell lines containing mEDEM2 and mXBP1 were compared to production by control cells that contained mXBP1, but not mEDEM2. Protein titers were higher in those cell lines expressing mEDEM2 versus those cell lines that did not express mEDEM2.

TABLE 4

| TITERS | | | |
|---|---|---|---|
| Cell Line | Enhancers | Production rate (ρg/cell/day) | Titre g/L (% increase) |
| C1 | EDEM2 + XBP1 | 39 | 8.1 (93) |
| C2 | XBP1 | 39 | 4.2 |
| C3 | EDEM2 + XBP1 | 37 | 5.9 (55) |
| C8 | XBP1 | 32 | 3.8 |
| C6 | EDEM2 + XBP1 | 94 | 5.3 (152) |
| C7 | XBP1 | 52 | 2.1 |
| C5 | EDEM2 | 29 | 3.1 (343) |
| C9 | — | 9 | 0.7 |

Example 3

Integrated Cell Days

Integrated Cell Density ("ICD") is a phrase used to describe the growth of the culture throughout the fed batch process. In the course of the 12-day production assay, we monitored viable cell density on days 0, 3, 5, 7, 10, and 12. This data was then plotted against time. ICD is the integral of viable cell density, calculated as the area under the cell density curve. EDEM2 transfected lines have higher ICD in a 12-day fed batch process (see Table 5).

TABLE 5

| INTEGRATED CELL DENSITIES | | |
|---|---|---|
| Cell Line | Enhancers | ICD $10^6$ cell-day/mL (% increase) |
| C1 | EDEM2 + XBP1 | 205 (93) |
| C2 | XBP1 | 106 |
| C3 | EDEM2 + XBP1 | 157 (34) |
| C4 | XBP1 | 117 |
| C6 | EDEM2 + XBP1 | 56 (51) |
| C7 | XBP1 | 37 |
| C5 | EDEM2 | 116 (59) |
| C9 | — | 73 |

Example 4

Anti-GDF8 Antibody Production

The effect of ectopic expression of EDEM2, XBP1, or both on the production of an anti-GDF8 antibody having a heavy chain sequence of SEQ ID NO: 19 and a light chain sequence of SEQ ID NO: 21 was examined. Individual cell-lines were examined for titer and integrated cell density and placed into "bins", or ranges of values. Ectopic expression of EDEM2 significantly increased the number of cell lines that express antibody in the 5-6 g/L titer range. The combination of XBP1 and EDEM2 showed more than an additive effect toward the increase in high titer cell lines. The expression of EDEM2 in the antibody secreting cells also significantly increased the number of cell lines that attain a high ICD (see Table 6).

TABLE 6

| con- | Titre Bins (g/l) | | | | ICD Bins ($10^6$ cell-day/mL) | | |
|---|---|---|---|---|---|---|---|
| struct | <1 | 1-3 | 3-5 | 5-6 | 30-50 | 50-100 | 100-200 |
| E + X | 0% | 33.3% | 44.4% | 22.2% | 11.1% | 50% | 38.9% |
| X | 0% | 37.5% | 54% | 8.3% | 14.3% | 85.7% | 0% |
| E | 0% | 33% | 60% | 7% | 0% | 27% | 73% |
| — | 82% | 18% | 0% | 0% | 13% | 67% | 21% |

Example 5

Productivity and Stability of EDEM2-Expressing Cells

The effect of ectopic expression of XBP1 or EDEM2 on the production of a monospecific antibody of interest (identified as clonal cell lines RGC91 or RGC92, respectively) was examined. Individual cell lines were examined for protein titer and integrated cell density, as well as stability.

Modified CHO K1 host cells stably expressing XBP1 (RGC91) or EDEM2 (RGC92) at a transcriptionally active locus (U.S. Pat. No. 8,389,239B2, issued Mar. 5, 2013) were transfected with a recombinant plasmid vector comprising the antibody gene of interest and a hygromycin resistance gene (hyg).

400 μg/mL hygromycin was used for selection of transfected cells. Positive integrants expressing the antibody of interest (randomly integrated in the CHO genome), and also stably expressing either XBP1 or EDEM2, were confirmed and isolated by fluorescence-activated cell sorting (FACS) analysis. The isolated clones were expanded in suspension cultures in serum-free production medium. Clones were isolated from selected pools and were subjected to a 12 day fed batch productivity assay, and the protein titer of the antibody of interest was determined. Integrated cell density is calculated by measuring viable cell count on a given day in the production assay (counts are taken every 3 days and plotted on a curve against cell count).

Figure 1B:
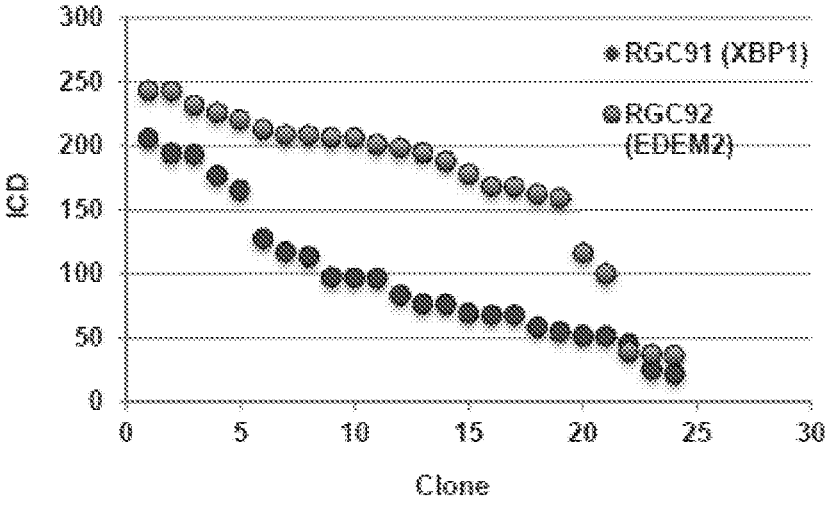
FIG. 1B depicts the integrated cell density (cell-days/mL) for EDEM2-expressing clones (gray circles) compared to XBP1-expressing clones (black circles). Each clone (#1-24) expresses the same gene of interest (antibody), under the same regulatory conditions, and expressing either XBP1 (RGC91) or EDEM2 (RGC92) at a transcriptionally active locus.

As shown in FIG. 1A, the average protein titers for clones isolated from RGC91 and RGC92 was 4.2 and 5.2, respectively (for 24 representative antibody-expressing clones). Ectopic expression of EDEM2 increased the number of clones that attain antibody titer above 5 g/L (FIG. 1A) compared to XBP1-expressing clones. Clonal cell lines expressing EDEM2 isolated from the RGC92 host also maintained higher (25%-100% higher) integrated cell densities when compared to clones isolated from XBP1-expressing RGC91 host (see FIG. 1B). EDEM2 clones established an ICD greater than 100 (FIG. 1B) in most clones tested. Clones isolated from EDEM2 expressing RGC92 host also resulted in significantly higher stability (FIG. 2B), as observed in flow cytometry-based autologous secretion trap (FASTR) scans (for reference, U.S. Pat. No. 6,919,183B2, issued Jul. 19, 2005) showing a homogenous producing population, in the representative sample of 24 clonal cell lines tested. Many of the clones isolated from XBP1 expressing RGC91 host appear to have a non-producing heterogeneous cell population (FIG. 2A). Without being bound to any one theory, EDEM2 facilitated the removal of misfolded proteins in the high expressing clones, thereby reducing stress in the cell during protein production and resulting in a more stable cell population.

SEQUENCE LISTING

```
<160> NUMBER OF SEQ ID NOS: 46

<210> SEQ ID NO 1
<211> LENGTH: 577
<212> TYPE: PRT
<213> ORGANISM: Mus musculus

<400> SEQUENCE: 1

Met Pro Phe Arg Leu Leu Ile Pro Leu Gly Leu Val Cys Val Leu Leu
1               5                   10                  15

Pro Leu His His Gly Ala Pro Gly Pro Asp Gly Thr Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Tyr Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
```

```
            260                 265                 270

Asp Lys Lys Leu Met Ala Met Phe Leu Glu Tyr Asn Lys Ala Ile Arg
        275                 280                 285

Asn Tyr Thr His Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
        435                 440                 445

Asn Asn Gly Ser Thr Phe Asp Ser Val Met Thr Pro His Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
                485                 490                 495

Glu Val Glu Asp Leu Ile Lys Glu Phe Tyr Ser Leu Lys Gln Ser Arg
            500                 505                 510

Pro Lys Arg Ala Gln Arg Lys Thr Val Arg Ser Gly Pro Trp Glu Pro
        515                 520                 525

Gln Ser Gly Pro Ala Thr Leu Ser Ser Pro Ala Asn Gln Pro Arg Glu
    530                 535                 540

Lys Gln Pro Ala Gln Gln Arg Thr Pro Leu Leu Ser Cys Pro Ser Gln
545                 550                 555                 560

Pro Phe Thr Ser Lys Leu Ala Leu Leu Gly Gln Val Phe Leu Asp Ser
                565                 570                 575

Ser


<210> SEQ ID NO 2
<211> LENGTH: 576
<212> TYPE: PRT
<213> ORGANISM: Rattus norvegicus

<400> SEQUENCE: 2

Met Pro Phe Arg Leu Leu Ile Pro Leu Gly Leu Val Cys Val Leu Leu
1               5                   10                  15

Pro Leu His His Gly Ala Pro Gly Pro Glu Gly Thr Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Tyr Asp Glu Leu Arg Pro Leu Thr
```

```
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr His Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
        435                 440                 445

Asn Asn Gly Ser Thr Phe Asp Ser Val Met Thr Pro His Gly Glu Cys
    450                 455                 460

Ile Leu Gly Ala Gly Gly Tyr Ile Phe Asn Thr Glu Ala His Pro Ile
465                 470                 475                 480
```

```
Asp Pro Ala Ala Leu His Cys Cys Arg Arg Leu Lys Glu Glu Gln Trp
                485                 490                 495

Glu Val Glu Asp Leu Ile Lys Glu Phe Tyr Ser Leu Arg Gln Ser Arg
            500                 505                 510

Ser Arg Ala Gln Arg Lys Thr Val Ser Ser Gly Pro Trp Glu Pro Pro
        515                 520                 525

Ala Gly Pro Gly Thr Leu Ser Ser Pro Glu Asn Gln Pro Arg Glu Lys
    530                 535                 540

Gln Pro Ala Arg Gln Arg Ala Pro Leu Leu Ser Cys Pro Ser Gln Pro
545                 550                 555                 560

Phe Thr Ser Lys Leu Ala Leu Leu Gly Gln Val Phe Leu Asp Ser Ser
                565                 570                 575


<210> SEQ ID NO 3
<211> LENGTH: 578
<212> TYPE: PRT
<213> ORGANISM: Cricetulus griseus

<400> SEQUENCE: 3

Met Pro Phe Arg Leu Leu Ile Pro Leu Gly Leu Val Cys Val Phe Leu
1               5                   10                  15

Pro Leu His His Gly Ala Pro Gly Pro Asp Gly Thr Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Tyr Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Leu Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Arg Ala Ile Arg
```

```
        275                 280                 285

Asn Tyr Thr His Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Ala Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
        435                 440                 445

Asn Asn Gly Ser Thr Phe Asp Ser Val Met Thr Pro His Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
                485                 490                 495

Glu Val Glu Asp Leu Met Arg Glu Leu His Ser Leu Lys Gln Ser Arg
            500                 505                 510

Ser Arg Ala Gln Arg Lys Thr Thr Ser Ser Gly Pro Trp Glu Pro Pro
        515                 520                 525

Ala Gly Pro Gly Ser Pro Ser Ala Pro Gly Lys Gln Asp Gln Pro Arg
    530                 535                 540

Glu Lys Gln Pro Ala Lys Gln Arg Thr Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser


<210> SEQ ID NO 4
<211> LENGTH: 578
<212> TYPE: PRT
<213> ORGANISM: Homo sapiens

<400> SEQUENCE: 4

Met Pro Phe Arg Leu Leu Ile Pro Leu Gly Leu Leu Cys Ala Leu Leu
1               5                   10                  15

Pro Gln His His Gly Ala Pro Gly Pro Asp Gly Ser Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Phe Asp Glu Leu Arg Pro Leu Thr
    50                  55                  60

Cys Asp Gly His Asp Thr Trp Gly Ser Phe Ser Leu Thr Leu Ile Asp
```

```
65                  70                  75                  80

Ala Leu Asp Thr Leu Leu Ile Leu Gly Asn Val Ser Glu Phe Gln Arg
                85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr Arg Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe Asp Pro Thr Asn Phe Ile His
        435                 440                 445

Asn Asn Gly Ser Thr Phe Asp Thr Val Ile Thr Pro Tyr Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
                485                 490                 495
```

```
Glu Val Glu Asp Leu Met Arg Glu Phe Tyr Ser Leu Lys Arg Ser Arg
            500                 505                 510

Ser Lys Phe Gln Lys Asn Thr Val Ser Ser Gly Pro Trp Glu Pro Pro
        515                 520                 525

Ala Arg Pro Gly Thr Leu Phe Ser Pro Glu Asn His Asp Gln Ala Arg
    530                 535                 540

Glu Arg Lys Pro Ala Lys Gln Lys Val Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser


<210> SEQ ID NO 5
<211> LENGTH: 578
<212> TYPE: PRT
<213> ORGANISM: Pan troglodytes

<400> SEQUENCE: 5

Met Pro Phe Arg Leu Leu Ile Pro Leu Gly Leu Leu Cys Ala Leu Leu
1               5                   10                  15

Pro Leu His His Gly Ala Pro Gly Pro Asp Gly Ser Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Phe Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Val Ser Glu Phe Gln Arg
                85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285
```

```
Asn Tyr Thr Arg Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe Asp Pro Thr Asn Phe Ile His
        435                 440                 445

Asn Asn Gly Ser Thr Phe Asp Ala Val Ile Thr Pro Tyr Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
                485                 490                 495

Glu Val Glu Asp Leu Met Arg Glu Phe Tyr Ser Leu Lys Arg Ser Arg
            500                 505                 510

Ser Lys Phe Gln Lys Lys Thr Val Ser Ser Gly Pro Trp Glu Pro Pro
        515                 520                 525

Ala Arg Pro Gly Thr Leu Phe Ser Pro Glu Asn His Asp Gln Ala Arg
    530                 535                 540

Glu Arg Lys Pro Ala Lys Gln Lys Val Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser


<210> SEQ ID NO 6
<211> LENGTH: 513
<212> TYPE: PRT
<213> ORGANISM: Pongo pygmaeus

<400> SEQUENCE: 6

Met Asn Thr Leu Ser Cys Ser Leu Phe Ser Leu Thr Leu Ile Asp Ala
1               5                   10                  15

Leu Asp Thr Leu Leu Ile Leu Gly Asn Val Ser Glu Phe Gln Arg Val
            20                  25                  30

Val Glu Val Leu Gln Asp Asn Val Asp Phe Asp Ile Asp Val Asn Ala
        35                  40                  45

Ser Val Phe Glu Thr Asn Ile Arg Val Val Gly Gly Leu Leu Ser Ala
    50                  55                  60

His Leu Leu Ser Lys Lys Ala Gly Val Glu Val Glu Ala Gly Trp Pro
65                  70                  75                  80
```

```
Cys Ser Gly Pro Leu Leu Arg Met Ala Glu Glu Ala Ala Arg Lys Leu
                85                  90                  95

Leu Pro Ala Phe Gln Thr Pro Thr Gly Met Pro Tyr Gly Thr Val Asn
            100                 105                 110

Leu Leu His Gly Val Asn Pro Gly Glu Thr Pro Val Thr Cys Thr Ala
        115                 120                 125

Gly Ile Gly Thr Phe Ile Val Glu Phe Ala Thr Leu Ser Ser Leu Thr
    130                 135                 140

Gly Asp Pro Val Phe Glu Asp Val Ala Arg Val Ala Leu Met Arg Leu
145                 150                 155                 160

Trp Glu Ser Arg Ser Asp Ile Gly Leu Val Gly Asn His Ile Asp Val
                165                 170                 175

Leu Thr Gly Lys Trp Val Ala Gln Asp Ala Gly Ile Gly Ala Gly Val
            180                 185                 190

Asp Ser Tyr Phe Glu Tyr Leu Val Lys Gly Ala Ile Leu Leu Gln Asp
        195                 200                 205

Lys Lys Leu Met Ala Met Phe Leu Glu Tyr Asn Lys Ala Ile Arg Asn
    210                 215                 220

Tyr Thr Arg Phe Asp Asp Trp Tyr Leu Trp Val Gln Met Tyr Lys Gly
225                 230                 235                 240

Thr Val Ser Met Pro Val Phe Gln Ser Leu Glu Ala Tyr Trp Pro Gly
                245                 250                 255

Leu Gln Ser Leu Ile Gly Asp Ile Asp Asn Ala Met Arg Thr Phe Leu
            260                 265                 270

Asn Tyr Tyr Thr Val Trp Lys Gln Phe Gly Gly Leu Pro Glu Phe Tyr
        275                 280                 285

Asn Ile Pro Gln Gly Tyr Thr Val Glu Lys Arg Glu Gly Tyr Pro Leu
    290                 295                 300

Arg Pro Glu Leu Ile Glu Ser Ala Met Tyr Leu Tyr Arg Ala Thr Gly
305                 310                 315                 320

Asp Pro Thr Leu Leu Glu Leu Gly Arg Asp Ala Val Glu Ser Ile Glu
                325                 330                 335

Lys Ile Ser Lys Val Glu Cys Gly Phe Ala Thr Ile Lys Asp Leu Arg
            340                 345                 350

Asp His Lys Leu Asp Asn Arg Met Glu Ser Phe Phe Leu Ala Glu Thr
        355                 360                 365

Val Lys Tyr Leu Tyr Leu Leu Phe Asp Pro Thr Asn Phe Ile His Asn
    370                 375                 380

Asn Gly Ser Thr Phe Asp Ala Val Ile Thr Pro Tyr Gly Glu Cys Ile
385                 390                 395                 400

Leu Gly Ala Gly Gly Tyr Ile Phe Asn Thr Glu Ala His Pro Ile Asp
                405                 410                 415

Pro Ala Ala Leu His Cys Cys Gln Arg Leu Lys Glu Glu Gln Trp Glu
            420                 425                 430

Val Glu Asp Leu Met Arg Glu Phe Tyr Ser Leu Lys Arg Asn Arg Ser
        435                 440                 445

Lys Phe Gln Lys Lys Thr Val Ser Ser Gly Pro Trp Glu Pro Pro Ala
    450                 455                 460

Arg Pro Gly Thr Leu Phe Ser Pro Glu Asn His Asp Gln Ala Arg Gly
465                 470                 475                 480

Arg Lys Pro Ala Lys Gln Lys Val Pro Leu Leu Ser Cys Pro Ser Gln
                485                 490                 495
```

```
Pro Phe Thr Ser Lys Leu Ala Leu Leu Gly Gln Val Phe Leu Asp Ser
            500                 505                 510

Ser


<210> SEQ ID NO 7
<211> LENGTH: 572
<212> TYPE: PRT
<213> ORGANISM: Danio rerio

<400> SEQUENCE: 7

Leu Tyr Tyr Leu Pro Leu Phe Thr Ser Arg Tyr Phe Met Leu Thr Phe
1               5                   10                  15

Leu Phe Ser Ala Ile Phe Cys Ala Ala Tyr Leu Ser Pro Ile Ile Ser
            20                  25                  30

His Val Lys Gly Arg Asp Phe Thr Glu Gln Glu Met Ser His Tyr Arg
        35                  40                  45

Asp Arg Val Lys Ser Met Phe Tyr His Ala Tyr Asn Ser Tyr Leu Asp
    50                  55                  60

Asn Ala Tyr Pro Tyr Asp Glu Leu Arg Pro Leu Thr Cys Asp Gly Gln
65                  70                  75                  80

Asp Thr Trp Gly Ser Phe Ser Leu Thr Leu Ile Asp Ala Leu Asp Thr
                85                  90                  95

Leu Leu Ile Leu Gly Asn His Thr Glu Phe Gln Arg Val Ala Thr Leu
            100                 105                 110

Leu Gln Asp Thr Val Asp Phe Asp Ile Asp Val Asn Ala Ser Val Phe
        115                 120                 125

Glu Thr Asn Ile Arg Val Val Gly Gly Leu Leu Ser Ala His Leu Leu
    130                 135                 140

Ser Lys Arg Ala Gly Met Lys Val Glu Glu Gly Trp Pro Cys Ser Gly
145                 150                 155                 160

Pro Leu Leu Arg Met Ala Glu Asp Ala Ala Arg Lys Leu Leu Pro Ala
                165                 170                 175

Phe Gln Thr Pro Thr Gly Met Pro Tyr Gly Thr Val Asn Leu Leu Arg
            180                 185                 190

Gly Val Asn Pro Gly Glu Thr Pro Val Thr Cys Thr Ala Gly Val Gly
        195                 200                 205

Thr Phe Ile Leu Glu Phe Ser Thr Leu Ser Arg Leu Thr Gly Asp Pro
    210                 215                 220

Val Phe Glu Asn Val Ala Arg Lys Ala Leu Arg Ala Leu Trp Arg Thr
225                 230                 235                 240

Arg Ser Asp Ile Gly Leu Val Gly Asn His Ile Asp Val Ile Thr Ser
                245                 250                 255

Lys Trp Val Ala Gln Asp Ala Gly Ile Gly Ala Gly Val Asp Ser Tyr
            260                 265                 270

Phe Glu Tyr Leu Val Arg Gly Ala Ile Met Leu Gln Asp Glu Glu Leu
        275                 280                 285

Leu Thr Met Phe Tyr Glu Phe Asp Lys Ser Ile Lys Asn Tyr Thr Lys
    290                 295                 300

Phe Asp Asp Trp Tyr Leu Trp Val Gln Met His Lys Gly Thr Val Ser
305                 310                 315                 320

Met Pro Val Phe Gln Ser Leu Glu Ala Phe Trp Pro Gly Met Gln Ser
                325                 330                 335

Leu Ile Gly Asp Ile Ser Ser Ala Thr Lys Ser Phe His Asn Tyr Tyr
            340                 345                 350
```

```
Ser Val Trp Arg Gln Phe Gly Gly Leu Pro Glu Phe Tyr Ser Ile Pro
        355                 360                 365

Gln Gly Tyr Thr Val Asp Lys Arg Glu Gly Tyr Pro Leu Arg Pro Glu
    370                 375                 380

Leu Ile Glu Ser Ala Met Tyr Leu Tyr Lys Ala Thr Gly Asp Pro Ser
385                 390                 395                 400

Phe Ile Gln Leu Gly Arg Asp Ala Val Glu Ser Ile Asp Arg Ile Ser
                405                 410                 415

Arg Val Asn Cys Gly Phe Ala Thr Val Lys Asp Val Arg Asp His Lys
            420                 425                 430

Leu Asp Asn Arg Met Glu Ser Phe Phe Leu Ala Glu Thr Ile Lys Tyr
        435                 440                 445

Leu Tyr Leu Leu Phe Asp Pro Asp Asn Phe Leu His Asn Thr Gly Thr
    450                 455                 460

Glu Phe Glu Leu Gly Gly Leu Arg Gly Asp Cys Ile Leu Ser Ala Gly
465                 470                 475                 480

Gly Tyr Val Phe Asn Thr Glu Ala His Pro Leu Asp Pro Ala Ala Leu
                485                 490                 495

His Cys Cys Ser Arg Glu Gln Gln Asp Arg Arg Glu Ile Gln Asp Ile
            500                 505                 510

Leu Leu Ser Phe Ser Gln Pro His Thr Glu Glu Pro Ser Arg Asp Gln
        515                 520                 525

Ser Ala Gly Gly Ser Pro Glu Ser Ile Ala Leu Lys Pro Gly Glu Gln
    530                 535                 540

Arg Lys Ala Pro Val Leu Ser Cys Pro Thr Gln Pro Phe Ser Ala Lys
545                 550                 555                 560

Leu Ala Val Met Gly Gln Val Phe Ser Asp Asn Ser
                565                 570


<210> SEQ ID NO 8
<211> LENGTH: 579
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (12)..(12)
<223> OTHER INFORMATION: V or L
<220> FEATURE:
<221> NAME/KEY: MISC_FEATURE
<222> LOCATION: (14)..(14)
<223> OTHER INFORMATION: V or A
<220> FEATURE:
<221> NAME/KEY: MISC_FEATURE
<222> LOCATION: (15)..(15)
<223> OTHER INFORMATION: L or F
<220> FEATURE:
<221> NAME/KEY: MISC_FEATURE
<222> LOCATION: (26)..(26)
<223> OTHER INFORMATION: D or E
<220> FEATURE:
<221> NAME/KEY: MISC_FEATURE
<222> LOCATION: (28)..(28)
<223> OTHER INFORMATION: T or S
<220> FEATURE:
<221> NAME/KEY: MISC_FEATURE
<222> LOCATION: (57)..(57)
<223> OTHER INFORMATION: Y or F
<220> FEATURE:
<221> NAME/KEY: MISC_FEATURE
<222> LOCATION: (91)..(91)
<223> OTHER INFORMATION: T or V
<220> FEATURE:
<221> NAME/KEY: MISC_FEATURE
```

<222> LOCATION: (104)..(104)
<223> OTHER INFORMATION: N or S
<220> FEATURE:
<221> NAME/KEY: MISC_FEATURE
<222> LOCATION: (220)..(220)
<223> OTHER INFORMATION: V or L
<220> FEATURE:
<221> NAME/KEY: MISC_FEATURE
<222> LOCATION: (285)..(285)
<223> OTHER INFORMATION: K or R
<220> FEATURE:
<221> NAME/KEY: MISC_FEATURE
<222> LOCATION: (292)..(292)
<223> OTHER INFORMATION: H or R
<220> FEATURE:
<221> NAME/KEY: MISC_FEATURE
<222> LOCATION: (356)..(356)
<223> OTHER INFORMATION: P or A
<220> FEATURE:
<221> NAME/KEY: MISC_FEATURE
<222> LOCATION: (442)..(442)
<223> OTHER INFORMATION: H or D
<220> FEATURE:
<221> NAME/KEY: MISC_FEATURE
<222> LOCATION: (444)..(444)
<223> OTHER INFORMATION: N or T
<220> FEATURE:
<221> NAME/KEY: MISC_FEATURE
<222> LOCATION: (456)..(456)
<223> OTHER INFORMATION: S, T, or A
<220> FEATURE:
<221> NAME/KEY: MISC_FEATURE
<222> LOCATION: (458)..(458)
<223> OTHER INFORMATION: M or I
<220> FEATURE:
<221> NAME/KEY: MISC_FEATURE
<222> LOCATION: (461)..(461)
<223> OTHER INFORMATION: H or Y
<220> FEATURE:
<221> NAME/KEY: MISC_FEATURE
<222> LOCATION: (489)..(489)
<223> OTHER INFORMATION: R or Q
<220> FEATURE:
<221> NAME/KEY: MISC_FEATURE
<222> LOCATION: (502)..(502)
<223> OTHER INFORMATION: I or M
<220> FEATURE:
<221> NAME/KEY: MISC_FEATURE
<222> LOCATION: (503)..(503)
<223> OTHER INFORMATION: K or R
<220> FEATURE:
<221> NAME/KEY: MISC_FEATURE
<222> LOCATION: (505)..(505)
<223> OTHER INFORMATION: F or L
<220> FEATURE:
<221> NAME/KEY: MISC_FEATURE
<222> LOCATION: (506)..(506)
<223> OTHER INFORMATION: Y or H
<220> FEATURE:
<221> NAME/KEY: MISC_FEATURE
<222> LOCATION: (509)..(509)
<223> OTHER INFORMATION: K or R
<220> FEATURE:
<221> NAME/KEY: MISC_FEATURE
<222> LOCATION: (510)..(510)
<223> OTHER INFORMATION: Q or R
<220> FEATURE:
<221> NAME/KEY: MISC_FEATURE
<222> LOCATION: (513)..(513)
<223> OTHER INFORMATION: P or S
<220> FEATURE:
<221> NAME/KEY: MISC_FEATURE
<222> LOCATION: (514)..(516)
<223> OTHER INFORMATION: KRA, RA, or KF (one amino acid may be missing)
<220> FEATURE:
<221> NAME/KEY: MISC_FEATURE
<222> LOCATION: (518)..(518)
<223> OTHER INFORMATION: R or K
<220> FEATURE:

<221> NAME/KEY: MISC_FEATURE
<222> LOCATION: (519)..(519)
<223> OTHER INFORMATION: K or N
<220> FEATURE:
<221> NAME/KEY: MISC_FEATURE
<222> LOCATION: (522)..(522)
<223> OTHER INFORMATION: R or S
<220> FEATURE:
<221> NAME/KEY: MISC_FEATURE
<222> LOCATION: (529)..(529)
<223> OTHER INFORMATION: Q or P
<220> FEATURE:
<221> NAME/KEY: MISC_FEATURE
<222> LOCATION: (530)..(530)
<223> OTHER INFORMATION: S or A
<220> FEATURE:
<221> NAME/KEY: MISC_FEATURE
<222> LOCATION: (531)..(531)
<223> OTHER INFORMATION: G or R
<220> FEATURE:
<221> NAME/KEY: MISC_FEATURE
<222> LOCATION: (533)..(533)
<223> OTHER INFORMATION: A or G
<220> FEATURE:
<221> NAME/KEY: MISC_FEATURE
<222> LOCATION: (534)..(534)
<223> OTHER INFORMATION: T or S
<220> FEATURE:
<221> NAME/KEY: MISC_FEATURE
<222> LOCATION: (535)..(535)
<223> OTHER INFORMATION: L or P
<220> FEATURE:
<221> NAME/KEY: MISC_FEATURE
<222> LOCATION: (536)..(536)
<223> OTHER INFORMATION: S or F
<220> FEATURE:
<221> NAME/KEY: MISC_FEATURE
<222> LOCATION: (537)..(537)
<223> OTHER INFORMATION: S or A
<220> FEATURE:
<221> NAME/KEY: MISC_FEATURE
<222> LOCATION: (539)..(542)
<223> OTHER INFORMATION: AN, EN, GKQD, or ENHD (two amino acids may be
missing)
<220> FEATURE:
<221> NAME/KEY: MISC_FEATURE
<222> LOCATION: (544)..(544)
<223> OTHER INFORMATION: P or A
<220> FEATURE:
<221> NAME/KEY: MISC_FEATURE
<222> LOCATION: (547)..(547)
<223> OTHER INFORMATION: K or R
<220> FEATURE:
<221> NAME/KEY: MISC_FEATURE
<222> LOCATION: (548)..(548)
<223> OTHER INFORMATION: Q or K
<220> FEATURE:
<221> NAME/KEY: MISC_FEATURE
<222> LOCATION: (551)..(551)
<223> OTHER INFORMATION: Q, R, or K
<220> FEATURE:
<221> NAME/KEY: MISC_FEATURE
<222> LOCATION: (553)..(553)
<223> OTHER INFORMATION: R or K
<220> FEATURE:
<221> NAME/KEY: MISC_FEATURE
<222> LOCATION: (554)..(554)
<223> OTHER INFORMATION: T, A, or V

<400> SEQUENCE: 8

Met Pro Phe Arg Leu Leu Ile Pro Leu Gly Leu Xaa Cys Xaa Xaa Leu
1 5 10 15

Pro Leu His His Gly Ala Pro Gly Pro Xaa Gly Xaa Ala Pro Asp Pro
20 25 30

Ala His Tyr Arg Glu Arg Val Lys Ala Met Phe Tyr His Ala Tyr Asp
35 40 45

```
Ser Tyr Leu Glu Asn Ala Phe Pro Xaa Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Xaa Ser Glu Phe Gln Arg
                85                  90                  95

Val Val Glu Val Leu Gln Asp Xaa Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Xaa Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Xaa Ala Ile Arg
        275                 280                 285

Asn Tyr Thr Xaa Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Xaa Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe Xaa Pro Xaa Asn Phe Ile His
        435                 440                 445

Asn Asn Gly Ser Thr Phe Asp Xaa Val Xaa Thr Pro Xaa Gly Glu Cys
    450                 455                 460
```

```
Ile Leu Gly Ala Gly Gly Tyr Ile Phe Asn Thr Glu Ala His Pro Ile
465                 470                 475                 480

Asp Pro Ala Ala Leu His Cys Cys Xaa Arg Leu Lys Glu Glu Gln Trp
                485                 490                 495

Glu Val Glu Asp Leu Xaa Xaa Glu Xaa Xaa Ser Leu Xaa Xaa Ser Arg
            500                 505                 510

Xaa Xaa Xaa Xaa Gln Xaa Xaa Thr Val Xaa Ser Gly Pro Trp Glu Pro
        515                 520                 525

Xaa Xaa Xaa Pro Xaa Xaa Xaa Xaa Xaa Pro Xaa Xaa Xaa Xaa Gln Xaa
    530                 535                 540

Arg Glu Xaa Xaa Pro Ala Xaa Gln Xaa Xaa Pro Leu Leu Ser Cys Pro
545                 550                 555                 560

Ser Gln Pro Phe Thr Ser Lys Leu Ala Leu Leu Gly Gln Val Phe Leu
                565                 570                 575

Asp Ser Ser


<210> SEQ ID NO 9
<211> LENGTH: 371
<212> TYPE: PRT
<213> ORGANISM: Mus musculus

<400> SEQUENCE: 9

Met Val Val Val Ala Ala Ala Pro Ser Ala Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
            100                 105                 110

Arg Glu Lys Thr His Gly Leu Val Val Glu Asn Gln Glu Leu Arg Thr
        115                 120                 125

Arg Leu Gly Met Asp Thr Leu Asp Pro Asp Glu Val Pro Glu Val Glu
    130                 135                 140

Ala Lys Gly Ser Gly Val Arg Leu Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Ala Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Ser Leu Glu Glu Leu Pro Glu Val Tyr Pro Glu Gly Pro
    210                 215                 220

Ser Ser Leu Pro Ala Ser Leu Ser Leu Ser Val Gly Thr Ser Ser Ala
225                 230                 235                 240

Lys Leu Glu Ala Ile Asn Glu Leu Ile Arg Phe Asp His Val Tyr Thr
                245                 250                 255
```

```
Lys Pro Leu Val Leu Glu Ile Pro Ser Glu Thr Glu Ser Gln Thr Asn
            260                 265                 270

Val Val Val Lys Ile Glu Glu Ala Pro Leu Ser Ser Ser Glu Glu Asp
        275                 280                 285

His Pro Glu Phe Ile Val Ser Val Lys Lys Glu Pro Leu Glu Asp Asp
    290                 295                 300

Phe Ile Pro Glu Leu Gly Ile Ser Asn Leu Leu Ser Ser Ser His Cys
305                 310                 315                 320

Leu Arg Pro Pro Ser Cys Leu Leu Asp Ala His Ser Asp Cys Gly Tyr
                325                 330                 335

Glu Gly Ser Pro Ser Pro Phe Ser Asp Met Ser Ser Pro Leu Gly Thr
            340                 345                 350

Asp His Ser Trp Glu Asp Thr Phe Ala Asn Glu Leu Phe Pro Gln Leu
        355                 360                 365

Ile Ser Val
    370


<210> SEQ ID NO 10
<211> LENGTH: 369
<212> TYPE: PRT
<213> ORGANISM: Cricetulus griseus

<400> SEQUENCE: 10

Met Val Val Val Ala Ala Ser Pro Ser Ala Ala Thr Ala Ala Pro Lys
1               5                   10                  15

Val Leu Leu Leu Ser Gly Gln Pro Ala Ala Asp Gly Arg Ala Leu Pro
            20                  25                  30

Leu Met Val Pro Gly Ser Arg Ala Ala Gly Ser Glu Ala Asn Gly Ala
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Leu Leu Glu Asn Gln Leu Leu
            100                 105                 110

Arg Glu Lys Thr His Gly Leu Val Ile Glu Asn Gln Glu Leu Arg Thr
        115                 120                 125

Arg Leu Gly Met Asp Val Leu Thr Thr Glu Glu Ala Pro Glu Thr Glu
    130                 135                 140

Ser Lys Gly Asn Gly Val Arg Pro Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Asp Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Asn Leu Glu Glu Leu Pro Glu Val Tyr Pro Gly Pro Ser
    210                 215                 220

Ser Leu Pro Ala Ser Leu Ser Leu Ser Val Gly Thr Ser Ser Ala Lys
225                 230                 235                 240

Leu Glu Ala Ile Asn Glu Leu Ile Arg Phe Asp His Val Tyr Thr Lys
                245                 250                 255
```

```
Pro Leu Val Leu Glu Ile Pro Ser Glu Thr Glu Ser Gln Thr Asn Val
            260                 265                 270

Val Val Lys Ile Glu Glu Ala Pro Leu Ser Ser Ser Glu Glu Asp His
        275                 280                 285

Pro Glu Phe Ile Val Ser Val Lys Lys Glu Pro Glu Glu Asp Phe Ile
    290                 295                 300

Pro Glu Pro Gly Ile Ser Asn Leu Leu Ser Ser Ser His Cys Leu Lys
305                 310                 315                 320

Pro Ser Ser Cys Leu Leu Asp Ala Tyr Ser Asp Cys Gly Tyr Glu Gly
                325                 330                 335

Ser Pro Ser Pro Phe Ser Asp Met Ser Ser Pro Leu Gly Ile Asp His
            340                 345                 350

Ser Trp Glu Asp Thr Phe Ala Asn Glu Leu Phe Pro Gln Leu Ile Ser
        355                 360                 365

Val


<210> SEQ ID NO 11
<211> LENGTH: 376
<212> TYPE: PRT
<213> ORGANISM: Homo sapiens

<400> SEQUENCE: 11

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
        195                 200                 205

Lys Cys Pro Ser Pro Glu Pro Ala Ser Leu Glu Glu Leu Pro Glu Val
    210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255
```

```
Asp His Ile Tyr Thr Lys Pro Leu Val Leu Glu Ile Pro Ser Glu Thr
            260                 265                 270

Glu Ser Gln Ala Asn Val Val Val Lys Ile Glu Glu Ala Pro Leu Ser
        275                 280                 285

Pro Ser Glu Asn Asp His Pro Glu Phe Ile Val Ser Val Lys Glu Glu
    290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375


<210> SEQ ID NO 12
<211> LENGTH: 383
<212> TYPE: PRT
<213> ORGANISM: Danio rerio

<400> SEQUENCE: 12

Met Val Val Val Thr Ala Gly Thr Gly Gly Ala His Lys Val Leu Leu
1               5                   10                  15

Ile Ser Gly Lys Gln Ser Ala Ser Thr Gly Ala Thr Gln Gly Gly Tyr
            20                  25                  30

Ser Arg Ser Ile Ser Val Met Ile Pro Asn Gln Ala Ser Ser Asp Ser
        35                  40                  45

Asp Ser Thr Thr Ser Gly Pro Pro Leu Arg Lys Arg Gln Arg Leu Thr
    50                  55                  60

His Leu Ser Pro Glu Glu Lys Ala Leu Arg Arg Lys Leu Lys Asn Arg
65                  70                  75                  80

Val Ala Ala Gln Thr Ala Arg Asp Arg Lys Lys Ala Lys Met Gly Glu
                85                  90                  95

Leu Glu Gln Gln Val Leu Glu Leu Glu Leu Glu Asn Gln Lys Leu His
            100                 105                 110

Val Glu Asn Arg Leu Leu Arg Asp Lys Thr Ser Asp Leu Leu Ser Glu
        115                 120                 125

Asn Glu Glu Leu Arg Gln Arg Leu Gly Leu Asp Thr Leu Glu Thr Lys
    130                 135                 140

Glu Gln Val Gln Val Leu Glu Ser Ala Val Ser Asp Leu Gly Leu Val
145                 150                 155                 160

Thr Gly Ser Ser Glu Ser Ala Ala Gly Ala Gly Pro Ala Val Pro Lys
                165                 170                 175

Ser Glu Asp Phe Thr Met Asp Thr His Ser Pro Gly Pro Ala Asp Ser
            180                 185                 190

Glu Ser Asp Leu Leu Leu Gly Ile Leu Asp Ile Leu Asp Pro Glu Leu
        195                 200                 205

Phe Leu Lys Thr Asp Leu Pro Glu Ala Gln Glu Pro Gln Gln Glu Leu
    210                 215                 220

Val Leu Val Gly Gly Ala Gly Glu Gln Val Pro Ser Ser Ala Pro Ala
225                 230                 235                 240

Ala Leu Gly Pro Ala Pro Val Lys Leu Glu Ala Leu Asn Glu Leu Ile
```

```
                245                 250                 255

His Phe Asp His Ile Tyr Thr Lys Pro Ala Glu Val Leu Val Ser Glu
            260                 265                 270

Glu Ser Ile Cys Glu Val Lys Ala Glu Asp Ser Val Ala Phe Ser Glu
        275                 280                 285

Thr Glu Glu Glu Ile Gln Val Glu Asp Gln Thr Val Ser Val Lys Asp
    290                 295                 300

Glu Pro Glu Glu Val Val Ile Pro Ala Glu Asn Gln Asn Pro Asp Ala
305                 310                 315                 320

Ala Asp Asp Phe Leu Ser Asp Thr Ser Phe Gly Gly Tyr Glu Lys Ala
                325                 330                 335

Ser Tyr Leu Thr Asp Ala Tyr Ser Asp Ser Gly Tyr Glu Arg Ser Pro
            340                 345                 350

Ser Pro Phe Ser Asn Ile Ser Ser Pro Leu Cys Ser Glu Gly Ser Trp
        355                 360                 365

Asp Asp Met Phe Ala Ser Glu Leu Phe Pro Gln Leu Ile Ser Val
    370                 375                 380


<210> SEQ ID NO 13
<211> LENGTH: 373
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (7)..(7)
<223> OTHER INFORMATION: A or S
<220> FEATURE:
<221> NAME/KEY: MISC_FEATURE
<222> LOCATION: (9)..(9)
<223> OTHER INFORMATION: S or N
<220> FEATURE:
<221> NAME/KEY: MISC_FEATURE
<222> LOCATION: (10)..(10)
<223> OTHER INFORMATION: A or P
<220> FEATURE:
<221> NAME/KEY: MISC_FEATURE
<222> LOCATION: (12)..(12)
<223> OTHER INFORMATION: T or D
<220> FEATURE:
<221> NAME/KEY: MISC_FEATURE
<222> LOCATION: (13)..(13)
<223> OTHER INFORMATION: A or G
<220> FEATURE:
<221> NAME/KEY: MISC_FEATURE
<222> LOCATION: (14)..(14)
<223> OTHER INFORMATION: A or T
<220> FEATURE:
<221> NAME/KEY: MISC_FEATURE
<222> LOCATION: (26)..(26)
<223> OTHER INFORMATION: S or A
<220> FEATURE:
<221> NAME/KEY: MISC_FEATURE
<222> LOCATION: (27)..(27)
<223> OTHER INFORMATION: G, D, or A
<220> FEATURE:
<221> NAME/KEY: MISC_FEATURE
<222> LOCATION: (29)..(29)
<223> OTHER INFORMATION: R or Q
<220> FEATURE:
<221> NAME/KEY: MISC_FEATURE
<222> LOCATION: (37)..(37)
<223> OTHER INFORMATION: G or A
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
```

<222> LOCATION: (40)..(40)
<223> OTHER INFORMATION: A or G
<220> FEATURE:
<221> NAME/KEY: MISC_FEATURE
<222> LOCATION: (46)..(48)
<223> OTHER INFORMATION: S, N, or ASG (two amino acids may be missing)
<220> FEATURE:
<221> NAME/KEY: MISC_FEATURE
<222> LOCATION: (50)..(50)
<223> OTHER INFORMATION: T, A, or L
<220> FEATURE:
<221> NAME/KEY: MISC_FEATURE
<222> LOCATION: (105)..(105)
<223> OTHER INFORMATION: H or Q
<220> FEATURE:
<221> NAME/KEY: MISC_FEATURE
<222> LOCATION: (108)..(108)
<223> OTHER INFORMATION: Q or L
<220> FEATURE:
<221> NAME/KEY: MISC_FEATURE
<222> LOCATION: (123)..(123)
<223> OTHER INFORMATION: V or I
<220> FEATURE:
<221> NAME/KEY: MISC_FEATURE
<222> LOCATION: (130)..(130)
<223> OTHER INFORMATION: T or Q
<220> FEATURE:
<221> NAME/KEY: MISC_FEATURE
<222> LOCATION: (136)..(136)
<223> OTHER INFORMATION: T, V, or A
<220> FEATURE:
<221> NAME/KEY: MISC_FEATURE
<222> LOCATION: (138)..(138)
<223> OTHER INFORMATION: D, T, or V
<220> FEATURE:
<221> NAME/KEY: MISC_FEATURE
<222> LOCATION: (139)..(139)
<223> OTHER INFORMATION: P, T, or A
<220> FEATURE:
<221> NAME/KEY: MISC_FEATURE
<222> LOCATION: (140)..(140)
<223> OTHER INFORMATION: D or E
<220> FEATURE:
<221> NAME/KEY: MISC_FEATURE
<222> LOCATION: (142)..(142)
<223> OTHER INFORMATION: V, A, or none
<220> FEATURE:
<221> NAME/KEY: MISC_FEATURE
<222> LOCATION: (143)..(143)
<223> OTHER INFORMATION: P or none
<220> FEATURE:
<221> NAME/KEY: MISC_FEATURE
<222> LOCATION: (145)..(145)
<223> OTHER INFORMATION: V, T, or A
<220> FEATURE:
<221> NAME/KEY: MISC_FEATURE
<222> LOCATION: (147)..(147)
<223> OTHER INFORMATION: A or S
<220> FEATURE:
<221> NAME/KEY: MISC_FEATURE
<222> LOCATION: (150)..(150)
<223> OTHER INFORMATION: S or N
<220> FEATURE:
<221> NAME/KEY: MISC_FEATURE
<222> LOCATION: (151)..(151)
<223> OTHER INFORMATION: G or E
<220> FEATURE:
<221> NAME/KEY: MISC_FEATURE
<222> LOCATION: (154)..(154)
<223> OTHER INFORMATION: L or P
<220> FEATURE:
<221> NAME/KEY: MISC_FEATURE
<222> LOCATION: (171)..(171)
<223> OTHER INFORMATION: S or P
<220> FEATURE:
<221> NAME/KEY: MISC_FEATURE
<222> LOCATION: (180)..(180)
<223> OTHER INFORMATION: D or G
<220> FEATURE:

<221> NAME/KEY: MISC_FEATURE
<222> LOCATION: (181)..(181)
<223> OTHER INFORMATION: T or G
<220> FEATURE:
<221> NAME/KEY: MISC_FEATURE
<222> LOCATION: (182)..(182)
<223> OTHER INFORMATION: V or I
<220> FEATURE:
<221> NAME/KEY: MISC_FEATURE
<222> LOCATION: (183)..(183)
<223> OTHER INFORMATION: A or D
<220> FEATURE:
<221> NAME/KEY: MISC_FEATURE
<222> LOCATION: (198)..(198)
<223> OTHER INFORMATION: K or N
<220> FEATURE:
<221> NAME/KEY: MISC_FEATURE
<222> LOCATION: (212)..(212)
<223> OTHER INFORMATION: S or P
<220> FEATURE:
<221> NAME/KEY: MISC_FEATURE
<222> LOCATION: (214)..(214)
<223> OTHER INFORMATION: S or N
<220> FEATURE:
<221> NAME/KEY: MISC_FEATURE
<222> LOCATION: (224)..(224)
<223> OTHER INFORMATION: E or none
<220> FEATURE:
<221> NAME/KEY: MISC_FEATURE
<222> LOCATION: (256)..(256)
<223> OTHER INFORMATION: V or I
<220> FEATURE:
<221> NAME/KEY: MISC_FEATURE
<222> LOCATION: (273)..(273)
<223> OTHER INFORMATION: T or A
<220> FEATURE:
<221> NAME/KEY: MISC_FEATURE
<222> LOCATION: (286)..(286)
<223> OTHER INFORMATION: S or P
<220> FEATURE:
<221> NAME/KEY: MISC_FEATURE
<222> LOCATION: (289)..(289)
<223> OTHER INFORMATION: E or N
<220> FEATURE:
<221> NAME/KEY: MISC_FEATURE
<222> LOCATION: (300)..(300)
<223> OTHER INFORMATION: K or E
<220> FEATURE:
<221> NAME/KEY: MISC_FEATURE
<222> LOCATION: (303)..(303)
<223> OTHER INFORMATION: L, V, or none
<220> FEATURE:
<221> NAME/KEY: MISC_FEATURE
<222> LOCATION: (305)..(305)
<223> OTHER INFORMATION: D or E
<220> FEATURE:
<221> NAME/KEY: MISC_FEATURE
<222> LOCATION: (307)..(307)
<223> OTHER INFORMATION: F or L
<220> FEATURE:
<221> NAME/KEY: MISC_FEATURE
<222> LOCATION: (308)..(308)
<223> OTHER INFORMATION: I or V
<220> FEATURE:
<221> NAME/KEY: MISC_FEATURE
<222> LOCATION: (311)..(311)
<223> OTHER INFORMATION: L or P
<220> FEATURE:
<221> NAME/KEY: MISC_FEATURE
<222> LOCATION: (323)..(323)
<223> OTHER INFORMATION: L or P
<220> FEATURE:
<221> NAME/KEY: MISC_FEATURE
<222> LOCATION: (324)..(324)
<223> OTHER INFORMATION: R or K
<220> FEATURE:
<221> NAME/KEY: MISC_FEATURE
<222> LOCATION: (326)..(326)
<223> OTHER INFORMATION: P or S <220> FEATURE:
<221> NAME/KEY: MISC_FEATURE
<222> LOCATION: (333)..(333)
<223> OTHER INFORMATION: H or Y
<220> FEATURE:
<221> NAME/KEY: MISC_FEATURE
<222> LOCATION: (339)..(339)
<223> OTHER INFORMATION: E or G
<220> FEATURE:
<221> NAME/KEY: MISC_FEATURE
<222> LOCATION: (342)..(342)
<223> OTHER INFORMATION: P or L
<220> FEATURE:
<221> NAME/KEY: MISC_FEATURE
<222> LOCATION: (351)..(351)
<223> OTHER INFORMATION: P or L
<220> FEATURE:
<221> NAME/KEY: MISC_FEATURE
<222> LOCATION: (354)..(354)
<223> OTHER INFORMATION: T, I, or V
<220> FEATURE:
<221> NAME/KEY: MISC_FEATURE
<222> LOCATION: (355)..(355)
<223> OTHER INFORMATION: D or N

<400> SEQUENCE: 13

Met Val Val Val Ala Ala Xaa Pro Xaa Xaa Ala Xaa Xaa Xaa Pro Lys
1 5 10 15

Val Leu Leu Leu Ser Gly Gln Pro Ala Xaa Xaa Gly Xaa Ala Leu Pro
20 25 30

Leu Met Val Pro Xaa Xaa Arg Xaa Ala Gly Ser Glu Ala Xaa Xaa Xaa
35 40 45

Gly Xaa Pro Gln Ala Arg Lys Arg Gln Arg Leu Thr His Leu Ser Pro
50 55 60

Glu Glu Lys Ala Leu Arg Arg Lys Leu Lys Asn Arg Val Ala Ala Gln
65 70 75 80

Thr Ala Arg Asp Arg Lys Lys Ala Arg Met Ser Glu Leu Glu Gln Gln
85 90 95

Val Val Asp Leu Glu Glu Glu Asn Xaa Lys Leu Xaa Leu Glu Asn Gln
100 105 110

Leu Leu Arg Glu Lys Thr His Gly Leu Val Xaa Glu Asn Gln Glu Leu
115 120 125

Arg Xaa Arg Leu Gly Met Asp Xaa Leu Xaa Xaa Xaa Glu Xaa Xaa Glu
130 135 140

Xaa Glu Xaa Lys Gly Xaa Xaa Val Arg Xaa Val Ala Gly Ser Ala Glu
145 150 155 160

Ser Ala Ala Gly Ala Gly Pro Val Val Thr Xaa Pro Glu His Leu Pro
165 170 175

Met Asp Ser Xaa Xaa Xaa Xaa Ser Ser Asp Ser Glu Ser Asp Ile Leu
180 185 190

Leu Gly Ile Leu Asp Xaa Leu Asp Pro Val Met Phe Phe Lys Cys Pro
195 200 205

Ser Pro Glu Xaa Ala Xaa Leu Glu Glu Leu Pro Glu Val Tyr Pro Xaa
210 215 220

Gly Pro Ser Ser Leu Pro Ala Ser Leu Ser Leu Ser Val Gly Thr Ser
225 230 235 240

Ser Ala Lys Leu Glu Ala Ile Asn Glu Leu Ile Arg Phe Asp His Xaa
245 250 255

Tyr Thr Lys Pro Leu Val Leu Glu Ile Pro Ser Glu Thr Glu Ser Gln
260 265 270

Xaa Asn Val Val Val Lys Ile Glu Glu Ala Pro Leu Ser Xaa Ser Glu

```
        275                 280                 285

Xaa Asp His Pro Glu Phe Ile Val Ser Val Lys Xaa Glu Pro Xaa Glu
    290                 295                 300

Xaa Asp Xaa Xaa Pro Glu Xaa Gly Ile Ser Asn Leu Leu Ser Ser Ser
305                 310                 315                 320

His Cys Xaa Xaa Pro Xaa Ser Cys Leu Leu Asp Ala Xaa Ser Asp Cys
                325                 330                 335

Gly Tyr Xaa Gly Ser Xaa Ser Pro Phe Ser Asp Met Ser Ser Xaa Leu
            340                 345                 350

Gly Xaa Xaa His Ser Trp Glu Asp Thr Phe Ala Asn Glu Leu Phe Pro
        355                 360                 365

Gln Leu Ile Ser Val
    370


<210> SEQ ID NO 14
<211> LENGTH: 7686
<212> TYPE: DNA
<213> ORGANISM: Artificial
<220> FEATURE:
<223> OTHER INFORMATION: Synthetic plasmid

<400> SEQUENCE: 14

aagcttatac tcgagctcta gattgggaac ccgggtctct cgaattcgat gccttttaga     60

ctcctgatac cattgggtct tgtttgcgtt ctcctccctc tccatcacgg cgccccaggt    120

ccagacggta ccgcacctga tcctgcccat taccgcgaac gcgttaaagc catgttctac    180

cacgcctatg actcctatct ggaaaatgca ttcccctatg atgagctccg acccccttacc    240

tgcgatggtc atgatacttg gggctctttt tcccttaccc ttattgacgc tctggacaca    300

ctccttatcc tcggaaacac cagcgaattt caaagagtag ttgaagtact tcaggacaat    360

gtcgactttg acatcgatgt gaacgcatca gttttcgaaa caaatataag agtcgttgga    420

ggtctgctct ccgcccacct tctctctaaa aaagccggag tagaagttga agctggctgg    480

ccctgctccg gacccctcct tcgtatggct gaagaagctg cccgcaaact ccttcccgct    540

tttcagaccc caaccggtat gccctatggt actgttaacc tcctgcacgg agtaaatccc    600

ggcgaaaccc ccgtcacatg tacagccgga attggaacct ttattgtgga atttgcaacc    660

cttagcagcc tgaccggaga tcctgtattc gaagacgtgg ctcgggttgc cctgatgcga    720

ctgtgggaat ccaggtctga tatcggtctg gtcggtaacc atatagacgt actcactggt    780

aaatgggttg cacaagacgc tggaattggg gcaggcgtgg attcttattt tgaatatctc    840

gtaaaagggg ccatactctt gcaggacaaa aaacttatgg ctatgttcct ggaatataac    900

aaagctatta ggaactacac acacttcgat gattggtatt tgtgggtcca aatgtataaa    960

ggaaccgttt ctatgcctgt ctttcagtca ctggaggctt attggcctgg tctgcaatcc   1020

ctgatcggag acattgacaa tgcaatgagg acattcctta attattacac tgtttggaag   1080

cagttcggcg gattgcccga attttacaac attcctcaag gctatacagt tgaaaaaaga   1140

gaaggatatc ccctgcgccc cgagcttatt gaaagcgcta tgtatctgta tcgtgcaaca   1200

ggtgatccaa ccctgcttga actgggacga gacgccgtcg aatcaatcga gaaaatttca   1260

aaagtggaat gcggctttgc aacaattaaa gatcttagag accacaaact ggataatcgc   1320

atggagtcat tctttttggc tgagaccgtc aagtatctgt atctgctttt tcatcccaac   1380

aacttcatcc ataataacgg gtccaccttc gattcagtca tgacccctca cggtgaatgc   1440

atactcggag ctggaggcta tatttttaac actgaagctc acccaattga cccagctgcc   1500
```

```
cttcattgtt gtcgacgtct gaaagaagaa caatgggagg ttgaagattt gatcaaagaa   1560
ttttactcac ttaaacaaag tcgacctaaa cgcgcacaga gaaaaactgt aagatctggt   1620
ccttgggaac ctcagtccgg cccagcaact ctttcatccc ccgccaacca accacgagaa   1680
aaacaaccag cccaacagag aaccccccctg ctcagctgcc cctctcagcc cttcacttca   1740
aaactcgccc tgcttggaca ggtgtttctg gactcctctt gatttaaaca cgcggccgct   1800
aatcagccat accacatttg tagaggtttt acttgcttta aaaaacctcc cacacctccc   1860
cctgaacctg aaacataaaa tgaatgcaat tgttgttgtt aacttgttta ttgcagctta   1920
taatggttac aaataaagca atagcatcac aaatttcaca aataaagcat ttttttcact   1980
gcattctagt tgtggtttgt ccaaactcat caatgtatct tatcatgtct accggtaggg   2040
cccctctctt catgtgagca aaaggccagc aaaaggccag gaaccgtaaa aaggccgcgt   2100
tgctggcgtt tttccatagg ctccgccccc ctgacgagca tcacaaaaat cgacgctcaa   2160
gtcagaggtg gcgaaacccg acaggactat aaagatacca ggcgtttccc cctggaagct   2220
ccctcgtgcg ctctcctgtt ccgaccctgc cgcttaccgg atacctgtcc gcctttctcc   2280
cttcgggaag cgtggcgctt tctcaatgct cacgctgtag gtatctcagt tcggtgtagg   2340
tcgttcgctc caagctgggc tgtgtgcacg aaccccccgt tcagcccgac cgctgcgcct   2400
tatccggtaa ctatcgtctt gagtccaacc cggtaagaca cgacttatcg ccactggcag   2460
cagccactgg taacaggatt agcagagcga ggtatgtagg cggtgctaca gagttcttga   2520
agtggtggcc taactacggc tacactagaa ggacagtatt tggtatctgc gctctgctga   2580
agccagttac cttcggaaaa agagttggta gctcttgatc cggcaaacaa accaccgctg   2640
gtagcggtgg tttttttgtt tgcaagcagc agattacgcg cagaaaaaaa ggatctcaag   2700
aagatccttt gatcttttct acggggtctg acgctcagtg gaacgaaaac tcacgttaag   2760
ggattttggt catgggcgcg cctcatactc ctgcaggcat gagattatca aaaaggatct   2820
tcacctagat ccttttaaat taaaaatgaa gttttaaatc aatctaaagt atatatgagt   2880
aaacttggtc tgacagttac caatgcttaa tcagtgaggc acctatctca gcgatctgtc   2940
tatttcgttc atccatagtt gcctgactcc ccgtcgtgta gataactacg atacgggagg   3000
gcttaccatc tggccccagt gctgcaatga taccgcgaga cccacgctca ccggctccag   3060
atttatcagc aataaaccag ccagccggaa gggccgagcg cagaagtggt cctgcaactt   3120
tatccgcctc catccagtct attaattgtt gccgggaagc tagagtaagt agttcgccag   3180
ttaatagttt gcgcaacgtt gttgccattg ctacaggcat cgtggtgtca cgctcgtcgt   3240
ttggtatggc ttcattcagc tccggttccc aacgatcaag gcgagttaca tgatccccca   3300
tgttgtgcaa aaaagcggtt agctccttcg gtcctccgat cgttgtcaga agtaagttgg   3360
ccgcagtgtt atcactcatg gttatggcag cactgcataa ttctcttact gtcatgccat   3420
ccgtaagatg cttttctgtg actggtgagt actcaaccaa gtcattctga gaatagtgta   3480
tgcggcgacc gagttgctct tgcccggcgt caatacggga taataccgcg ccacatagca   3540
gaactttaaa agtgctcatc attggaaaac gttcttcggg gcgaaaactc tcaaggatct   3600
taccgctgtt gagatccagt tcgatgtaac ccactcgtgc acccaactga tcttcagcat   3660
cttttacttt caccagcgtt tctgggtgag caaaaacagg aaggcaaaat gccgcaaaaa   3720
agggaataag ggcgacacgg aaatgttgaa tactcatact cttccttttt caatattatt   3780
gaagcattta tcagggttat tgtctcatga gcggatacat atttgaatgt atttagaaaa   3840
```

```
ataaacaaat aggggttccg cgcacatttc cccgaaaagt gccacctgac gtcaggtacc   3900
aagcctaggc ctccaaaaaa gcctcctcac tacttctgga atagctcaga ggcagaggcg   3960
gcctcggcct ctgcataaat aaaaaaaatt agtcagccat ggggcggaga atgggcggaa   4020
ctgggcggag ttaggggcgg gatgggcgga gttaggggcg ggactatggt tgctgactaa   4080
ttgagatgca tgctttgcat acttctgcct gctggggagc ctggggactt tccacacctg   4140
gttgctgact aattgagatg catgctttgc atacttctgc ctgctgggga gcctggggac   4200
tttccacacc ggatccacca tgggatcggc cattgaacaa gatggattgc acgcaggttc   4260
tccggccgct tgggtggaga ggctattcgg ctatgactgg gcacaacaga caatcggctg   4320
ctctgatgcc gccgtgttcc ggctgtcagc gcaggggcgc ccggttcttt ttgtcaagac   4380
cgacctgtcc ggtgccctga atgaactgca ggacgaggca gcgcggctat cgtggctggc   4440
cacgacgggc gttccttgcg cagctgtgct cgacgttgtc actgaagcgg gaagggactg   4500
gctgctattg ggcgaagtgc cggggcagga tctcctgtca tctcaccttg ctcctgccga   4560
gaaagtatcc atcatggctg atgcaatgcg gcggctgcat acgcttgatc cggctacctg   4620
cccattcgac caccaagcga aacatcgcat cgagcgagca cgtactcgga tggaagccgg   4680
tcttgtcgat caggatgatc tggacgaaga gcatcagggg ctcgcgccag ccgaactgtt   4740
cgccaggctc aaggcgcgca tgcccgacgg cgatgatctc gtcgtgaccc atggcgatgc   4800
ctgcttgccg aatatcatgg tggaaaatgg ccgcttttct ggattcatcg actgtggccg   4860
gctgggtgtg gcggaccgct atcaggacat agcgttggct acccgtgata ttgctgaaga   4920
gcttggcggc gaatgggctg accgcttcct cgtgctttac ggtatcgccg ctcccgattc   4980
gcagcgcatc gccttctatc gccttcttga cgagttcttc tgaacgcgtg ctgtaagtct   5040
gcagaaattg atgatctatt aaacaataaa gatgtccact aaaatggaag tttttcctgt   5100
catactttgt taagaagggt gagaacagag tacctacatt ttgaatggaa ggattggagc   5160
tacgggggtg ggggtggggt gggattagat aaatgcctgc tctttactga aggctcttta   5220
ctattgcttt atgataatgt ttcatagttg gatatcataa tttaaacaag caaaaccaaa   5280
ttaagggcca gctcattcct cccactcatg atctatggat ctatagatct ctcgtgcagc   5340
tggggctcta gggggtatcc ccacgcgccc tgtagcggcg cattaagcgc ggcgggtgtg   5400
gtggttacgc gcagcgtgac cgctacactt gccagcgccc tagcgcccgc tcctttcgct   5460
ttcttccctt cctttctcgc cacgttcgcc ggctttcccc gtcaagctct aaatcggggg   5520
ctccctttag ggttccgatt tagtgcttta cggcacctcg accccaaaaa acttgattag   5580
ggtgatggtt cacgtagtgg gccatcgccc tgatagacgg tttttcgccc tttgacgttg   5640
gagtccacgt tctttaatag tggactcttg ttccaaactg gaacaacact caaccctatc   5700
tcggtctatt cttttgattt ataagggatt ttgccgattt cggcctattg gttaaaaaat   5760
gagctgattt aacaaaaatt taacgcgaat taattctgtg gaatgtgtgt cagttagtcg   5820
cgaggcctcc gcgccgggtt ttggcgcctc ccgcgggcgc ccccctcctc acggcgagcg   5880
ctgccacgtc agacgaaggg cgcagcgagc gtcctgatcc ttccgcccgg acgctcagga   5940
cagcggcccg ctgctcataa gactcggcct tagaacccca gtatcagcag aaggacattt   6000
taggacggga cttgggtgac tctagggcac tggttttctt tccagagagc ggaacaggcg   6060
aggaaaagta gtcccttctc ggcgattctg cggagggatc tccgtggggc ggtgaacgcc   6120
gatgattata taaggacgcg ccgggtgtgg cacagctagt tccgtcgcag ccgggatttg   6180
ggtcgcggtt cttgtttgtg gatcgctgtg atcgtcactt ggtgagtagc gggctgctgg   6240
```

```
gctggccggg gctttcgtgg ccgccgggcc gctcggtggg acggaagcgt gtggagagac   6300
cgccaagggc tgtagtctgg gtccgcgagc aaggttgccc tgaactgggg gttgggggga   6360
gcgcagcaaa atggcggctg ttcccgagtc ttgaatggaa gacgcttgtg aggcgggctg   6420
tgaggtcgtt gaaacaaggt ggggggcatg gtgggcggca agaacccaag gtcttgaggc   6480
cttcgctaat gcgggaaagc tcttattcgg gtgagatggg ctggggcacc atctggggac   6540
cctgacgtga agtttgtcac tgactggaga actcggtttg tcgtctgttg cgggggcggc   6600
agttatggcg gtgccgttgg gcagtgcacc cgtacctttg ggagcgcgcg ccctcgtcgt   6660
gtcgtgacgt cacccgttct gttggcttat aatgcagggt ggggccacct gccggtaggt   6720
gtgcggtagg cttttctccg tcgcaggacg cagggttcgg gcctagggta ggctctcctg   6780
aatcgacagg cgccggacct ctggtgaggg gagggataag tgaggcgtca gtttctttgg   6840
tcggttttat gtacctatct tcttaagtag ctgaagctcc ggttttgaac tatgcgctcg   6900
gggttggcga gtgtgttttg tgaagttttt taggcacctt ttgaaatgta atcatttggg   6960
tcaatatgta attttcagtg ttagactagt aaattgtccg ctaaattctg gccgtttttg   7020
gctttttgt tagacgtcga ccgatcctga gaacttcagg gtgagtttgg ggacccttga   7080
ttgttctttc tttttcgcta ttgtaaaatt catgttatat ggagggggca aagttttcag   7140
ggtgttgttt agaatgggaa gatgtccctt gtatcaccat ggaccctcat gataattttg   7200
tttctttcac tttctactct gttgacaacc attgtctcct cttattttct tttcattttc   7260
tgtaactttt tcgttaaact ttagcttgca tttgtaacga atttttaaat tcacttttgt   7320
ttatttgtca gattgtaagt actttctcta atcacttttt tttcaaggca atcagggtat   7380
attatattgt acttcagcac agttttagag aacaattgtt ataattaaat gataaggtag   7440
aatatttctg catataaatt ctggctggcg tggaaatatt cttattggta gaaacaacta   7500
caccctggtc atcatcctgc ctttctcttt atggttacaa tgatatacac tgtttgagat   7560
gaggataaaa tactctgagt ccaaaccggg cccctctgct aaccatgttc atgccttctt   7620
ctctttccta cagctcctgg gcaacgtgct ggttgttgtg ctgtctcatc attttggcaa   7680
agaatt                                                              7686
```

<210> SEQ ID NO 15
<211> LENGTH: 7257
<212> TYPE: DNA
<213> ORGANISM: Artificial
<220> FEATURE:
<223> OTHER INFORMATION: Synthetic plasmid

<400> SEQUENCE: 15

```
aagcttatac tcgagctcta gattgggaac ccgggtctct cgaattcgat gccttttaga     60
ctcctgatac cattgggtct tgtttgcgtt ctcctccctc tccatcacgg cgccccaggt    120
ccagacggta ccgcacctga tcctgcccat taccgcgaac gcgttaaagc catgttctac    180
cacgcctatg actcctatct ggaaaatgca ttcccctatg atgagctccg acccccttacc    240
tgcgatggtc atgatacttg gggctctttt tcccttaccc ttattgacgc tctggacaca    300
ctccttatcc tcggaaacac cagcgaattt caaagagtag ttgaagtact tcaggacaat    360
gtcgactttg acatcgatgt gaacgcatca gttttcgaaa caaatataag agtcgttgga    420
ggtctgctct ccgcccacct tctctctaaa aaagccggag tagaagttga agctggctgg    480
ccctgctccg gacccctcct tcgtatggct gaagaagctg cccgcaaact ccttcccgct    540
```

```
tttcagaccc caaccggtat gccctatggt actgttaacc tcctgcacgg agtaaatccc    600
ggcgaaaccc ccgtcacatg tacagccgga attggaacct ttattgtgga atttgcaacc    660
cttagcagcc tgaccggaga tcctgtattc gaagacgtgg ctcgggttgc cctgatgcga    720
ctgtgggaat ccaggtctga tatcggtctg gtcggtaacc atatagacgt actcactggt    780
aaatgggttg cacaagacgc tggaattggg gcaggcgtgg attcttattt tgaatatctc    840
gtaaaagggg ccatactctt gcaggacaaa aaacttatgg ctatgttcct ggaatataac    900
aaagctatta ggaactacac acacttcgat gattggtatt tgtgggtcca aatgtataaa    960
ggaaccgttt ctatgcctgt ctttcagtca ctggaggctt attggcctgg tctgcaatcc   1020
ctgatcggag acattgacaa tgcaatgagg acattcctta attattacac tgtttggaag   1080
cagttcggcg gattgcccga attttacaac attcctcaag gctatacagt tgaaaaaaga   1140
gaaggatatc ccctgcgccc cgagcttatt gaaagcgcta tgtatctgta tcgtgcaaca   1200
ggtgatccaa ccctgcttga actgggacga gacgccgtcg aatcaatcga gaaaatttca   1260
aaagtggaat gcggctttgc aacaattaaa gatcttagag accacaaact ggataatcgc   1320
atggagtcat tctttttggc tgagaccgtc aagtatctgt atctgctttt tcatcccaac   1380
aacttcatcc ataataacgg gtccaccttc gattcagtca tgacccctca cggtgaatgc   1440
atactcggag ctggaggcta tatttttaac actgaagctc acccaattga cccagctgcc   1500
cttcattgtt gtcgacgtct gaaagaagaa caatgggagg ttgaagattt gatcaaagaa   1560
ttttactcac ttaaacaaag tcgacctaaa cgcgcacaga gaaaaactgt aagatctggt   1620
ccttgggaac ctcagtccgg cccagcaact ctttcatccc ccgccaacca accacgagaa   1680
aaacaaccag cccaacagag aaccccccctg ctcagctgcc cctctcagcc cttcacttca   1740
aaactcgccc tgcttggaca ggtgtttctg gactcctctt gatttaaaca cgcggccgct   1800
aatcagccat accacatttg tagaggtttt acttgcttta aaaaacctcc cacacctccc   1860
cctgaacctg aaacataaaa tgaatgcaat tgttgttgtt aacttgttta ttgcagctta   1920
taatggttac aaataaagca atagcatcac aaatttcaca aataaagcat ttttttcact   1980
gcattctagt tgtggtttgt ccaaactcat caatgtatct tatcatgtct accggtaggg   2040
cccctctctt catgtgagca aaaggccagc aaaaggccag gaaccgtaaa aaggccgcgt   2100
tgctggcgtt tttccatagg ctccgccccc ctgacgagca tcacaaaaat cgacgctcaa   2160
gtcagaggtg gcgaaacccg acaggactat aaagatacca ggcgtttccc cctggaagct   2220
ccctcgtgcg ctctcctgtt ccgaccctgc cgcttaccgg atacctgtcc gcctttctcc   2280
cttcgggaag cgtggcgctt tctcatagct cacgctgtag gtatctcagt tcggtgtagg   2340
tcgttcgctc caagctgggc tgtgtgcacg aaccccccgt tcagcccgac cgctgcgcct   2400
tatccggtaa ctatcgtctt gagtccaacc cggtaagaca cgacttatcg ccactggcag   2460
cagccactgg taacaggatt agcagagcga ggtatgtagg cggtgctaca gagttcttga   2520
agtggtggcc taactacggc tacactagaa ggacagtatt tggtatctgc gctctgctga   2580
agccagttac cttcggaaaa agagttggta gctcttgatc cggcaaacaa accaccgctg   2640
gtagcggtgg tttttttgtt tgcaagcagc agattacgcg cagaaaaaaa ggatctcaag   2700
aagatccttt gatcttttct acggggtctg acgctcagtg gaacgaaaac tcacgttaag   2760
ggattttggt catgggcgcg cctcatactc ctgcaggcat gagattatca aaaaggatct   2820
tcacctagat ccttttaaat taaaaatgaa gttttaaatc aatctaaagt atatatgagt   2880
aaacttggtc tgacagttac caatgcttaa tcagtgaggc acctatctca gcgatctgtc   2940
```

```
tatttcgttc atccatagtt gcctgactcc ccgtcgtgta gataactacg atacgggagg   3000
gcttaccatc tggccccagt gctgcaatga taccgcgaga cccacgctca ccggctccag   3060
atttatcagc aataaaccag ccagccggaa gggccgagcg cagaagtggt cctgcaactt   3120
tatccgcctc catccagtct attaattgtt gccgggaagc tagagtaagt agttcgccag   3180
ttaatagttt gcgcaacgtt gttgccattg ctacaggcat cgtggtgtca cgctcgtcgt   3240
ttggtatggc ttcattcagc tccggttccc aacgatcaag gcgagttaca tgatccccca   3300
tgttgtgcaa aaaagcggtt agctccttcg gtcctccgat cgttgtcaga agtaagttgg   3360
ccgcagtgtt atcactcatg gttatggcag cactgcataa ttctcttact gtcatgccat   3420
ccgtaagatg cttttctgtg actggtgagt actcaaccaa gtcattctga gaatagtgta   3480
tgcggcgacc gagttgctct tgcccggcgt caatacggga taataccgcg ccacatagca   3540
gaactttaaa agtgctcatc attggaaaac gttcttcggg gcgaaaactc tcaaggatct   3600
taccgctgtt gagatccagt tcgatgtaac ccactcgtgc acccaactga tcttcagcat   3660
cttttacttt caccagcgtt tctgggtgag caaaaacagg aaggcaaaat gccgcaaaaa   3720
agggaataag ggcgacacgg aaatgttgaa tactcatact cttccttttt caatattatt   3780
gaagcattta tcagggttat tgtctcatga gcggatacat atttgaatgt atttagaaaa   3840
ataaacaaat aggggttccg cgcacatttc cccgaaaagt gccacctgac gtcaggtacc   3900
aagcctaggc ctccaaaaaa gcctcctcac tacttctgga atagctcaga ggcagaggcg   3960
gcctcggcct ctgcataaat aaaaaaaatt agtcagccat ggggcggaga atgggcggaa   4020
ctgggcggag ttaggggcgg gatgggcgga gttaggggcg ggactatggt tgctgactaa   4080
ttgagatgca tgctttgcat acttctgcct gctggggagc ctggggactt tccacacctg   4140
gttgctgact aattgagatg catgctttgc atacttctgc ctgctgggga gcctggggac   4200
tttccacacc ggatccacca tggccaagtt gaccagtgcc gttccggtgc tcaccgcgcg   4260
cgacgtcgcc ggagcggtcg agttctggac cgaccggctc gggttctccc gggacttcgt   4320
ggaggacgac ttcgccggtg tggtccggga cgacgtgacc ctgttcatca gcgcggtcca   4380
ggaccaggtg gtgccggaca acaccctggc ctgggtgtgg gtgcgcggcc tggacgagct   4440
gtacgccgag tggtcggagg tcgtgtccac gaacttccgg gacgcctccg ggccggccat   4500
gaccgagatc ggcgagcagc cgtgggggcg ggagttcgcc ctgcgcgacc cggccggcaa   4560
ctgcgtgcac ttcgtggccg aggagcagga ctgaacgcgt gctgtaagtc tgcagaaatt   4620
gatgatctat taaacaataa agatgtccac taaaatggaa gtttttcctg tcatactttg   4680
ttaagaaggg tgagaacaga gtacctacat tttgaatgga aggattggag ctacgggggt   4740
gggggtgggg tgggattaga taaatgcctg ctctttactg aaggctcttt actattgctt   4800
tatgataatg tttcatagtt ggatatcata atttaaacaa gcaaaaccaa attaagggcc   4860
agctcattcc tcccactcat gatctatgga tctatagatc tctcgtgcag ctggggctct   4920
agggggtatc cccacgcgcc ctgtagcggc gcattaagcg cggcgggtgt ggtggttacg   4980
cgcagcgtga ccgctacact tgccagcgcc ctagcgcccg ctcctttcgc tttcttccct   5040
tcctttctcg ccacgttcgc cggctttccc cgtcaagctc taaatcgggg gctcccttta   5100
gggttccgat ttagtgcttt acggcacctc gaccccaaaa aacttgatta gggtgatggt   5160
tcacgtagtg ggccatcgcc ctgatagacg gtttttcgcc ctttgacgtt ggagtccacg   5220
ttctttaata gtggactctt gttccaaact ggaacaacac tcaaccctat ctcggtctat   5280
```

```
tcttttgatt tataagggat tttgccgatt tcggcctatt ggttaaaaaa tgagctgatt   5340
taacaaaaat ttaacgcgaa ttaattctgt ggaatgtgtg tcagttagtc gcgaggcctc   5400
cgcgccgggt tttggcgcct cccgcgggcg ccccccctcct cacggcgagc gctgccacgt   5460
cagacgaagg gcgcagcgag cgtcctgatc cttccgcccg gacgctcagg acagcggccc   5520
gctgctcata agactcggcc ttagaacccc agtatcagca gaaggacatt ttaggacggg   5580
acttgggtga ctctagggca ctggttttct ttccagagag cggaacaggc gaggaaaagt   5640
agtcccttct cggcgattct gcggagggat ctccgtgggg cggtgaacgc cgatgattat   5700
ataaggacgc gccgggtgtg gcacagctag ttccgtcgca gccgggattt gggtcgcggt   5760
tcttgtttgt ggatcgctgt gatcgtcact tggtgagtag cgggctgctg ggctggccgg   5820
ggctttcgtg gccgccgggc cgctcggtgg gacggaagcg tgtggagaga ccgccaaggg   5880
ctgtagtctg ggtccgcgag caaggttgcc ctgaactggg ggttgggggg agcgcagcaa   5940
aatggcggct gttcccgagt cttgaatgga agacgcttgt gaggcgggct gtgaggtcgt   6000
tgaaacaagg tgggggcat ggtgggcggc aagaacccaa ggtcttgagg ccttcgctaa   6060
tgcgggaaag ctcttattcg ggtgagatgg gctggggcac catctgggga ccctgacgtg   6120
aagtttgtca ctgactggag aactcggttt gtcgtctgtt gcgggggcgg cagttatggc   6180
ggtgccgttg ggcagtgcac ccgtaccttt gggagcgcgc gccctcgtcg tgtcgtgacg   6240
tcacccgttc tgttggctta taatgcaggg tggggccacc tgccggtagg tgtgcggtag   6300
gcttttctcc gtcgcaggac gcagggttcg ggcctagggt aggctctcct gaatcgacag   6360
gcgccggacc tctggtgagg ggagggataa gtgaggcgtc agtttctttg gtcggtttta   6420
tgtacctatc ttcttaagta gctgaagctc cggttttgaa ctatgcgctc ggggttggcg   6480
agtgtgtttt gtgaagtttt ttaggcacct tttgaaatgt aatcatttgg gtcaatatgt   6540
aattttcagt gttagactag taaattgtcc gctaaattct ggccgttttt ggctttttg   6600
ttagacgtcg accgatcctg agaacttcag ggtgagtttg gggacccttg attgttcttt   6660
ctttttcgct attgtaaaat tcatgttata tggagggggc aaagttttca gggtgttgtt   6720
tagaatggga agatgtccct tgtatcacca tggaccctca tgataatttt gtttctttca   6780
ctttctactc tgttgacaac cattgtctcc tcttattttc ttttcatttt ctgtaacttt   6840
ttcgttaaac tttagcttgc atttgtaacg aatttttaaa ttcacttttg tttatttgtc   6900
agattgtaag tactttctct aatcactttt ttttcaaggc aatcagggta tattatattg   6960
tacttcagca cagttttaga gaacaattgt tataattaaa tgataaggta gaatatttct   7020
gcatataaat tctggctggc gtggaaatat tcttattggt agaaacaact acaccctggt   7080
catcatcctg cctttctctt tatggttaca atgatataca ctgtttgaga tgaggataaa   7140
atactctgag tccaaaccgg gcccctctgc taaccatgtt catgccttct tctctttcct   7200
acagctcctg ggcaacgtgc tggttgttgt gctgtctcat cattttggca aagaatt      7257
```

<210> SEQ ID NO 16
<211> LENGTH: 3892
<212> TYPE: DNA
<213> ORGANISM: Artificial
<220> FEATURE:
<223> OTHER INFORMATION: Synthetic construct

<400> SEQUENCE: 16

```
aggcctccgc gccgggtttt ggcgcctccc gcgggcgccc ccctcctcac ggcgagcgct     60
gccacgtcag acgaagggcg cagcgagcgt cctgatcctt ccgcccggac gctcaggaca    120
```

```
gcggcccgct gctcataaga ctcggcctta gaaccccagt atcagcagaa ggacatttta    180
ggacgggact tgggtgactc tagggcactg gttttctttc cagagagcgg aacaggcgag    240
gaaaagtagt cccttctcgg cgattctgcg gagggatctc cgtggggcgg tgaacgccga    300
tgattatata aggacgcgcc gggtgtggca cagctagttc cgtcgcagcc gggatttggg    360
tcgcggttct tgtttgtgga tcgctgtgat cgtcacttgg tgagtagcgg gctgctgggc    420
tggccggggc tttcgtggcc gccgggccgc tcggtgggac ggaagcgtgt ggagagaccg    480
ccaagggctg tagtctgggt ccgcgagcaa ggttgccctg aactgggggt tgggggggagc    540
gcagcaaaat ggcggctgtt cccgagtctt gaatggaaga cgcttgtgag gcgggctgtg    600
aggtcgttga aacaaggtgg ggggcatggt gggcggcaag aacccaaggt cttgaggcct    660
tcgctaatgc gggaaagctc ttattcgggt gagatgggct ggggcaccat ctggggaccc    720
tgacgtgaag tttgtcactg actggagaac tcggtttgtc gtctgttgcg ggggcggcag    780
ttatggcggt gccgttgggc agtgcacccg tacctttggg agcgcgcgcc ctcgtcgtgt    840
cgtgacgtca cccgttctgt tggcttataa tgcagggtgg ggccacctgc cggtaggtgt    900
gcggtaggct tttctccgtc gcaggacgca gggttcgggc ctagggtagg ctctcctgaa    960
tcgacaggcg ccggacctct ggtgagggga gggataagtg aggcgtcagt ttctttggtc   1020
ggttttatgt acctatcttc ttaagtagct gaagctccgg ttttgaacta tgcgctcggg   1080
gttggcgagt gtgttttgtg aagtttttta ggcacctttt gaaatgtaat catttgggtc   1140
aatatgtaat tttcagtgtt agactagtaa attgtccgct aaattctggc cgtttttggc   1200
ttttttgtta gacgtcgacc gatcctgaga acttcagggt gagtttgggg acccttgatt   1260
gttctttctt tttcgctatt gtaaaattca tgttatatgg agggggcaaa gttttcaggg   1320
tgttgtttag aatgggaaga tgtcccttgt atcaccatgg accctcatga taattttgtt   1380
tctttcactt tctactctgt tgacaaccat tgtctcctct tattttcttt tcattttctg   1440
taactttttc gttaaacttt agcttgcatt tgtaacgaat ttttaaattc acttttgttt   1500
atttgtcaga ttgtaagtac tttctctaat cactttttt tcaaggcaat cagggtatat   1560
tatattgtac ttcagcacag ttttagagaa caattgttat aattaaatga taaggtagaa   1620
tatttctgca tataaattct ggctggcgtg gaaatattct tattggtaga aacaactaca   1680
ccctggtcat catcctgcct ttctctttat ggttacaatg atatacactg tttgagatga   1740
ggataaaata ctctgagtcc aaaccgggcc cctctgctaa ccatgttcat gccttcttct   1800
ctttcctaca gctcctgggc aacgtgctgg ttgttgtgct gtctcatcat tttggcaaag   1860
aattaagctt atactcgagc tctagattgg gaacccgggt ctctcgaatt cgatgccttt   1920
tagactcctg ataccattgg gtcttgtttg cgttctcctc cctctccatc acggcgcccc   1980
aggtccagac ggtaccgcac ctgatcctgc ccattaccgc gaacgcgtta aagccatgtt   2040
ctaccacgcc tatgactcct atctggaaaa tgcattcccc tatgatgagc tccgacccct   2100
tacctgcgat ggtcatgata cttggggctc tttttccctt acccttattg acgctctgga   2160
cacactcctt atcctcggaa acaccagcga atttcaaaga gtagttgaag tacttcagga   2220
caatgtcgac tttgacatcg atgtgaacgc atcagttttc gaaacaaata taagagtcgt   2280
tggaggtctg ctctccgccc accttctctc taaaaaagcc ggagtagaag ttgaagctgg   2340
ctggccctgc tccggacccc tccttcgtat ggctgaagaa gctgcccgca aactccttcc   2400
cgcttttcag accccaaccg gtatgcccta tggtactgtt aacctcctgc acggagtaaa   2460
```

```
tcccggcgaa acccccgtca catgtacagc cggaattgga acctttattg tggaatttgc   2520

aacccttagc agcctgaccg gagatcctgt attcgaagac gtggctcggg ttgccctgat   2580

gcgactgtgg gaatccaggt ctgatatcgg tctggtcggt aaccatatag acgtactcac   2640

tggtaaatgg gttgcacaag acgctggaat tggggcaggc gtggattctt attttgaata   2700

tctcgtaaaa ggggccatac tcttgcagga caaaaaactt atggctatgt tcctggaata   2760

taacaaagct attaggaact acacacactt cgatgattgg tatttgtggg tccaaatgta   2820

taaaggaacc gtttctatgc ctgtctttca gtcactggag gcttattggc ctggtctgca   2880

atccctgatc ggagacattg acaatgcaat gaggacattc cttaattatt acactgtttg   2940

gaagcagttc ggcggattgc ccgaatttta caacattcct caaggctata cagttgaaaa   3000

aagagaagga tatcccctgc gccccgagct tattgaaagc gctatgtatc tgtatcgtgc   3060

aacaggtgat ccaaccctgc ttgaactggg acgagacgcc gtcgaatcaa tcgagaaaat   3120

ttcaaaagtg gaatgcggct ttgcaacaat taaagatctt agagaccaca aactggataa   3180

tcgcatggag tcattctttt tggctgagac cgtcaagtat ctgtatctgc tttttcatcc   3240

caacaacttc atccataata acgggtccac cttcgattca gtcatgaccc ctcacggtga   3300

atgcatactc ggagctggag gctatatttt taacactgaa gctcacccaa ttgacccagc   3360

tgcccttcat tgttgtcgac gtctgaaaga agaacaatgg gaggttgaag atttgatcaa   3420

agaattttac tcacttaaac aaagtcgacc taaacgcgca cagagaaaaa ctgtaagatc   3480

tggtccttgg gaacctcagt ccggcccagc aactctttca tcccccgcca accaaccacg   3540

agaaaaacaa ccagcccaac agagaacccc cctgctcagc tgcccctctc agcccttcac   3600

ttcaaaactc gccctgcttg gacaggtgtt tctggactcc tcttgattta aacacgcggc   3660

cgctaatcag ccataccaca tttgtagagg ttttacttgc tttaaaaaac ctcccacacc   3720

tccccctgaa cctgaaacat aaaatgaatg caattgttgt tgttaacttg tttattgcag   3780

cttataatgg ttacaaataa agcaatagca tcacaaattt cacaaataaa gcatttttt   3840

cactgcattc tagttgtggt ttgtccaaac tcatcaatgt atcttatcat gt           3892
```

<210> SEQ ID NO 17
<211> LENGTH: 6629
<212> TYPE: DNA
<213> ORGANISM: Artificial
<220> FEATURE:
<223> OTHER INFORMATION: Synthetic plasmid

<400> SEQUENCE: 17

```
aagcttatac tcgagctcta gattgggaac ccgggtctct cgaattcatg gtggtggtgg     60

ctgctgctcc ttctgctgct acagctgctc ctaaggtgct gctgctgtct ggacagcctg    120

cttctggagg aagagctctg cctctgatgg tgcctggacc tagagctgct ggatctgagg    180

cttctggaac acctcaggct agaaagagac agagactgac acatctgtct cctgaagaaa    240

aggctctgag aagaaagctg aagaatagag tggctgctca gacagctaga gatagaaaga    300

aggctagaat gtctgaactg gaacagcagg tggtggatct ggaagaagaa aatcataagc    360

tgcagctgga aaatcagctg ctgagagaaa agacacatgg actggtggtg gaaaatcagg    420

aactgagaac aagactggga atggatacac tggatcctga tgaagtgcct gaagtggaag    480

ctaagggatc tggagtgaga ctggtggctg gatctgctga atctgctgct ggagctggac    540

ctgtggtgac atctcctgaa catctgccta tggattctga tacagtggct tcttctgatt    600

ctgaatctga tatcctgctg ggaatcctgg ataagctgga tcctgtgatg ttttttaagt    660
```

```
gtccttctcc tgaatctgct tctctggaag aactgcctga agtgtatcct gaaggacctt    720
cttctctgcc tgcttctctg tctctgtctg tgggaacatc ttctgctaag ctggaagcta    780
tcaatgaact gatcagattt gatcatgtgt atacaaagcc tctggtgctg gaaatccctt    840
ctgaaacaga atctcagaca aatgtggtgg tgaagatcga agaagctcct ctgtcttctt    900
ctgaagaaga tcatcctgaa tttatcgtgt ctgtgaagaa ggaacctctg gaagatgatt    960
ttatccctga actgggaatc tctaatctgc tgtcttcttc tcattgtctg agacctcctt   1020
cttgtctgct ggatgctcat tctgattgtg gatatgaagg atctccttct ccttttctg    1080
atatgtcttc tcctctggga acagatcatt cttgggaaga tacatttgct aatgaactgt   1140
ttcctcagct gatctctgtg tgagcggccg ctaatcagcc ataccacatt tgtagaggtt   1200
ttacttgctt taaaaaacct cccacacctc cccctgaacc tgaaacataa aatgaatgca   1260
attgttgttg ttaacttgtt tattgcagct tataatggtt acaaataaag caatagcatc   1320
acaaatttca caaataaagc attttttca ctgcattcta gttgtggttt gtccaaactc    1380
atcaatgtat cttatcatgt ctaccggtag ggcccctctc ttcatgtgag caaaaggcca   1440
gcaaaaggcc aggaaccgta aaaaggccgc gttgctggcg tttttccata ggctccgccc   1500
ccctgacgag catcacaaaa atcgacgctc aagtcagagg tggcgaaacc cgacaggact   1560
ataaagatac caggcgtttc cccctggaag ctccctcgtg cgctctcctg ttccgaccct   1620
gccgcttacc ggatacctgt ccgcctttct cccttcggga agcgtggcgc tttctcatag   1680
ctcacgctgt aggtatctca gttcggtgta ggtcgttcgc tccaagctgg gctgtgtgca   1740
cgaacccccc gttcagcccg accgctgcgc cttatccggt aactatcgtc ttgagtccaa   1800
cccggtaaga cacgacttat cgccactggc agcagccact ggtaacagga ttagcagagc   1860
gaggtatgta ggcggtgcta cagagttctt gaagtggtgg cctaactacg gctacactag   1920
aaggacagta tttggtatct gcgctctgct gaagccagtt accttcggaa aaagagttgg   1980
tagctcttga tccggcaaac aaaccaccgc tggtagcggt ggtttttttg tttgcaagca   2040
gcagattacg cgcagaaaaa aaggatctca agaagatcct ttgatctttt ctacggggtc   2100
tgacgctcag tggaacgaaa actcacgtta agggattttg gtcatgggcg cgcctcatac   2160
tcctgcaggc atgagattat caaaaaggat cttcacctag atccttttaa attaaaaatg   2220
aagttttaaa tcaatctaaa gtatatatga gtaaacttgg tctgacagtt accaatgctt   2280
aatcagtgag gcacctatct cagcgatctg tctatttcgt tcatccatag ttgcctgact   2340
ccccgtcgtg tagataacta cgatacggga gggcttacca tctggcccca gtgctgcaat   2400
gataccgcga gacccacgct caccggctcc agatttatca gcaataaacc agccagccgg   2460
aagggccgag cgcagaagtg gtcctgcaac tttatccgcc tccatccagt ctattaattg   2520
ttgccgggaa gctagagtaa gtagttcgcc agttaatagt ttgcgcaacg ttgttgccat   2580
tgctacaggc atcgtggtgt cacgctcgtc gtttggtatg gcttcattca gctccggttc   2640
ccaacgatca aggcgagtta catgatcccc catgttgtgc aaaaaagcgg ttagctcctt   2700
cggtcctccg atcgttgtca gaagtaagtt ggccgcagtg ttatcactca tggttatggc   2760
agcactgcat aattctctta ctgtcatgcc atccgtaaga tgcttttctg tgactggtga   2820
gtactcaacc aagtcattct gagaatagtg tatgcggcga ccgagttgct cttgcccggc   2880
gtcaatacgg gataataccg cgccacatag cagaacttta aaagtgctca tcattggaaa   2940
acgttcttcg gggcgaaaac tctcaaggat cttaccgctg ttgagatcca gttcgatgta   3000
```

```
acccactcgt gcacccaact gatcttcagc atcttttact ttcaccagcg tttctgggtg   3060
agcaaaaaca ggaaggcaaa atgccgcaaa aaagggaata agggcgacac ggaaatgttg   3120
aatactcata ctcttccttt ttcaatatta ttgaagcatt tatcagggtt attgtctcat   3180
gagcggatac atatttgaat gtatttagaa aaataaacaa atagggggttc cgcgcacatt   3240
tccccgaaaa gtgccacctg acgtcaggta ccaagcctag gcctccaaaa aagcctcctc   3300
actacttctg gaatagctca gaggcagagg cggcctcggc ctctgcataa ataaaaaaaa   3360
ttagtcagcc atggggcgga gaatgggcgg aactgggcgg agttaggggc gggatgggcg   3420
gagttagggg cgggactatg gttgctgact aattgagatg catgctttgc atacttctgc   3480
ctgctgggga gcctggggac tttccacacc tggttgctga ctaattgaga tgcatgcttt   3540
gcatacttct gcctgctggg gagcctgggg actttccaca ccggatccac catggccaag   3600
ttgaccagtg ccgttccggt gctcaccgcg cgcgacgtcg ccggagcggt cgagttctgg   3660
accgaccggc tcgggttctc ccgggacttc gtggaggacg acttcgccgg tgtggtccgg   3720
gacgacgtga ccctgttcat cagcgcggtc caggaccagg tggtgccgga caacaccctg   3780
gcctgggtgt gggtgcgcgg cctggacgag ctgtacgccg agtggtcgga ggtcgtgtcc   3840
acgaacttcc gggacgcctc cgggccggcc atgaccgaga tcggcgagca gccgtggggg   3900
cgggagttcg ccctgcgcga cccggccggc aactgcgtgc acttcgtggc cgaggagcag   3960
gactgaacgc gtgctgtaag tctgcagaaa ttgatgatct attaaacaat aaagatgtcc   4020
actaaaatgg aagtttttcc tgtcatactt tgttaagaag ggtgagaaca gagtacctac   4080
attttgaatg gaaggattgg agctacgggg gtgggggtgg ggtgggatta gataaatgcc   4140
tgctctttac tgaaggctct ttactattgc tttatgataa tgtttcatag ttggatatca   4200
taatttaaac aagcaaaacc aaattaaggg ccagctcatt cctcccactc atgatctatg   4260
gatctataga tctctcgtgc agctggggct ctagggggta tccccacgcg ccctgtagcg   4320
gcgcattaag cgcggcgggt gtggtggtta cgcgcagcgt gaccgctaca cttgccagcg   4380
ccctagcgcc cgctcctttc gctttcttcc cttcctttct cgccacgttc gccggctttc   4440
cccgtcaagc tctaaatcgg gggctccctt tagggttccg atttagtgct ttacggcacc   4500
tcgaccccaa aaaacttgat tagggtgatg gttcacgtag tgggccatcg ccctgataga   4560
cggtttttcg ccctttgacg ttggagtcca cgttctttaa tagtggactc ttgttccaaa   4620
ctggaacaac actcaaccct atctcggtct attcttttga tttataaggg attttgccga   4680
tttcggccta ttggttaaaa aatgagctga tttaacaaaa atttaacgcg aattaattct   4740
gtggaatgtg tgtcagttag tcgcgaggcc tccgcgccgg gttttggcgc ctcccgcggg   4800
cgcccccctc ctcacggcga gcgctgccac gtcagacgaa gggcgcagcg agcgtcctga   4860
tccttccgcc cggacgctca ggacagcggc ccgctgctca taagactcgg ccttagaacc   4920
ccagtatcag cagaaggaca ttttaggacg ggacttgggt gactctaggg cactggtttt   4980
ctttccagag agcggaacag gcgaggaaaa gtagtccctt ctcggcgatt ctgcggaggg   5040
atctccgtgg ggcggtgaac gccgatgatt atataaggac gcgccgggtg tggcacagct   5100
agttccgtcg cagccgggat ttgggtcgcg gttcttgttt gtggatcgct gtgatcgtca   5160
cttggtgagt agcgggctgc tgggctggcc ggggctttcg tggccgccgg gccgctcggt   5220
gggacggaag cgtgtggaga gaccgccaag ggctgtagtc tgggtccgcg agcaaggttg   5280
ccctgaactg ggggttgggg ggagcgcagc aaaatggcgg ctgttcccga gtcttgaatg   5340
gaagacgctt gtgaggcggg ctgtgaggtc gttgaaacaa ggtgggggc atggtgggcg   5400
```

gcaagaaccc aaggtcttga ggccttcgct aatgcgggaa agctcttatt cgggtgagat 5460 gggctggggc accatctggg gaccctgacg tgaagtttgt cactgactgg agaactcggt 5520 ttgtcgtctg ttgcgggggc ggcagttatg gcggtgccgt tgggcagtgc acccgtacct 5580 ttgggagcgc gcgccctcgt cgtgtcgtga cgtcacccgt tctgttggct tataatgcag 5640 ggtggggcca cctgccggta ggtgtgcggt aggcttttct ccgtcgcagg acgcagggtt 5700 cgggcctagg gtaggctctc ctgaatcgac aggcgccgga cctctggtga ggggagggat 5760 aagtgaggcg tcagtttctt tggtcggttt tatgtaccta tcttcttaag tagctgaagc 5820 tccggttttg aactatgcgc tcggggttgg cgagtgtgtt ttgtgaagtt ttttaggcac 5880 cttttgaaat gtaatcattt gggtcaatat gtaattttca gtgttagact agtaaattgt 5940 ccgctaaatt ctggccgttt ttggcttttt tgttagacgt cgaccgatcc tgagaacttc 6000 agggtgagtt tggggaccct tgattgttct ttctttttcg ctattgtaaa attcatgtta 6060 tatggagggg gcaaagtttt cagggtgttg tttagaatgg gaagatgtcc cttgtatcac 6120 catggaccct catgataatt ttgtttcttt cactttctac tctgttgaca accattgtct 6180 cctcttattt tcttttcatt ttctgtaact ttttcgttaa actttagctt gcatttgtaa 6240 cgaattttta aattcacttt tgtttatttg tcagattgta agtactttct ctaatcactt 6300 ttttttcaag gcaatcaggg tatattatat tgtacttcag cacagtttta gagaacaatt 6360 gttataatta aatgataagg tagaatattt ctgcatataa attctggctg gcgtggaaat 6420 attcttattg gtagaaacaa ctacaccctg gtcatcatcc tgcctttctc tttatggtta 6480 caatgatata cactgtttga gatgaggata aaatactctg agtccaaacc gggcccctct 6540 gctaaccatg ttcatgcctt cttctctttc ctacagctcc tgggcaacgt gctggttgtt 6600 gtgctgtctc atcattttgg caaagaatt 6629

<210> SEQ ID NO 18
<211> LENGTH: 3264
<212> TYPE: DNA
<213> ORGANISM: Artificial
<220> FEATURE:
<223> OTHER INFORMATION: Synthetic construct

<400> SEQUENCE: 18 ggcctccgcg ccgggttttg gcgcctcccg cgggcgcccc cctcctcacg gcgagcgctg 60 ccacgtcaga cgaagggcgc agcgagcgtc ctgatccttc cgcccggacg ctcaggacag 120 cggcccgctg ctcataagac tcggccttag aaccccagta tcagcagaag gacattttag 180 gacgggactt gggtgactct agggcactgg ttttctttcc agagagcgga acaggcgagg 240 aaaagtagtc ccttctcggc gattctgcgg agggatctcc gtggggcggt gaacgccgat 300 gattatataa ggacgcgccg ggtgtggcac agctagttcc gtcgcagccg ggatttgggt 360 cgcggttctt gtttgtggat cgctgtgatc gtcacttggt gagtagcggg ctgctgggct 420 ggccggggct ttcgtggccg ccgggccgct cggtgggacg gaagcgtgtg gagagaccgc 480 caagggctgt agtctgggtc cgcgagcaag gttgccctga actgggggtt ggggggagcg 540 cagcaaaatg gcggctgttc ccgagtcttg aatggaagac gcttgtgagg cgggctgtga 600 ggtcgttgaa acaaggtggg gggcatggtg ggcggcaaga acccaaggtc ttgaggcctt 660 cgctaatgcg ggaaagctct tattcgggtg agatgggctg gggcaccatc tggggaccct 720 gacgtgaagt ttgtcactga ctggagaact cggtttgtcg tctgttgcgg gggcggcagt 780

-continued

```
tatggcggtg ccgttgggca gtgcacccgt acctttggga gcgcgcgccc tcgtcgtgtc    840
gtgacgtcac ccgttctgtt ggcttataat gcagggtggg gccacctgcc ggtaggtgtg    900
cggtaggctt ttctccgtcg caggacgcag ggttcgggcc tagggtaggc tctcctgaat    960
cgacaggcgc cggacctctg gtgaggggag ggataagtga ggcgtcagtt tctttggtcg   1020
gttttatgta cctatcttct taagtagctg aagctccggt tttgaactat gcgctcgggg   1080
ttggcgagtg tgttttgtga agtttttag gcaccttttg aaatgtaatc atttgggtca   1140
atatgtaatt ttcagtgtta gactagtaaa ttgtccgcta aattctggcc gtttttggct   1200
tttttgttag acgtcgaccg atcctgagaa cttcagggtg agtttgggga cccttgattg   1260
ttctttcttt ttcgctattg taaaattcat gttatatgga gggggcaaag ttttcagggt   1320
gttgtttaga atgggaagat gtcccttgta tcaccatgga ccctcatgat aattttgttt   1380
ctttcacttt ctactctgtt gacaaccatt gtctcctctt attttctttt cattttctgt   1440
aactttttcg ttaaacttta gcttgcattt gtaacgaatt tttaaattca cttttgttta   1500
tttgtcagat tgtaagtact ttctctaatc actttttttt caaggcaatc agggtatatt   1560
atattgtact tcagcacagt tttagagaac aattgttata attaaatgat aaggtagaat   1620
atttctgcat ataaattctg gctggcgtgg aaatattctt attggtagaa acaactacac   1680
cctggtcatc atcctgcctt tctctttatg gttacaatga tatacactgt ttgagatgag   1740
gataaaatac tctgagtcca aaccgggccc ctctgctaac catgttcatg ccttcttctc   1800
tttcctacag ctcctgggca acgtgctggt tgttgtgctg tctcatcatt ttggcaaaga   1860
attaagctta tactcgagct ctagattggg aacccgggtc tctcgaattc atggtggtgg   1920
tggctgctgc tccttctgct gctacagctg ctcctaaggt gctgctgctg tctggacagc   1980
ctgcttctgg aggaagagct ctgcctctga tggtgcctgg acctagagct gctggatctg   2040
aggcttctgg aacacctcag gctagaaaga gacagagact gacacatctg tctcctgaag   2100
aaaaggctct gagaagaaag ctgaagaata gagtggctgc tcagacagct agagatagaa   2160
agaaggctag aatgtctgaa ctggaacagc aggtggtgga tctggaagaa gaaaatcata   2220
agctgcagct ggaaaatcag ctgctgagag aaaagacaca tggactggtg gtggaaaatc   2280
aggaactgag aacaagactg ggaatggata cactggatcc tgatgaagtg cctgaagtgg   2340
aagctaaggg atctggagtg agactggtgg ctggatctgc tgaatctgct gctggagctg   2400
gacctgtggt gacatctcct gaacatctgc ctatggattc tgatacagtg gcttcttctg   2460
attctgaatc tgatatcctg ctgggaatcc tggataagct ggatcctgtg atgtttttta   2520
agtgtccttc tcctgaatct gcttctctgg aagaactgcc tgaagtgtat cctgaaggac   2580
cttcttctct gcctgcttct ctgtctctgt ctgtgggaac atcttctgct aagctggaag   2640
ctatcaatga actgatcaga tttgatcatg tgtatacaaa gcctctggtg ctggaaatcc   2700
cttctgaaac agaatctcag acaaatgtgg tggtgaagat cgaagaagct cctctgtctt   2760
cttctgaaga agatcatcct gaatttatcg tgtctgtgaa gaaggaacct ctggaagatg   2820
attttatccc tgaactggga atctctaatc tgctgtcttc ttctcattgt ctgagacctc   2880
cttcttgtct gctggatgct cattctgatt gtggatatga aggatctcct tctccttttt   2940
ctgatatgtc ttctcctctg ggaacagatc attcttggga agatacattt gctaatgaac   3000
tgtttcctca gctgatctct gtgtgagcgg ccgctaatca gccataccac atttgtagag   3060
gttttacttg ctttaaaaaa cctcccacac ctccccctga acctgaaaca taaaatgaat   3120
gcaattgttg ttgttaactt gtttattgca gcttataatg gttacaaata aagcaatagc   3180
```

```
atcacaaatt tcacaaataa agcatttttt tcactgcatt ctagttgtgg tttgtccaaa   3240

ctcatcaatg tatcttatca tgtc                                          3264


<210> SEQ ID NO 19
<211> LENGTH: 447
<212> TYPE: PRT
<213> ORGANISM: Homo sapiens

<400> SEQUENCE: 19

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 20
<211> LENGTH: 110
<212> TYPE: PRT
<213> ORGANISM: Homo sapiens

<400> SEQUENCE: 20

Glu Ser Gly Gly Asp Leu Val Gln Pro Gly Gly Ser Leu Arg Leu Ser
1               5                   10                  15

Cys Ala Ala Ser Gly Phe Thr Phe Ser Ala Tyr Ala Met Thr Trp Val
            20                  25                  30

Arg Gln Ala Pro Gly Lys Gly Leu Glu Trp Val Ser Ala Ile Ser Gly
        35                  40                  45

Ser Gly Gly Ser Ala Tyr Tyr Ala Asp Ser Val Lys Gly Arg Phe Thr
    50                  55                  60

Ile Ser Arg Asp Asn Ser Lys Asn Thr Val Tyr Leu Gln Met Asn Ser
65                  70                  75                  80

Leu Arg Ala Glu Asp Thr Ala Val Tyr Tyr Cys Ala Lys Asp Gly Ala
                85                  90                  95

Trp Lys Met Ser Gly Leu Asp Val Trp Gly Gln Gly Thr Thr
            100                 105                 110


<210> SEQ ID NO 21
<211> LENGTH: 214
<212> TYPE: PRT
<213> ORGANISM: Homo sapiens

<400> SEQUENCE: 21

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 22
<211> LENGTH: 100
<212> TYPE: PRT
<213> ORGANISM: Homo sapiens

<400> SEQUENCE: 22

Gln Ser Pro Ala Ser Leu Ser Ala Ser Val Gly Asp Arg Val Thr Ile
1               5                   10                  15

Thr Cys Arg Ala Ser Gln Asp Ile Ser Asp Tyr Leu Ala Trp Tyr Gln
            20                  25                  30

Gln Lys Pro Gly Lys Ile Pro Arg Leu Leu Ile Tyr Thr Thr Ser Thr
        35                  40                  45

Leu Gln Ser Gly Val Pro Ser Arg Phe Arg Gly Ser Gly Ser Gly Thr
    50                  55                  60

Asp Phe Thr Leu Thr Ile Ser Ser Leu Gln Pro Glu Asp Val Ala Thr
65                  70                  75                  80

Tyr Tyr Cys Gln Lys Tyr Asp Ser Ala Pro Leu Thr Phe Gly Gly Gly
                85                  90                  95

Thr Lys Val Glu
            100


<210> SEQ ID NO 23
<211> LENGTH: 2971
<212> TYPE: DNA
<213> ORGANISM: Artificial
<220> FEATURE:
<223> OTHER INFORMATION: Synthetic construct

<400> SEQUENCE: 23

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctca tgatagaagc actctactat tcgtcgaccg    600

atcctgagaa cttcagggtg agtttgggga cccttgattg ttctttcttt ttcgctattg    660
```

```
taaaattcat gttatatgga gggggcaaag ttttcagggt gttgtttaga atgggaagat    720
gtcccttgta tcaccatgga ccctcatgat aattttgttt ctttcacttt ctactctgtt    780
gacaaccatt gtctcctctt attttctttt cattttctgt aactttttcg ttaaacttta    840
gcttgcattt gtaacgaatt tttaaattca cttttgttta tttgtcagat tgtaagtact    900
ttctctaatc actttttttt caaggcaatc agggtatatt atattgtact tcagcacagt    960
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcag aggtgcaggt gttggagtct gggggagact tggtacagcc tgggggggtcc   1440
ctgagactct cctgtgcagc ctctggattc acctttagtg cctatgccat gacctgggtc   1500
cgccaggctc cagggaaggg gctggagtgg gtctcagcta ttagtggtag tggtggtagc   1560
gcatactacg cagactccgt gaagggccgg ttcaccatct ccagagacaa ttccaagaac   1620
acggtatatc tgcagatgaa cagcctgaga gccgaggaca cggccgtata ttactgtgcg   1680
aaagatgggg cctggaaaat gtccggtttg gacgtctggg gccaagggac cacggtcatc   1740
gtctcctcag cctccaccaa gggcccatcg gtcttccccc tggcgccctg ctccaggagc   1800
acctccgaga gcacagccgc cctgggctgc ctggtcaagg actacttccc cgaaccggtg   1860
acggtgtcgt ggaactcagg cgccctgacc agcggcgtgc acaccttccc ggctgtccta   1920
cagtcctcag gactctactc cctcagcagc gtggtgaccg tgccctccag cagcttgggc   1980
acgaagacct acacctgcaa cgtagatcac aagcccagca acaccaaggt ggacaagaga   2040
gttgagtcca aatatggtcc cccatgccca ccctgcccag cacctgagtt cctgggggga   2100
ccatcagtct tcctgttccc cccaaaaccc aaggacactc tcatgatctc ccggacccct   2160
gaggtcacgt gcgtggtggt ggacgtgagc caggaagacc ccgaggtcca gttcaactgg   2220
tacgtggatg gcgtggaggt gcataatgcc aagacaaagc cgcgggagga gcagttcaac   2280
agcacgtacc gtgtggtcag cgtcctcacc gtcctgcacc aggactggct gaacggcaag   2340
gagtacaagt gcaaggtctc caacaaaggc ctcccgtcct ccatcgagaa aaccatctcc   2400
aaagccaaag ggcagccccg agagccacag gtgtacaccc tgcccccatc ccaggaggag   2460
atgaccaaga accaggtcag cctgacctgc ctggtcaaag gcttctaccc cagcgacatc   2520
gccgtggagt gggagagcaa tgggcagccg gagaacaact acaagaccac gcctcccgtg   2580
ctggactccg acggctcctt cttcctctac agcaggctca ccgtggacaa gagcaggtgg   2640
caggagggga atgtcttctc atgctccgtg atgcatgagg ctctgcacaa ccactacaca   2700
cagaagtccc tctccctgtc tctgggtaaa tgagcggccg ctaatcagcc ataccacatt   2760
tgtagaggtt ttacttgctt taaaaaacct cccacacctc cccctgaacc tgaaacataa   2820
aatgaatgca attgttgttg ttaacttgtt tattgcagct tataatggtt acaaataaag   2880
caatagcatc acaaatttca caaataaagc attttttca ctgcattcta gttgtggttt   2940
gtccaaactc atcaatgtat cttatcatgt c                                  2971
```

<210> SEQ ID NO 24
<211> LENGTH: 7013
<212> TYPE: DNA
<213> ORGANISM: Artificial
<220> FEATURE:
<223> OTHER INFORMATION: Synthetic plasmid

<400> SEQUENCE: 24 tcgcgatgtg tgactagtta gttattaata gtaatcaatt acggggtcat tagttcatag 60 cccatatatg gagttccgcg ttacataact tacggtaaat ggcccgcctg gctgaccgcc 120 caacgacccc cgcccattga cgtcaataat gacgtatgtt cccatagtaa cgccaatagg 180 gactttccat tgacgtcaat gggtggagta tttacggtaa actgcccact tggcagtaca 240 tcaagtgtat catatgccaa gtacgccccc tattgacgtc aatgacggta aatggcccgc 300 ctggcattat gcccagtaca tgaccttatg ggactttcct acttggcagt acatctacgt 360 attagtcatc gctattacca tggtgatgcg gttttggcag tacatcaatg ggcgtggata 420 gcggtttgac tcacggggat ttccaagtct ccaccccatt gacgtcaatg ggagtttgtt 480 ttggcaccaa aatcaacggg actttccaaa atgtcgtaac aactccgccc cattgacgca 540 aatgggcggt aggcgtgtac ggtgggaggt ctatataagc agagctcatg atagaagcac 600 tctactattc gtcgaccgat cctgagaact tcagggtgag tttggggacc cttgattgtt 660 ctttcttttt cgctattgta aaattcatgt tatatggagg gggcaaagtt ttcagggtgt 720 tgtttagaat gggaagatgt cccttgtatc accatggacc ctcatgataa ttttgtttct 780 ttcactttct actctgttga caaccattgt ctcctcttat tttcttttca ttttctgtaa 840 ctttttcgtt aaactttagc ttgcatttgt aacgaatttt taaattcact tttgtttatt 900 tgtcagattg taagtacttt ctctaatcac tttttttca aggcaatcag ggtatattat 960 attgtacttc agcacagttt tagagaacaa ttgttataat taaatgataa ggtagaatat 1020 ttctgcatat aaattctggc tggcgtggaa atattcttat tggtagaaac aactacaccc 1080 tggtcatcat cctgcctttc tctttatggt tacaatgata tacactgttt gagatgagga 1140 taaaatactc tgagtccaaa ccgggcccct ctgctaacca tgttcatgcc ttcttctctt 1200 tcctacagct cctgggcaac gtgctggttg ttgtgctgtc tcatcatttt ggcaaagaat 1260 taagcttata ctcgagctct agattgggaa cccgggtctc tcgaattcga gatctccacc 1320 atgcacagac ctagacgtcg tggaactcgt ccacctccac tggcactgct cgctgctctc 1380 ctcctggctg cacgtggtgc tgatgcagag gtgcaggtgt tggagtctgg gggagacttg 1440 gtacagcctg gggggtccct gagactctcc tgtgcagcct ctggattcac ctttagtgcc 1500 tatgccatga cctgggtccg ccaggctcca gggaaggggc tggagtgggt ctcagctatt 1560 agtggtagtg gtggtagcgc atactacgca gactccgtga agggccggtt caccatctcc 1620 agagacaatt ccaagaacac ggtatatctg cagatgaaca gcctgagagc cgaggacacg 1680 gccgtatatt actgtgcgaa agatggggcc tggaaaatgt ccggtttgga cgtctggggc 1740 caagggacca cggtcatcgt ctcctcagcc tccaccaagg gcccatcggt cttccccctg 1800 gcgccctgct ccaggagcac ctccgagagc acagccgccc tgggctgcct ggtcaaggac 1860 tacttccccg aaccggtgac ggtgtcgtgg aactcaggcg ccctgaccag cggcgtgcac 1920 accttcccgg ctgtcctaca gtcctcagga ctctactccc tcagcagcgt ggtgaccgtg 1980 ccctccagca gcttgggcac gaagacctac acctgcaacg tagatcacaa gcccagcaac 2040 accaaggtgg acaagagagt tgagtccaaa tatggtcccc catgcccacc ctgcccagca 2100

```
cctgagttcc tgggggggacc atcagtcttc ctgttccccc caaaacccaa ggacactctc   2160
atgatctccc ggacccctga ggtcacgtgc gtggtggtgg acgtgagcca ggaagacccc   2220
gaggtccagt tcaactggta cgtggatggc gtggaggtgc ataatgccaa gacaaagccg   2280
cgggaggagc agttcaacag cacgtaccgt gtggtcagcg tcctcaccgt cctgcaccag   2340
gactggctga acggcaagga gtacaagtgc aaggtctcca acaaaggcct cccgtcctcc   2400
atcgagaaaa ccatctccaa agccaaaggg cagccccgag agccacaggt gtacaccctg   2460
cccccatccc aggaggagat gaccaagaac caggtcagcc tgacctgcct ggtcaaaggc   2520
ttctacccca gcgacatcgc cgtggagtgg gagagcaatg ggcagccgga gaacaactac   2580
aagaccacgc ctcccgtgct ggactccgac ggctccttct tcctctacag caggctcacc   2640
gtggacaaga gcaggtggca ggaggggaat gtcttctcat gctccgtgat gcatgaggct   2700
ctgcacaacc actacacaca gaagtccctc tccctgtctc tgggtaaatg agcggccgct   2760
aatcagccat accacatttg tagaggtttt acttgcttta aaaaacctcc cacacctccc   2820
cctgaacctg aaacataaaa tgaatgcaat tgttgttgtt aacttgttta ttgcagctta   2880
taatggttac aaataaagca atagcatcac aaatttcaca aataaagcat ttttttcact   2940
gcattctagt tgtggtttgt ccaaactcat caatgtatct tatcatgtct accggtcctg   3000
cagggcccct ctcttcatgt gagcaaaagg ccagcaaaag gccaggaacc gtaaaaaggc   3060
cgcgttgctg gcgtttttcc ataggctccg cccccctgac gagcatcaca aaaatcgacg   3120
ctcaagtcag aggtggcgaa acccgacagg actataaaga taccaggcgt ttccccctgg   3180
aagctccctc gtgcgctctc ctgttccgac cctgccgctt accggatacc tgtccgcctt   3240
tctcccttcg ggaagcgtgg cgctttctca atgctcacgc tgtaggtatc tcagttcggt   3300
gtaggtcgtt cgctccaagc tgggctgtgt gcacgaaccc cccgttcagc ccgaccgctg   3360
cgccttatcc ggtaactatc gtcttgagtc caacccggta agacacgact tatcgccact   3420
ggcagcagcc actggtaaca ggattagcag agcgaggtat gtaggcggtg ctacagagtt   3480
cttgaagtgg tggcctaact acggctacac tagaaggaca gtatttggta tctgcgctct   3540
gctgaagcca gttaccttcg gaaaaagagt tggtagctct tgatccggca aacaaaccac   3600
cgctggtagc ggtggttttt ttgtttgcaa gcagcagatt acgcgcagaa aaaaaggatc   3660
tcaagaagat cctttgatct tttctacggg gtctgacgct cagtggaacg aaaactcacg   3720
ttaagggatt ttggtcatgg gcgcgcctca tactcctgca ggcatgagat tatcaaaaag   3780
gatcttcacc tagatccttt taaattaaaa atgaagtttt aaatcaatct aaagtatata   3840
tgagtaaact tggtctgaca gttaccaatg cttaatcagt gaggcaccta tctcagcgat   3900
ctgtctattt cgttcatcca tagttgcctg actccccgtc gtgtagataa ctacgatacg   3960
ggagggctta ccatctggcc ccagtgctgc aatgataccg cgagacccac gctcaccggc   4020
tccagattta tcagcaataa accagccagc cggaagggcc gagcgcagaa gtggtcctgc   4080
aactttatcc gcctccatcc agtctattaa ttgttgccgg gaagctagag taagtagttc   4140
gccagttaat agtttgcgca acgttgttgc cattgctaca ggcatcgtgg tgtcacgctc   4200
gtcgtttggt atggcttcat tcagctccgg ttcccaacga tcaaggcgag ttacatgatc   4260
ccccatgttg tgcaaaaaag cggttagctc cttcggtcct ccgatcgttg tcagaagtaa   4320
gttggccgca gtgttatcac tcatggttat ggcagcactg cataattctc ttactgtcat   4380
gccatccgta agatgctttt ctgtgactgg tgagtactca accaagtcat tctgagaata   4440
gtgtatgcgg cgaccgagtt gctcttgccc ggcgtcaata cgggataata ccgcgccaca   4500
```

tagcagaact ttaaaagtgc tcatcattgg aaaacgttct tcggggcgaa aactctcaag 4560
gatcttaccg ctgttgagat ccagttcgat gtaacccact cgtgcaccca actgatcttc 4620
agcatctttt actttcacca gcgtttctgg gtgagcaaaa acaggaaggc aaaatgccgc 4680
aaaaaaggga ataagggcga cacggaaatg ttgaatactc atactcttcc tttttcaata 4740
ttattgaagc atttatcagg gttattgtct catgagcgga tacatatttg aatgtattta 4800
gaaaaataaa caaatagggg ttccgcgcac atttccccga aaagtgccac ctgacgtcag 4860
gtaccaagcc taggcctcca aaaaagcctc ctcactactt ctggaatagc tcagaggcag 4920
aggcggcctc ggcctctgca taaataaaaa aaattagtca gccatggggc ggagaatggg 4980
cggaactggg cggagttagg ggcgggatgg gcggagttag gggcgggact atggttgctg 5040
actaattgag atgcatgctt tgcatacttc tgcctgctgg ggagcctggg gactttccac 5100
acctggttgc tgactaattg agatgcatgc tttgcatact tctgcctgct ggggagcctg 5160
gggactttcc acaccggatc caccatggat agatccggaa agcctgaact caccgcgacg 5220
tctgtcgaga agtttctgat cgaaaagttc gacagcgtct ccgacctgat gcagctctcg 5280
gagggcgaag aatctcgtgc tttcagcttc gatgtaggag ggcgtggata tgtcctgcgg 5340
gtaaatagct gcgccgatgg tttctacaaa gatcgttatg tttatcggca ctttgcatcg 5400
gccgcgctcc cgattccgga agtgcttgac attggggagt tcagcgagag cctgacctat 5460
tgcatctccc gccgtgcaca gggtgtcacg ttgcaagacc tgcctgaaac cgaactgccc 5520
gctgttctgc agccggtcgc ggaggccatg gatgcgatcg ctgcggccga tcttagccag 5580
acgagcgggt tcggcccatt cggaccgcaa ggaatcggtc aatacactac atggcgtgat 5640
ttcatatgcg cgattgctga tccccatgtg tatcactggc aaactgtgat ggacgacacc 5700
gtcagtgcgt ccgtcgcgca ggctctcgat gagctgatgc tttgggccga ggactgcccc 5760
gaagtccggc acctcgtgca cgcggatttc ggctccaaca atgtcctgac ggacaatggc 5820
cgcataacag cggtcattga ctggagcgag gcgatgttcg gggattccca atacgaggtc 5880
gccaacatct tcttctggag gccgtggttg gcttgtatgg agcagcagac gcgctacttc 5940
gagcggaggc atccggagct tgcaggatcg ccgcggctcc gggcgtatat gctccgcatt 6000
ggtcttgacc aactctatca gagcttggtt gacggcaatt tcgatgatgc agcttgggcg 6060
cagggtcgat gcgacgcaat cgtccgatcc ggagccggga ctgtcgggcg tacacaaatc 6120
gcccgcagaa gcgcggccgt ctggaccgat ggctgtgtag aagtactcgc cgatagtgga 6180
aaccgacgcc ccagcactcg tccgagggca aaggaataga cgcgtgctgt aagtctgcag 6240
aaattgatga tctattaaac aataaagatg tccactaaaa tggaagtttt tcctgtcata 6300
ctttgttaag aagggtgaga acagagtacc tacattttga atggaaggat tggagctacg 6360
ggggtggggg tggggtggga ttagataaat gcctgctctt tactgaaggc tctttactat 6420
tgctttatga taatgtttca tagttggata tcataattta aacaagcaaa accaaattaa 6480
gggccagctc attcctccca ctcatgatct atggatctat agatctctcg tgcagctggg 6540
gctctagggg gtatccccac gcgccctgta gcggcgcatt aagcgcggcg ggtgtggtgg 6600
ttacgcgcag cgtgaccgct acacttgcca gcgccctagc gcccgctcct ttcgctttct 6660
tcccttcctt tctcgccacg ttcgccggct ttccccgtca agctctaaat cgggggctcc 6720
ctttagggtt ccgatttagt gctttacggc acctcgaccc caaaaaactt gattagggtg 6780
atggttcacg tagtgggcca tcgccctgat agacggtttt tcgccctttg acgttggagt 6840

```
ccacgttctt taatagtgga ctcttgttcc aaactggaac aacactcaac cctatctcgg   6900

tctattcttt tgatttataa gggattttgc cgatttcggc ctattggtta aaaaatgagc   6960

tgatttaaca aaaatttaac gcgaattaat tctgtggaat gtgtgtcagt tag          7013


<210> SEQ ID NO 25
<211> LENGTH: 2272
<212> TYPE: DNA
<213> ORGANISM: Artificial
<220> FEATURE:
<223> OTHER INFORMATION: Synthetic construct

<400> SEQUENCE: 25

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctca tgatagaagc actctactat tcgtcgaccg    600

atcctgagaa cttcagggtg agtttgggga cccttgattg ttctttcttt ttcgctattg    660

taaaattcat gttatatgga gggggcaaag ttttcagggt gttgtttaga atgggaagat    720

gtcccttgta tcaccatgga ccctcatgat aattttgttt ctttcacttt ctactctgtt    780

gacaaccatt gtctcctctt attttctttt cattttctgt aactttttcg ttaaacttta    840

gcttgcattt gtaacgaatt tttaaattca cttttgttta tttgtcagat tgtaagtact    900

ttctctaatc actttttttt caaggcaatc agggtatatt atattgtact tcagcacagt    960

tttagagaac aattgttata attaaatgat aaggtagaat atttctgcat ataaattctg   1020

gctggcgtgg aaatattctt attggtagaa acaactacac cctggtcatc atcctgcctt   1080

tctctttatg gttacaatga tatacactgt ttgagatgag gataaaatac tctgagtcca   1140

aaccgggccc ctctgctaac catgttcatg ccttcttctc tttcctacag ctcctgggca   1200

acgtgctggt tgttgtgctg tctcatcatt ttggcaaaga attaagctta tactcgagct   1260

ctagattggg aacccgggtc tctcgaattc gagatctcca ccatgcacag acctagacgt   1320

cgtggaactc gtccacctcc actggcactg ctcgctgctc tcctcctggc tgcacgtggt   1380

gctgatgcag acatccagat gacccagtct ccagcctccc tgtctgcatc tgttggagac   1440

agagtcacca tcacttgtcg ggcgagtcag gacattagcg attatttagc ctggtatcag   1500

cagaaaccag ggaaaattcc taggctcctg atctatacta catccacttt gcaatcaggg   1560

gtcccatctc ggttccgtgg cagtgggtct gggacagatt tcactctcac catcagcagc   1620

ctgcagcctg aagatgttgc aacttattac tgtcagaagt atgacagtgc cccgctcact   1680

ttcggcggag ggaccaaggt ggagatcaaa cgaactgtgg ctgcaccatc tgtcttcatc   1740

ttcccgccat ctgatgagca gttgaaatct ggaactgcct ctgttgtgtg cctgctgaat   1800

aacttctatc ccagagaggc caaagtacag tggaaggtgg ataacgccct ccaatcgggt   1860

aactcccagg agagtgtcac agagcaggac agcaaggaca gcacctacag cctcagcagc   1920
```

```
accctgacgc tgagcaaagc agactacgag aaacacaaag tctacgcctg cgaagtcacc   1980

catcagggcc tgagctcgcc cgtcacaaag agcttcaaca ggggagagtg ttaggcggcc   2040

gctaatcagc cataccacat ttgtagaggt tttacttgct ttaaaaaacc tcccacacct   2100

ccccctgaac ctgaaacata aaatgaatgc aattgttgtt gttaacttgt ttattgcagc   2160

ttataatggt tacaaataaa gcaatagcat cacaaatttc acaaataaag catttttttc   2220

actgcattct agttgtggtt tgtccaaact catcaatgta tcttatcatg tc           2272
```

<210> SEQ ID NO 26
<211> LENGTH: 6335
<212> TYPE: DNA
<213> ORGANISM: Artificial
<220> FEATURE:
<223> OTHER INFORMATION: Synthetic plasmid

<400> SEQUENCE: 26

```
tcgagctcta gattgggaac ccgggtctct cgaattcgag atctccacca tgcacagacc     60

tagacgtcgt ggaactcgtc cacctccact ggcactgctc gctgctctcc tcctggctgc    120

acgtggtgct gatgcagaca tccagatgac ccagtctcca gcctccctgt ctgcatctgt    180

tggagacaga gtcaccatca cttgtcgggc gagtcaggac attagcgatt atttagcctg    240

gtatcagcag aaaccaggga aaattcctag gctcctgatc tatactacat ccactttgca    300

atcaggggtc ccatctcggt tccgtggcag tgggtctggg acagatttca ctctcaccat    360

cagcagcctg cagcctgaag atgttgcaac ttattactgt cagaagtatg acagtgcccc    420

gctcactttc ggcggaggga ccaaggtgga gatcaaacga actgtggctg caccatctgt    480

cttcatcttc ccgccatctg atgagcagtt gaaatctgga actgcctctg ttgtgtgcct    540

gctgaataac ttctatccca gagaggccaa agtacagtgg aaggtggata acgccctcca    600

atcgggtaac tcccaggaga gtgtcacaga gcaggacagc aaggacagca cctacagcct    660

cagcagcacc ctgacgctga gcaaagcaga ctacgagaaa cacaaagtct acgcctgcga    720

agtcacccat cagggcctga gctcgcccgt cacaaagagc ttcaacaggg gagagtgtta    780

ggcggccgct aatcagccat accacatttg tagaggtttt acttgcttta aaaaacctcc    840

cacacctccc cctgaacctg aaacataaaa tgaatgcaat tgttgttgtt aacttgttta    900

ttgcagctta taatggttac aaataaagca atagcatcac aaatttcaca aataaagcat    960

ttttttcact gcattctagt tgtggtttgt ccaaactcat caatgtatct tatcatgtct   1020

accggtaggg cccctctctt catgtgagca aaaggccagc aaaaggccag gaaccgtaaa   1080

aaggccgcgt tgctggcgtt tttccatagg ctccgccccc ctgacgagca tcacaaaaat   1140

cgacgctcaa gtcagaggtg gcgaaacccg acaggactat aaagatacca ggcgtttccc   1200

cctggaagct ccctcgtgcg ctctcctgtt ccgaccctgc cgcttaccgg atacctgtcc   1260

gcctttctcc cttcgggaag cgtggcgctt tctcaatgct cacgctgtag gtatctcagt   1320

tcggtgtagg tcgttcgctc caagctgggc tgtgtgcacg aaccccccgt tcagcccgac   1380

cgctgcgcct tatccggtaa ctatcgtctt gagtccaacc cggtaagaca cgacttatcg   1440

ccactggcag cagccactgg taacaggatt agcagagcga ggtatgtagg cggtgctaca   1500

gagttcttga agtggtggcc taactacggc tacactagaa ggacagtatt tggtatctgc   1560

gctctgctga agccagttac cttcggaaaa agagttggta gctcttgatc cggcaaacaa   1620

accaccgctg gtagcggtgg tttttttgtt tgcaagcagc agattacgcg cagaaaaaaa   1680
```

-continued

```
ggatctcaag aagatccttt gatcttttct acggggtctg acgctcagtg gaacgaaaac   1740
tcacgttaag ggattttggt catgggcgcg ggcatgagat tatcaaaaag gatcttcacc   1800
tagatccttt taaattaaaa atgaagtttt aaatcaatct aaagtatata tgagtaaact   1860
tggtctgaca gttaccaatg cttaatcagt gaggcaccta tctcagcgat ctgtctattt   1920
cgttcatcca tagttgcctg actccccgtc gtgtagataa ctacgatacg ggagggctta   1980
ccatctggcc ccagtgctgc aatgataccg cgagacccac gctcaccggc tccagattta   2040
tcagcaataa accagccagc cggaagggcc gagcgcagaa gtggtcctgc aactttatcc   2100
gcctccatcc agtctattaa ttgttgccgg gaagctagag taagtagttc gccagttaat   2160
agtttgcgca acgttgttgc cattgctaca ggcatcgtgg tgtcacgctc gtcgtttggt   2220
atggcttcat tcagctccgg ttcccaacga tcaaggcgag ttacatgatc ccccatgttg   2280
tgcaaaaaag cggttagctc cttcggtcct ccgatcgttg tcagaagtaa gttggccgca   2340
gtgttatcac tcatggttat ggcagcactg cataattctc ttactgtcat gccatccgta   2400
agatgctttt ctgtgactgg tgagtactca accaagtcat tctgagaata gtgtatgcgg   2460
cgaccgagtt gctcttgccc ggcgtcaata cgggataata ccgcgccaca tagcagaact   2520
ttaaaagtgc tcatcattgg aaaacgttct tcggggcgaa aactctcaag gatcttaccg   2580
ctgttgagat ccagttcgat gtaacccact cgtgcaccca actgatcttc agcatctttt   2640
actttcacca gcgtttctgg gtgagcaaaa acaggaaggc aaaatgccgc aaaaaaggga   2700
ataagggcga cacggaaatg ttgaatactc atactcttcc tttttcaata ttattgaagc   2760
atttatcagg gttattgtct catgagcgga tacatatttg aatgtattta gaaaaataaa   2820
caaatagggg ttccgcgcac atttccccga aaagtgccac ctgacgtcag gtacacttag   2880
gcgcgccatt agagttcctg caggctacat ggtaccaagc ctaggcctcc aaaaaagcct   2940
cctcactact tctggaatag ctcagaggca gaggcggcct cggcctctgc ataaataaaa   3000
aaaattagtc agccatgggg cggagaatgg gcggaactgg gcggagttag gggcgggatg   3060
ggcggagtta ggggcgggac tatggttgct gactaattga gatgcatgct ttgcatactt   3120
ctgcctgctg gggagcctgg ggactttcca cacctggttg ctgactaatt gagatgcatg   3180
ctttgcatac ttctgcctgc tggggagcct ggggactttc cacaccggat ccaccatgga   3240
tagatccgga aagcctgaac tcaccgcgac gtctgtcgag aagtttctga tcgaaaagtt   3300
cgacagcgtc tccgacctga tgcagctctc ggagggcgaa gaatctcgtg ctttcagctt   3360
cgatgtagga gggcgtggat atgtcctgcg ggtaaatagc tgcgccgatg gtttctacaa   3420
agatcgttat gtttatcggc actttgcatc ggccgcgctc ccgattccgg aagtgcttga   3480
cattggggag ttcagcgaga gcctgaccta ttgcatctcc cgccgtgcac agggtgtcac   3540
gttgcaagac ctgcctgaaa ccgaactgcc cgctgttctg cagccggtcg cggaggccat   3600
ggatgcgatc gctgcggccg atcttagcca gacgagcggg ttcggcccat tcggaccgca   3660
aggaatcggt caatacacta catggcgtga tttcatatgc gcgattgctg atccccatgt   3720
gtatcactgg caaactgtga tggacgacac cgtcagtgcg tccgtcgcgc aggctctcga   3780
tgagctgatg ctttgggccg aggactgccc cgaagtccgg cacctcgtgc acgcggattt   3840
cggctccaac aatgtcctga cggacaatgg ccgcataaca gcggtcattg actggagcga   3900
ggcgatgttc ggggattccc aatacgaggt cgccaacatc ttcttctgga ggccgtggtt   3960
ggcttgtatg gagcagcaga cgcgctactt cgagcggagg catccggagc ttgcaggatc   4020
gccgcggctc cgggcgtata tgctccgcat tggtcttgac caactctatc agagcttggt   4080
```

```
tgacggcaat ttcgatgatg cagcttgggc gcagggtcga tgcgacgcaa tcgtccgatc   4140
cggagccggg actgtcgggc gtacacaaat cgcccgcaga agcgcggccg tctggaccga   4200
tggctgtgta gaagtactcg ccgatagtgg aaaccgacgc cccagcactc gtccgagggc   4260
aaaggaatag acgcgtgctg taagtctgca gaaattgatg atctattaaa caataaagat   4320
gtccactaaa atggaagttt ttcctgtcat actttgttaa gaagggtgag aacagagtac   4380
ctacattttg aatggaagga ttggagctac gggggtgggg gtggggtggg attagataaa   4440
tgcctgctct ttactgaagg ctctttacta ttgctttatg ataatgtttc atagttggat   4500
atcataattt aaacaagcaa aaccaaatta agggccagct cattcctccc actcatgatc   4560
tatggatcta tagatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcgggggctc cctttagggt tccgatttag tgctttacgg   4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga cccccgccca ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc cccctattga   5340
cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg gatagcggtt tgactcacgg ggatttccaa gtctccaccc   5520
cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
aagcagagct catgatagaa gcactctact attcgtcgac cgatcctgag aacttcaggg   5700
tgagtttggg gacccttgat tgttctttct ttttcgctat tgtaaaattc atgttatatg   5760
gagggggcaa agttttcagg gtgttgttta gaatgggaag atgtcccttg tatcaccatg   5820
gaccctcatg ataattttgt ttctttcact ttctactctg ttgacaacca ttgtctcctc   5880
ttattttctt ttcattttct gtaacttttt cgttaaactt tagcttgcat ttgtaacgaa   5940
tttttaaatt cacttttgtt tatttgtcag attgtaagta ctttctctaa tcactttttt   6000
ttcaaggcaa tcagggtata ttatattgta cttcagcaca gttttagaga acaattgtta   6060
taattaaatg ataaggtaga atatttctgc atataaattc tggctggcgt ggaaatattc   6120
ttattggtag aaacaactac accctggtca tcatcctgcc tttctcttta tggttacaat   6180
gatatacact gtttgagatg aggataaaat actctgagtc caaaccgggc ccctctgcta   6240
accatgttca tgccttcttc tctttcctac agctcctggg caacgtgctg gttgttgtgc   6300
tgtctcatca ttttggcaaa gaattaagct tatac                              6335
```

<210> SEQ ID NO 27

<211> LENGTH: 452
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Ile His Trp Val Arg Gln Ala Thr Gly Lys Gly Leu Glu Trp Val
35 40 45

Ser Ala Ile Gly Pro Ala Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Gly Leu Ile Thr Phe Gly Gly Leu Ile Ala Pro Phe Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Asp Glu Leu Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro

```
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 28
<211> LENGTH: 112
<212> TYPE: PRT
<213> ORGANISM: Homo sapiens

<400> SEQUENCE: 28

Glu Ser Gly Gly Gly Leu Val Gln Pro Gly Gly Ser Leu Arg Leu Ser
1               5                   10                  15

Cys Ala Ala Ser Gly Phe Thr Phe Ser Ser Tyr Asp Ile His Trp Val
            20                  25                  30

Arg Gln Ala Thr Gly Lys Gly Leu Glu Trp Val Ser Ala Ile Gly Pro
        35                  40                  45

Ala Gly Asp Thr Tyr Tyr Pro Gly Ser Val Lys Gly Arg Phe Thr Ile
    50                  55                  60

Ser Arg Glu Asn Ala Lys Asn Ser Leu Tyr Leu Gln Met Asn Ser Leu
65                  70                  75                  80

Arg Ala Gly Asp Thr Ala Val Tyr Tyr Cys Ala Arg Gly Leu Ile Thr
                85                  90                  95

Phe Gly Gly Leu Ile Ala Pro Phe Asp Tyr Trp Gly Gln Gly Thr Leu
            100                 105                 110


<210> SEQ ID NO 29
<211> LENGTH: 214
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 30
<211> LENGTH: 107
<212> TYPE: PRT
<213> ORGANISM: Homo sapiens

<400> SEQUENCE: 30

Ile Val Leu Thr Gln Ser Pro Gly Thr Leu Ser Leu Ser Pro Gly Glu
1               5                   10                  15

Arg Ala Thr Leu Ser Cys Arg Ala Ser Gln Ser Val Ser Ser Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Asp Asn Ser Gln Thr
                85                  90                  95

Phe Gly Gln Gly Thr Lys Val Glu Ile Lys Arg
            100                 105


<210> SEQ ID NO 31
<211> LENGTH: 2986
<212> TYPE: DNA
<213> ORGANISM: Artificial
<220> FEATURE:
<223> OTHER INFORMATION: Synthetic construct

<400> SEQUENCE: 31

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctca tgatagaagc actctactat tcgtcgaccg    600

atcctgagaa cttcagggtg agtttgggga cccttgattg ttctttcttt ttcgctattg    660

taaaattcat gttatatgga gggggcaaag ttttcagggt gttgtttaga atgggaagat    720

gtcccttgta tcaccatgga ccctcatgat aattttgttt ctttcacttt ctactctgtt    780
```

```
gacaaccatt gtctcctctt attttctttt cattttctgt aactttttcg ttaaacttta    840
gcttgcattt gtaacgaatt tttaaattca cttttgttta tttgtcagat tgtaagtact    900
ttctctaatc actttttttt caaggcaatc agggtatatt atattgtact tcagcacagt    960
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcag aggtgcagct ggtggagtct gggggaggct tggtacagcc gggggggtcc   1440
ctgagactct cctgtgcagc ctctggattc accttcagta gctacgacat acactgggtc   1500
cgtcaagcta caggaaaagg tctggagtgg gtctcagcta ttggtcctgc tggtgacaca   1560
tactatccag gctccgtgaa gggccgattc accatctcca gagaaaatgc caagaactcc   1620
ttgtatcttc aaatgaacag cctgagagcc ggggacacgg ctgtgtatta ctgtgcaaga   1680
ggtttgatta cgtttggggg gcttatcgcc ccgtttgact actggggcca gggaaccctg   1740
gtcaccgtct cctcagcctc caccaagggc ccatcggtct tccccctggc accctcctcc   1800
aagagcacct ctgggggcac agcggccctg ggctgcctgg tcaaggacta cttccccgaa   1860
ccggtgacgg tgtcgtggaa ctcaggcgcc ctgaccagcg gcgtgcacac cttcccggct   1920
gtcctacagt cctcaggact ctactccctc agcagcgtgg tgaccgtgcc ctccagcagc   1980
ttgggcaccc agacctacat ctgcaacgtg aatcacaagc ccagcaacac caaggtggac   2040
aagaaagttg agcccaaatc ttgtgacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac cacaggtgta caccctgccc   2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctacagcaa gctcaccgtg   2640
gacaagagca ggtggcagca ggggaacgtc ttctcatgct ccgtgatgca tgaggctctg   2700
cacaaccact acacgcagaa gtccctctcc ctgtctccgg gtaaatgagc ggccgctaat   2760
cagccatacc acatttgtag aggttttact tgctttaaaa aacctcccac acctccccct   2820
gaacctgaaa cataaaatga atgcaattgt tgttgttaac ttgtttattg cagcttataa   2880
tggttacaaa taaagcaata gcatcacaaa tttcacaaat aaagcatttt tttcactgca   2940
ttctagttgt ggtttgtcca aactcatcaa tgtatcttat catgtc                  2986
```

<210> SEQ ID NO 32
<211> LENGTH: 7028
<212> TYPE: DNA
<213> ORGANISM: Artificial <220> FEATURE:
<223> OTHER INFORMATION: Synthetic plasmid

<400> SEQUENCE: 32 tcgcgatgtg tgactagtta gttattaata gtaatcaatt acggggtcat tagttcatag 60 cccatatatg gagttccgcg ttacataact tacggtaaat ggcccgcctg gctgaccgcc 120 caacgacccc cgcccattga cgtcaataat gacgtatgtt cccatagtaa cgccaatagg 180 gactttccat tgacgtcaat gggtggagta tttacggtaa actgcccact tggcagtaca 240 tcaagtgtat catatgccaa gtacgccccc tattgacgtc aatgacggta aatggcccgc 300 ctggcattat gcccagtaca tgaccttatg ggactttcct acttggcagt acatctacgt 360 attagtcatc gctattacca tggtgatgcg gttttggcag tacatcaatg ggcgtggata 420 gcggtttgac tcacggggat ttccaagtct ccaccccatt gacgtcaatg ggagtttgtt 480 ttggcaccaa aatcaacggg actttccaaa atgtcgtaac aactccgccc cattgacgca 540 aatgggcggt aggcgtgtac ggtgggaggt ctatataagc agagctcatg atagaagcac 600 tctactattc gtcgaccgat cctgagaact tcagggtgag tttggggacc cttgattgtt 660 ctttcttttt cgctattgta aaattcatgt tatatggagg gggcaaagtt ttcagggtgt 720 tgtttagaat gggaagatgt cccttgtatc accatggacc ctcatgataa ttttgtttct 780 ttcactttct actctgttga caaccattgt ctcctcttat tttcttttca ttttctgtaa 840 ctttttcgtt aaactttagc ttgcatttgt aacgaatttt taaattcact tttgtttatt 900 tgtcagattg taagtacttt ctctaatcac tttttttca aggcaatcag ggtatattat 960 attgtacttc agcacagttt tagagaacaa ttgttataat taaatgataa ggtagaatat 1020 ttctgcatat aaattctggc tggcgtggaa atattcttat tggtagaaac aactacaccc 1080 tggtcatcat cctgcctttc tctttatggt tacaatgata tacactgttt gagatgagga 1140 taaaatactc tgagtccaaa ccgggcccct ctgctaacca tgttcatgcc ttcttctctt 1200 tcctacagct cctgggcaac gtgctggttg ttgtgctgtc tcatcatttt ggcaaagaat 1260 taagcttata ctcgagctct agattgggaa cccgggtctc tcgaattcga gatctccacc 1320 atgcacagac ctagacgtcg tggaactcgt ccacctccac tggcactgct cgctgctctc 1380 ctcctggctg cacgtggtgc tgatgcagag gtgcagctgg tggagtctgg gggaggcttg 1440 gtacagccgg gggggtccct gagactctcc tgtgcagcct ctggattcac cttcagtagc 1500 tacgacatac actgggtccg tcaagctaca ggaaaaggtc tggagtgggt ctcagctatt 1560 ggtcctgctg gtgacacata ctatccaggc tccgtgaagg gccgattcac catctccaga 1620 gaaaatgcca agaactcctt gtatcttcaa atgaacagcc tgagagccgg ggacacggct 1680 gtgtattact gtgcaagagg tttgattacg tttgggggc ttatcgcccc gtttgactac 1740 tggggccagg gaaccctggt caccgtctcc tcagcctcca ccaagggccc atcggtcttc 1800 cccctggcac cctcctccaa gagcacctct gggggcacag cggccctggg ctgcctggtc 1860 aaggactact tccccgaacc ggtgacggtg tcgtggaact caggcgccct gaccagcggc 1920 gtgcacacct tcccggctgt cctacagtcc tcaggactct actccctcag cagcgtggtg 1980 accgtgccct ccagcagctt gggcacccag acctacatct gcaacgtgaa tcacaagccc 2040 agcaacacca aggtggacaa gaaagttgag cccaaatctt gtgacaaaac tcacacatgc 2100 ccaccgtgcc cagcacctga actcctgggg ggaccgtcag tcttcctctt ccccccaaaa 2160 cccaaggaca ccctcatgat ctcccggacc cctgaggtca catgcgtggt ggtggacgtg 2220

-continued

```
agccacgaag accctgaggt caagttcaac tggtacgtgg acggcgtgga ggtgcataat   2280
gccaagacaa agccgcggga ggagcagtac aacagcacgt accgtgtggt cagcgtcctc   2340
accgtcctgc accaggactg gctgaatggc aaggagtaca agtgcaaggt ctccaacaaa   2400
gccctcccag cccccatcga gaaaaccatc tccaaagcca aagggcagcc ccgagaacca   2460
caggtgtaca ccctgccccc atcccgggat gagctgacca agaaccaggt cagcctgacc   2520
tgcctggtca aaggcttcta tcccagcgac atcgccgtgg agtgggagag caatgggcag   2580
ccggagaaca actacaagac cacgcctccc gtgctggact ccgacggctc cttcttcctc   2640
tacagcaagc tcaccgtgga caagagcagg tggcagcagg ggaacgtctt ctcatgctcc   2700
gtgatgcatg aggctctgca caaccactac acgcagaagt ccctctccct gtctccgggt   2760
aaatgagcgg ccgctaatca gccataccac atttgtagag gttttacttg ctttaaaaaa   2820
cctcccacac ctccccctga acctgaaaca taaaatgaat gcaattgttg ttgttaactt   2880
gtttattgca gcttataatg gttacaaata aagcaatagc atcacaaatt tcacaaataa   2940
agcatttttt tcactgcatt ctagttgtgg tttgtccaaa ctcatcaatg tatcttatca   3000
tgtctaccgg tcctgcaggg cccctctctt catgtgagca aaaggccagc aaaaggccag   3060
gaaccgtaaa aaggccgcgt tgctggcgtt tttccatagg ctccgccccc ctgacgagca   3120
tcacaaaaat cgacgctcaa gtcagaggtg gcgaaacccg acaggactat aaagatacca   3180
ggcgtttccc cctggaagct ccctcgtgcg ctctcctgtt ccgaccctgc cgcttaccgg   3240
atacctgtcc gcctttctcc cttcgggaag cgtggcgctt tctcaatgct cacgctgtag   3300
gtatctcagt tcggtgtagg tcgttcgctc caagctgggc tgtgtgcacg aaccccccgt   3360
tcagcccgac cgctgcgcct tatccggtaa ctatcgtctt gagtccaacc cggtaagaca   3420
cgacttatcg ccactggcag cagccactgg taacaggatt agcagagcga ggtatgtagg   3480
cggtgctaca gagttcttga agtggtggcc taactacggc tacactagaa ggacagtatt   3540
tggtatctgc gctctgctga agccagttac cttcggaaaa agagttggta gctcttgatc   3600
cggcaaacaa accaccgctg gtagcggtgg tttttttgtt tgcaagcagc agattacgcg   3660
cagaaaaaaa ggatctcaag aagatccttt gatcttttct acggggtctg acgctcagtg   3720
gaacgaaaac tcacgttaag ggattttggt catgggcgcg cctcatactc ctgcaggcat   3780
gagattatca aaaaggatct tcacctagat ccttttaaat taaaaatgaa gttttaaatc   3840
aatctaaagt atatatgagt aaacttggtc tgacagttac caatgcttaa tcagtgaggc   3900
acctatctca gcgatctgtc tatttcgttc atccatagtt gcctgactcc ccgtcgtgta   3960
gataactacg atacgggagg gcttaccatc tggccccagt gctgcaatga taccgcgaga   4020
cccacgctca ccggctccag atttatcagc aataaaccag ccagccggaa gggccgagcg   4080
cagaagtggt cctgcaactt tatccgcctc catccagtct attaattgtt gccgggaagc   4140
tagagtaagt agttcgccag ttaatagttt gcgcaacgtt gttgccattg ctacaggcat   4200
cgtggtgtca cgctcgtcgt ttggtatggc ttcattcagc tccggttccc aacgatcaag   4260
gcgagttaca tgatccccca tgttgtgcaa aaaagcggtt agctccttcg gtcctccgat   4320
cgttgtcaga agtaagttgg ccgcagtgtt atcactcatg gttatggcag cactgcataa   4380
ttctcttact gtcatgccat ccgtaagatg cttttctgtg actggtgagt actcaaccaa   4440
gtcattctga gaatagtgta tgcggcgacc gagttgctct tgcccggcgt caatacggga   4500
taataccgcg ccacatagca gaactttaaa agtgctcatc attggaaaac gttcttcggg   4560
gcgaaaactc tcaaggatct taccgctgtt gagatccagt tcgatgtaac ccactcgtgc   4620
```

acccaactga tcttcagcat cttttacttt caccagcgtt tctgggtgag caaaaacagg 4680
aaggcaaaat gccgcaaaaa agggaataag ggcgacacgg aaatgttgaa tactcatact 4740
cttccttttt caatattatt gaagcattta tcagggttat tgtctcatga gcggatacat 4800
atttgaatgt atttagaaaa ataaacaaat aggggttccg cgcacatttc cccgaaaagt 4860
gccacctgac gtcaggtacc aagcctaggc ctccaaaaaa gcctcctcac tacttctgga 4920
atagctcaga ggcagaggcg gcctcggcct ctgcataaat aaaaaaaatt agtcagccat 4980
ggggcggaga atgggcggaa ctgggcggag ttaggggcgg gatgggcgga gttaggggcg 5040
ggactatggt tgctgactaa ttgagatgca tgctttgcat acttctgcct gctggggagc 5100
ctggggactt tccacacctg gttgctgact aattgagatg catgctttgc atacttctgc 5160
ctgctgggga gcctggggac tttccacacc ggatccacca tggatagatc cggaaagcct 5220
gaactcaccg cgacgtctgt cgagaagttt ctgatcgaaa agttcgacag cgtctccgac 5280
ctgatgcagc tctcggaggg cgaagaatct cgtgctttca gcttcgatgt aggagggcgt 5340
ggatatgtcc tgcgggtaaa tagctgcgcc gatggtttct acaaagatcg ttatgtttat 5400
cggcactttg catcggccgc gctcccgatt ccggaagtgc ttgacattgg ggagttcagc 5460
gagagcctga cctattgcat ctcccgccgt gcacagggtg tcacgttgca agacctgcct 5520
gaaaccgaac tgcccgctgt tctgcagccg gtcgcggagg ccatggatgc gatcgctgcg 5580
gccgatctta gccagacgag cgggttcggc ccattcggac cgcaaggaat cggtcaatac 5640
actacatggc gtgatttcat atgcgcgatt gctgatcccc atgtgtatca ctggcaaact 5700
gtgatggacg acaccgtcag tgcgtccgtc gcgcaggctc tcgatgagct gatgctttgg 5760
gccgaggact gccccgaagt ccggcacctc gtgcacgcgg atttcggctc caacaatgtc 5820
ctgacggaca atggccgcat aacagcggtc attgactgga gcgaggcgat gttcggggat 5880
tcccaatacg aggtcgccaa catcttcttc tggaggccgt ggttggcttg tatggagcag 5940
cagacgcgct acttcgagcg gaggcatccg gagcttgcag gatcgccgcg gctccgggcg 6000
tatatgctcc gcattggtct tgaccaactc tatcagagct tggttgacgg caatttcgat 6060
gatgcagctt gggcgcaggg tcgatgcgac gcaatcgtcc gatccggagc cgggactgtc 6120
gggcgtacac aaatcgcccg cagaagcgcg gccgtctgga ccgatggctg tgtagaagta 6180
ctcgccgata gtggaaaccg acgccccagc actcgtccga gggcaaagga atagacgcgt 6240
gctgtaagtc tgcagaaatt gatgatctat taaacaataa agatgtccac taaaatggaa 6300
gtttttcctg tcatactttg ttaagaaggg tgagaacaga gtacctacat tttgaatgga 6360
aggattggag ctacgggggt gggggtgggg tgggattaga taaatgcctg ctctttactg 6420
aaggctcttt actattgctt tatgataatg tttcatagtt ggatatcata atttaaacaa 6480
gcaaaaccaa attaagggcc agctcattcc tcccactcat gatctatgga tctatagatc 6540
tctcgtgcag ctggggctct agggggtatc cccacgcgcc ctgtagcggc gcattaagcg 6600
cggcgggtgt ggtggttacg cgcagcgtga ccgctacact tgccagcgcc ctagcgcccg 6660
ctcctttcgc tttcttccct tcctttctcg ccacgttcgc cggctttccc cgtcaagctc 6720
taaatcgggg gctcccttta gggttccgat ttagtgcttt acggcacctc gaccccaaaa 6780
aacttgatta gggtgatggt tcacgtagtg ggccatcgcc ctgatagacg gtttttcgcc 6840
ctttgacgtt ggagtccacg ttctttaata gtggactctt gttccaaact ggaacaacac 6900
tcaaccctat ctcggtctat tcttttgatt tataagggat tttgccgatt tcggcctatt 6960

```
ggttaaaaaa tgagctgatt taacaaaaat ttaacgcgaa ttaattctgt ggaatgtgtg   7020

tcagttag                                                            7028


<210> SEQ ID NO 33
<211> LENGTH: 2272
<212> TYPE: DNA
<213> ORGANISM: Artificial
<220> FEATURE:
<223> OTHER INFORMATION: Synthetic construct

<400> SEQUENCE: 33

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctca tgatagaagc actctactat tcgtcgaccg    600

atcctgagaa cttcagggtg agtttgggga cccttgattg ttctttcttt ttcgctattg    660

taaaattcat gttatatgga gggggcaaag ttttcagggt gttgtttaga atgggaagat    720

gtcccttgta tcaccatgga ccctcatgat aattttgttt ctttcacttt ctactctgtt    780

gacaaccatt gtctcctctt attttctttt cattttctgt aactttttcg ttaaacttta    840

gcttgcattt gtaacgaatt tttaaattca cttttgttta tttgtcagat tgtaagtact    900

ttctctaatc actttttttt caaggcaatc agggtatatt atattgtact tcagcacagt    960

tttagagaac aattgttata attaaatgat aaggtagaat atttctgcat ataaattctg   1020

gctggcgtgg aaatattctt attggtagaa acaactacac cctggtcatc atcctgcctt   1080

tctctttatg gttacaatga tatacactgt ttgagatgag gataaaatac tctgagtcca   1140

aaccgggccc ctctgctaac catgttcatg ccttcttctc tttcctacag ctcctgggca   1200

acgtgctggt tgttgtgctg tctcatcatt ttggcaaaga attaagctta tactcgagct   1260

ctagattggg aacccgggtc tctcgaattc gagatctcca ccatgcacag acctagacgt   1320

cgtggaactc gtccacctcc actggcactg ctcgctgctc tcctcctggc tgcacgtggt   1380

gctgatgcag aaattgtgtt gacgcagtct ccaggcaccc tgtctttgtc tccaggggaa   1440

agagccaccc tctcctgcag ggccagtcag agtgttagca gcacctactt agcctggtac   1500

cagcagaaac ctggccaggc tcccaggctc ctcatctatg gtgcatccag cagggccact   1560

ggcatcccag acaggttcag tggcagtggg tctgggacag acttcactct caccatcagc   1620

agactggagc ctgaagattt tgcagtgtat tactgtcagc attatgataa ctcacaaacg   1680

ttcggccaag ggaccaaggt ggagatcaaa cgaactgtgg ctgcaccatc tgtcttcatc   1740

ttcccgccat ctgatgagca gttgaaatct ggaactgcct ctgttgtgtg cctgctgaat   1800

aacttctatc ccagagaggc caaagtacag tggaaggtgg ataacgccct ccaatcgggt   1860

aactcccagg agagtgtcac agagcaggac agcaaggaca gcacctacag cctcagcagc   1920

accctgacgc tgagcaaagc agactacgag aaacacaaag tctacgcctg cgaagtcacc   1980
```

```
catcagggcc tgagctcgcc cgtcacaaag agcttcaaca ggggagagtg ttaggcggcc   2040

gctaatcagc cataccacat ttgtagaggt tttacttgct ttaaaaaacc tcccacacct   2100

ccccctgaac ctgaaacata aaatgaatgc aattgttgtt gttaacttgt ttattgcagc   2160

ttataatggt tacaaataaa gcaatagcat cacaaatttc acaaataaag catttttttc   2220

actgcattct agttgtggtt tgtccaaact catcaatgta tcttatcatg tc           2272
```

<210> SEQ ID NO 34
<211> LENGTH: 6335
<212> TYPE: DNA
<213> ORGANISM: Artificial
<220> FEATURE:
<223> OTHER INFORMATION: Synthetic plasmid

<400> SEQUENCE: 34

```
tcgagctcta gattgggaac ccgggtctct cgaattcgag atctccacca tgcacagacc     60

tagacgtcgt ggaactcgtc cacctccact ggcactgctc gctgctctcc tcctggctgc    120

acgtggtgct gatgcagaaa ttgtgttgac gcagtctcca ggcaccctgt ctttgtctcc    180

aggggaaaga gccaccctct cctgcagggc cagtcagagt gttagcagca cctacttagc    240

ctggtaccag cagaaacctg gccaggctcc caggctcctc atctatggtg catccagcag    300

ggccactggc atcccagaca ggttcagtgg cagtgggtct gggacagact tcactctcac    360

catcagcaga ctggagcctg aagattttgc agtgtattac tgtcagcatt atgataactc    420

acaaacgttc ggccaaggga ccaaggtgga gatcaaacga actgtggctg caccatctgt    480

cttcatcttc ccgccatctg atgagcagtt gaaatctgga actgcctctg ttgtgtgcct    540

gctgaataac ttctatccca gagaggccaa agtacagtgg aaggtggata acgccctcca    600

atcgggtaac tcccaggaga gtgtcacaga gcaggacagc aaggacagca cctacagcct    660

cagcagcacc ctgacgctga gcaaagcaga ctacgagaaa cacaaagtct acgcctgcga    720

agtcacccat cagggcctga gctcgcccgt cacaaagagc ttcaacaggg gagagtgtta    780

ggcggccgct aatcagccat accacatttg tagaggtttt acttgcttta aaaaacctcc    840

cacacctccc cctgaacctg aaacataaaa tgaatgcaat tgttgttgtt aacttgttta    900

ttgcagctta taatggttac aaataaagca atagcatcac aaatttcaca aataaagcat    960

ttttttcact gcattctagt tgtggtttgt ccaaactcat caatgtatct tatcatgtct   1020

accggtaggg cccctctctt catgtgagca aaaggccagc aaaaggccag gaaccgtaaa   1080

aaggccgcgt tgctggcgtt tttccatagg ctccgccccc ctgacgagca tcacaaaaat   1140

cgacgctcaa gtcagaggtg gcgaaacccg acaggactat aaagatacca ggcgtttccc   1200

cctggaagct ccctcgtgcg ctctcctgtt ccgaccctgc cgcttaccgg atacctgtcc   1260

gcctttctcc cttcgggaag cgtggcgctt tctcaatgct cacgctgtag gtatctcagt   1320

tcggtgtagg tcgttcgctc caagctgggc tgtgtgcacg aaccccccgt tcagcccgac   1380

cgctgcgcct tatccggtaa ctatcgtctt gagtccaacc cggtaagaca cgacttatcg   1440

ccactggcag cagccactgg taacaggatt agcagagcga ggtatgtagg cggtgctaca   1500

gagttcttga agtggtggcc taactacggc tacactagaa ggacagtatt tggtatctgc   1560

gctctgctga agccagttac cttcggaaaa agagttggta gctcttgatc cggcaaacaa   1620

accaccgctg gtagcggtgg tttttttgtt tgcaagcagc agattacgcg cagaaaaaaa   1680

ggatctcaag aagatccttt gatcttttct acggggtctg acgctcagtg gaacgaaaac   1740
```

```
tcacgttaag ggattttggt catgggcgcg ggcatgagat tatcaaaaag gatcttcacc   1800
tagatccttt taaattaaaa atgaagtttt aaatcaatct aaagtatata tgagtaaact   1860
tggtctgaca gttaccaatg cttaatcagt gaggcaccta tctcagcgat ctgtctattt   1920
cgttcatcca tagttgcctg actccccgtc gtgtagataa ctacgatacg ggagggctta   1980
ccatctggcc ccagtgctgc aatgataccg cgagacccac gctcaccggc tccagattta   2040
tcagcaataa accagccagc cggaagggcc gagcgcagaa gtggtcctgc aactttatcc   2100
gcctccatcc agtctattaa ttgttgccgg gaagctagag taagtagttc gccagttaat   2160
agtttgcgca acgttgttgc cattgctaca ggcatcgtgg tgtcacgctc gtcgtttggt   2220
atggcttcat tcagctccgg ttcccaacga tcaaggcgag ttacatgatc ccccatgttg   2280
tgcaaaaaag cggttagctc cttcggtcct ccgatcgttg tcagaagtaa gttggccgca   2340
gtgttatcac tcatggttat ggcagcactg cataattctc ttactgtcat gccatccgta   2400
agatgctttt ctgtgactgg tgagtactca accaagtcat tctgagaata gtgtatgcgg   2460
cgaccgagtt gctcttgccc ggcgtcaata cgggataata ccgcgccaca tagcagaact   2520
ttaaaagtgc tcatcattgg aaaacgttct tcggggcgaa aactctcaag gatcttaccg   2580
ctgttgagat ccagttcgat gtaacccact cgtgcaccca actgatcttc agcatctttt   2640
actttcacca gcgtttctgg gtgagcaaaa acaggaaggc aaaatgccgc aaaaaaggga   2700
ataagggcga cacggaaatg ttgaatactc atactcttcc tttttcaata ttattgaagc   2760
atttatcagg gttattgtct catgagcgga tacatatttg aatgtattta gaaaaataaa   2820
caaatagggg ttccgcgcac atttccccga aaagtgccac ctgacgtcag gtacacttag   2880
gcgcgccatt agagttcctg caggctacat ggtaccaagc ctaggcctcc aaaaaagcct   2940
cctcactact tctggaatag ctcagaggca gaggcggcct cggcctctgc ataaataaaa   3000
aaaattagtc agccatgggg cggagaatgg gcggaactgg gcggagttag gggcgggatg   3060
ggcggagtta ggggcgggac tatggttgct gactaattga gatgcatgct ttgcatactt   3120
ctgcctgctg gggagcctgg ggactttcca cacctggttg ctgactaatt gagatgcatg   3180
ctttgcatac ttctgcctgc tggggagcct ggggactttc cacaccggat ccaccatgga   3240
tagatccgga aagcctgaac tcaccgcgac gtctgtcgag aagtttctga tcgaaaagtt   3300
cgacagcgtc tccgacctga tgcagctctc ggagggcgaa gaatctcgtg ctttcagctt   3360
cgatgtagga gggcgtggat atgtcctgcg ggtaaatagc tgcgccgatg gtttctacaa   3420
agatcgttat gtttatcggc actttgcatc ggccgcgctc ccgattccgg aagtgcttga   3480
cattggggag ttcagcgaga gcctgaccta ttgcatctcc cgccgtgcac agggtgtcac   3540
gttgcaagac ctgcctgaaa ccgaactgcc cgctgttctg cagccggtcg cggaggccat   3600
ggatgcgatc gctgcggccg atcttagcca gacgagcggg ttcggcccat tcggaccgca   3660
aggaatcggt caatacacta catggcgtga tttcatatgc gcgattgctg atccccatgt   3720
gtatcactgg caaactgtga tggacgacac cgtcagtgcg tccgtcgcgc aggctctcga   3780
tgagctgatg ctttgggccg aggactgccc cgaagtccgg cacctcgtgc acgcggattt   3840
cggctccaac aatgtcctga cggacaatgg ccgcataaca gcggtcattg actggagcga   3900
ggcgatgttc ggggattccc aatacgaggt cgccaacatc ttcttctgga ggccgtggtt   3960
ggcttgtatg gagcagcaga cgcgctactt cgagcggagg catccggagc ttgcaggatc   4020
gccgcggctc cgggcgtata tgctccgcat tggtcttgac caactctatc agagcttggt   4080
tgacggcaat ttcgatgatg cagcttgggc gcagggtcga tgcgacgcaa tcgtccgatc   4140
```

```
cggagccggg actgtcgggc gtacacaaat cgcccgcaga agcgcggccg tctggaccga   4200
tggctgtgta gaagtactcg ccgatagtgg aaaccgacgc cccagcactc gtccgagggc   4260
aaaggaatag acgcgtgctg taagtctgca gaaattgatg atctattaaa caataaagat   4320
gtccactaaa atggaagttt ttcctgtcat actttgttaa gaagggtgag aacagagtac   4380
ctacattttg aatggaagga ttggagctac gggggtgggg gtggggtggg attagataaa   4440
tgcctgctct ttactgaagg ctctttacta ttgctttatg ataatgtttc atagttggat   4500
atcataattt aaacaagcaa aaccaaatta agggccagct cattcctccc actcatgatc   4560
tatggatcta tagatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcgggggctc cctttagggt tccgatttag tgctttacgg   4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga cccccgccca ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc cccctattga   5340
cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg gatagcggtt tgactcacgg ggatttccaa gtctccaccc   5520
cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
aagcagagct catgatagaa gcactctact attcgtcgac cgatcctgag aacttcaggg   5700
tgagtttggg gacccttgat tgttctttct ttttcgctat tgtaaaattc atgttatatg   5760
gagggggcaa agttttcagg gtgttgttta gaatgggaag atgtcccttg tatcaccatg   5820
gaccctcatg ataattttgt ttctttcact ttctactctg ttgacaacca ttgtctcctc   5880
ttattttctt ttcattttct gtaacttttt cgttaaactt tagcttgcat ttgtaacgaa   5940
tttttaaatt cacttttgtt tatttgtcag attgtaagta ctttctctaa tcactttttt   6000
ttcaaggcaa tcagggtata ttatattgta cttcagcaca gttttagaga acaattgtta   6060
taattaaatg ataaggtaga atatttctgc atataaattc tggctggcgt ggaaatattc   6120
ttattggtag aaacaactac accctggtca tcatcctgcc tttctcttta tggttacaat   6180
gatatacact gtttgagatg aggataaaat actctgagtc caaaccgggc ccctctgcta   6240
accatgttca tgccttcttc tctttcctac agctcctggg caacgtgctg gttgttgtgc   6300
tgtctcatca ttttggcaaa gaattaagct tatac                              6335
```

<210> SEQ ID NO 35
<211> LENGTH: 449
<212> TYPE: PRT

<213> ORGANISM: Homo sapiens

<400> SEQUENCE: 35

```
Gln Val Gln Leu Gln Gln Ser Gly Ala Gly Leu Leu Lys Pro Ser Glu
1               5                   10                  15

Thr Leu Ser Leu Thr Cys Thr Val Tyr Gly Gly Ser Phe Ser Ile His
            20                  25                  30

His Trp Thr Trp Ile Arg His Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ala Val Thr Ala Ala Asp Thr Ala Val Tyr Tyr Cys Ala
                85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 36
<211> LENGTH: 103
<212> TYPE: PRT
<213> ORGANISM: Homo sapiens

<400> SEQUENCE: 36

Gln Ser Gly Ala Gly Leu Leu Lys Pro Ser Glu Thr Leu Ser Leu Thr
1               5                   10                  15

Cys Thr Val Tyr Gly Gly Ser Phe Ser Ile His His Trp Thr Trp Ile
            20                  25                  30

Arg His Pro Pro Gly Lys Gly Leu Glu Trp Ile Gly Glu Ile Asn His
        35                  40                  45

Arg Gly Ser Thr Asn Tyr Asn Pro Ser Leu Lys Ser Arg Val Thr Ile
    50                  55                  60

Ser Ile Asp Thr Ser Lys Asn Gln Phe Ser Leu Lys Leu Ser Ala Val
65                  70                  75                  80

Thr Ala Ala Asp Thr Ala Val Tyr Tyr Cys Ala Arg Gly Leu Arg Phe
                85                  90                  95

Leu Asp Trp Leu Ser Ser Tyr
            100


<210> SEQ ID NO 37
<211> LENGTH: 214
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asp Tyr
            20                  25                  30

Leu Ala Trp Tyr Gln Gln Lys Pro Gly Lys Val Pro Asn Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Thr Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 38
<211> LENGTH: 107
<212> TYPE: PRT
<213> ORGANISM: Homo sapiens

<400> SEQUENCE: 38

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Ser Asp Tyr Leu
            20                  25                  30

Ala Trp Tyr Gln Gln Lys Pro Gly Lys Val Pro Asn Leu Leu Ile Tyr
        35                  40                  45

Ala Ala Ser Ala Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Asn Tyr Asn Thr Ala Pro Leu Thr
                85                  90                  95

Phe Gly Gly Gly Thr Lys Val Glu Ile Lys Arg
            100                 105


<210> SEQ ID NO 39
<211> LENGTH: 2977
<212> TYPE: DNA
<213> ORGANISM: Artificial
<220> FEATURE:
<223> OTHER INFORMATION: Synthetic construct

<400> SEQUENCE: 39

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctca tgatagaagc actctactat tcgtcgaccg    600

atcctgagaa cttcagggtg agtttgggga cccttgattg ttctttcttt ttcgctattg    660

taaaattcat gttatatgga gggggcaaag ttttcagggt gttgtttaga atgggaagat    720

gtcccttgta tcaccatgga ccctcatgat aattttgttt ctttcacttt ctactctgtt    780

gacaaccatt gtctcctctt attttctttt cattttctgt aactttttcg ttaaacttta    840

gcttgcattt gtaacgaatt tttaaattca cttttgttta tttgtcagat tgtaagtact    900
```

```
ttctctaatc actttttttt caaggcaatc agggtatatt atattgtact tcagcacagt    960
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcac aggtacagct gcagcagtcg ggcgcaggac tgttgaagcc ttcggagacc   1440
ctgtccctca cctgcactgt ctatggtgga tccttcagta ttcatcactg gacctggatc   1500
cgccatcccc cagggaaggg gctggagtgg attggggaga tcaatcatcg tggaagcacc   1560
aactacaacc cgtccctcaa gagtcgagtc accatatcaa tagacacgtc caagaaccag   1620
ttctccctga agctgagcgc tgtgaccgcc gcggacacgg ctgtatatta ctgtgcgaga   1680
ggcttacgat ttttggactg gttatcgtcc tactttgact actggggcca gggaaccctg   1740
gtcaccgtct cctcagcctc caccaagggc ccatcggtct tccccctggc gccctgctcc   1800
aggagcacct ccgagagcac agccgccctg ggctgcctgg tcaaggacta cttccccgaa   1860
ccggtgacgg tgtcgtggaa ctcaggcgcc ctgaccagcg gcgtgcacac cttcccggct   1920
gtcctacagt cctcaggact ctactccctc agcagcgtgg tgaccgtgcc ctccagcagc   1980
ttgggcacga agacctacac ctgcaacgta gatcacaagc ccagcaacac caaggtggac   2040
aagagagttg agtccaaata tggtccccca tgcccaccct gcccagcacc tgagttcctg   2100
gggggaccat cagtcttcct gttcccccca aaacccaagg acactctcat gatctcccgg   2160
acccctgagg tcacgtgcgt ggtggtggac gtgagccagg aagaccccga ggtccagttc   2220
aactggtacg tggatggcgt ggaggtgcat aatgccaaga caaagccgcg ggaggagcag   2280
ttcaacagca cgtaccgtgt ggtcagcgtc ctcaccgtcc tgcaccagga ctggctgaac   2340
ggcaaggagt acaagtgcaa ggtctccaac aaaggcctcc cgtcctccat cgagaaaacc   2400
atctccaaag ccaaagggca gccccgagag ccacaggtgt acaccctgcc cccatcccag   2460
gaggagatga ccaagaacca ggtcagcctg acctgcctgg tcaaaggctt ctaccccagc   2520
gacatcgccg tggagtggga gagcaatggg cagccggaga acaactacaa gaccacgcct   2580
cccgtgctgg actccgacgg ctccttcttc ctctacagca ggctcaccgt ggacaagagc   2640
aggtggcagg aggggaatgt cttctcatgc tccgtgatgc atgaggctct gcacaaccac   2700
tacacacaga agtccctctc cctgtctctg ggtaaatgag cggccgctaa tcagccatac   2760
cacatttgta gaggttttac ttgctttaaa aaacctccca cacctccccc tgaacctgaa   2820
acataaaatg aatgcaattg ttgttgttaa cttgtttatt gcagcttata atggttacaa   2880
ataaagcaat agcatcacaa atttcacaaa taaagcattt ttttcactgc attctagttg   2940
tggtttgtcc aaactcatca atgtatctta tcatgtc                            2977
```

<210> SEQ ID NO 40
<211> LENGTH: 7019
<212> TYPE: DNA
<213> ORGANISM: Artificial
<220> FEATURE:
<223> OTHER INFORMATION: Synthetic plasmid

<400> SEQUENCE: 40 tcgcgatgtg tgactagtta gttattaata gtaatcaatt acggggtcat tagttcatag 60 cccatatatg gagttccgcg ttacataact tacggtaaat ggcccgcctg gctgaccgcc 120 caacgacccc cgcccattga cgtcaataat gacgtatgtt cccatagtaa cgccaatagg 180 gactttccat tgacgtcaat gggtggagta tttacggtaa actgcccact tggcagtaca 240 tcaagtgtat catatgccaa gtacgccccc tattgacgtc aatgacggta aatggcccgc 300 ctggcattat gcccagtaca tgaccttatg ggactttcct acttggcagt acatctacgt 360 attagtcatc gctattacca tggtgatgcg gttttggcag tacatcaatg ggcgtggata 420 gcggtttgac tcacggggat ttccaagtct ccaccccatt gacgtcaatg ggagtttgtt 480 ttggcaccaa aatcaacggg actttccaaa atgtcgtaac aactccgccc cattgacgca 540 aatgggcggt aggcgtgtac ggtgggaggt ctatataagc agagctcatg atagaagcac 600 tctactattc gtcgaccgat cctgagaact tcagggtgag tttggggacc cttgattgtt 660 ctttcttttt cgctattgta aaattcatgt tatatggagg gggcaaagtt ttcagggtgt 720 tgtttagaat gggaagatgt cccttgtatc accatggacc ctcatgataa ttttgtttct 780 ttcactttct actctgttga caaccattgt ctcctcttat tttcttttca ttttctgtaa 840 ctttttcgtt aaactttagc ttgcatttgt aacgaatttt taaattcact tttgtttatt 900 tgtcagattg taagtacttt ctctaatcac tttttttca aggcaatcag ggtatattat 960 attgtacttc agcacagttt tagagaacaa ttgttataat taaatgataa ggtagaatat 1020 ttctgcatat aaattctggc tggcgtggaa atattcttat tggtagaaac aactacaccc 1080 tggtcatcat cctgcctttc tctttatggt tacaatgata tacactgttt gagatgagga 1140 taaaatactc tgagtccaaa ccgggcccct ctgctaacca tgttcatgcc ttcttctctt 1200 tcctacagct cctgggcaac gtgctggttg ttgtgctgtc tcatcatttt ggcaaagaat 1260 taagcttata ctcgagctct agattgggaa cccgggtctc tcgaattcga gatctccacc 1320 atgcacagac ctagacgtcg tggaactcgt ccacctccac tggcactgct cgctgctctc 1380 ctcctggctg cacgtggtgc tgatgcacag gtacagctgc agcagtcggg cgcaggactg 1440 ttgaagcctt cggagaccct gtccctcacc tgcactgtct atggtggatc cttcagtatt 1500 catcactgga cctggatccg ccatccccca gggaaggggc tggagtggat tggggagatc 1560 aatcatcgtg gaagcaccaa ctacaacccg tccctcaaga gtcgagtcac catatcaata 1620 gacacgtcca agaaccagtt ctccctgaag ctgagcgctg tgaccgccgc ggacacggct 1680 gtatattact gtgcgagagg cttacgattt ttggactggt tatcgtccta ctttgactac 1740 tggggccagg gaaccctggt caccgtctcc tcagcctcca ccaagggccc atcggtcttc 1800 cccctggcgc cctgctccag gagcacctcc gagagcacag ccgccctggg ctgcctggtc 1860 aaggactact tccccgaacc ggtgacggtg tcgtggaact caggcgccct gaccagcggc 1920 gtgcacacct tcccggctgt cctacagtcc tcaggactct actccctcag cagcgtggtg 1980 accgtgccct ccagcagctt gggcacgaag acctacacct gcaacgtaga tcacaagccc 2040 agcaacacca aggtggacaa gagagttgag tccaaatatg gtccccccatg cccaccctgc 2100 ccagcacctg agttcctggg gggaccatca gtcttcctgt tccccccaaa acccaaggac 2160 actctcatga tctcccggac ccctgaggtc acgtgcgtgg tggtggacgt gagccaggaa 2220 gaccccgagg tccagttcaa ctggtacgtg gatggcgtgg aggtgcataa tgccaagaca 2280 aagccgcggg aggagcagtt caacagcacg taccgtgtgg tcagcgtcct caccgtcctg 2340 caccaggact ggctgaacgg caaggagtac aagtgcaagg tctccaacaa aggcctcccg 2400
tcctccatcg agaaaaccat ctccaaagcc aaagggcagc cccgagagcc acaggtgtac 2460
accctgcccc catcccagga ggagatgacc aagaaccagg tcagcctgac ctgcctggtc 2520
aaaggcttct accccagcga catcgccgtg gagtgggaga gcaatgggca gccggagaac 2580
aactacaaga ccacgcctcc cgtgctggac tccgacggct ccttcttcct ctacagcagg 2640
ctcaccgtgg acaagagcag gtggcaggag gggaatgtct tctcatgctc cgtgatgcat 2700
gaggctctgc acaaccacta cacacagaag tccctctccc tgtctctggg taaatgagcg 2760
gccgctaatc agccatacca catttgtaga ggttttactt gctttaaaaa acctcccaca 2820
cctccccctg aacctgaaac ataaaatgaa tgcaattgtt gttgttaact tgtttattgc 2880
agcttataat ggttacaaat aaagcaatag catcacaaat ttcacaaata aagcattttt 2940
ttcactgcat tctagttgtg gtttgtccaa actcatcaat gtatcttatc atgtctaccg 3000
gtcctgcagg gcccctctct tcatgtgagc aaaaggccag caaaaggcca ggaaccgtaa 3060
aaaggccgcg ttgctggcgt ttttccatag gctccgcccc cctgacgagc atcacaaaaa 3120
tcgacgctca agtcagaggt ggcgaaaccc gacaggacta taaagatacc aggcgtttcc 3180
ccctggaagc tccctcgtgc gctctcctgt tccgaccctg ccgcttaccg gatacctgtc 3240
cgcctttctc ccttcgggaa gcgtggcgct ttctcaatgc tcacgctgta ggtatctcag 3300
ttcggtgtag gtcgttcgct ccaagctggg ctgtgtgcac gaaccccccg ttcagcccga 3360
ccgctgcgcc ttatccggta actatcgtct tgagtccaac ccggtaagac acgacttatc 3420
gccactggca gcagccactg gtaacaggat tagcagagcg aggtatgtag gcggtgctac 3480
agagttcttg aagtggtggc ctaactacgg ctacactaga aggacagtat ttggtatctg 3540
cgctctgctg aagccagtta ccttcggaaa aagagttggt agctcttgat ccggcaaaca 3600
aaccaccgct ggtagcggtg gtttttttgt ttgcaagcag cagattacgc gcagaaaaaa 3660
aggatctcaa gaagatcctt tgatcttttc tacggggtct gacgctcagt ggaacgaaaa 3720
ctcacgttaa gggattttgg tcatgggcgc gcctcatact cctgcaggca tgagattatc 3780
aaaaaggatc ttcacctaga tccttttaaa ttaaaaatga agttttaaat caatctaaag 3840
tatatatgag taaacttggt ctgacagtta ccaatgctta atcagtgagg cacctatctc 3900
agcgatctgt ctatttcgtt catccatagt tgcctgactc cccgtcgtgt agataactac 3960
gatacgggag ggcttaccat ctggccccag tgctgcaatg ataccgcgag acccacgctc 4020
accggctcca gatttatcag caataaacca gccagccgga agggccgagc gcagaagtgg 4080
tcctgcaact ttatccgcct ccatccagtc tattaattgt tgccgggaag ctagagtaag 4140
tagttcgcca gttaatagtt tgcgcaacgt tgttgccatt gctacaggca tcgtggtgtc 4200
acgctcgtcg tttggtatgg cttcattcag ctccggttcc caacgatcaa ggcgagttac 4260
atgatccccc atgttgtgca aaaaagcggt tagctccttc ggtcctccga tcgttgtcag 4320
aagtaagttg gccgcagtgt tatcactcat ggttatggca gcactgcata attctcttac 4380
tgtcatgcca tccgtaagat gcttttctgt gactggtgag tactcaacca agtcattctg 4440
agaatagtgt atgcggcgac cgagttgctc ttgcccggcg tcaatacggg ataataccgc 4500
gccacatagc agaactttaa aagtgctcat cattggaaaa cgttcttcgg ggcgaaaact 4560
ctcaaggatc ttaccgctgt tgagatccag ttcgatgtaa cccactcgtg cacccaactg 4620
atcttcagca tcttttactt tcaccagcgt ttctgggtga gcaaaaacag gaaggcaaaa 4680

```
tgccgcaaaa aagggaataa gggcgacacg gaaatgttga atactcatac tcttcctttt   4740
tcaatattat tgaagcattt atcagggtta ttgtctcatg agcggataca tatttgaatg   4800
tatttagaaa aataaacaaa taggggttcc gcgcacattt ccccgaaaag tgccacctga   4860
cgtcaggtac caagcctagg cctccaaaaa agcctcctca ctacttctgg aatagctcag   4920
aggcagaggc ggcctcggcc tctgcataaa taaaaaaaat tagtcagcca tggggcggag   4980
aatgggcgga actgggcgga gttaggggcg ggatgggcgg agttaggggc gggactatgg   5040
ttgctgacta attgagatgc atgctttgca tacttctgcc tgctggggag cctggggact   5100
ttccacacct ggttgctgac taattgagat gcatgctttg catacttctg cctgctgggg   5160
agcctgggga ctttccacac cggatccacc atggatagat ccggaaagcc tgaactcacc   5220
gcgacgtctg tcgagaagtt tctgatcgaa aagttcgaca gcgtctccga cctgatgcag   5280
ctctcggagg gcgaagaatc tcgtgctttc agcttcgatg taggagggcg tggatatgtc   5340
ctgcgggtaa atagctgcgc cgatggtttc tacaaagatc gttatgttta tcggcacttt   5400
gcatcggccg cgctcccgat tccggaagtg cttgacattg gggagttcag cgagagcctg   5460
acctattgca tctcccgccg tgcacagggt gtcacgttgc aagacctgcc tgaaaccgaa   5520
ctgcccgctg ttctgcagcc ggtcgcggag gccatggatg cgatcgctgc ggccgatctt   5580
agccagacga gcgggttcgg cccattcgga ccgcaaggaa tcggtcaata cactacatgg   5640
cgtgatttca tatgcgcgat tgctgatccc catgtgtatc actggcaaac tgtgatggac   5700
gacaccgtca gtgcgtccgt cgcgcaggct ctcgatgagc tgatgctttg ggccgaggac   5760
tgccccgaag tccggcacct cgtgcacgcg gatttcggct ccaacaatgt cctgacggac   5820
aatggccgca taacagcggt cattgactgg agcgaggcga tgttcgggga ttcccaatac   5880
gaggtcgcca acatcttctt ctggaggccg tggttggctt gtatggagca gcagacgcgc   5940
tacttcgagc ggaggcatcc ggagcttgca ggatcgccgc ggctccgggc gtatatgctc   6000
cgcattggtc ttgaccaact ctatcagagc ttggttgacg gcaatttcga tgatgcagct   6060
tgggcgcagg gtcgatgcga cgcaatcgtc cgatccggag ccgggactgt cgggcgtaca   6120
caaatcgccc gcagaagcgc ggccgtctgg accgatggct gtgtagaagt actcgccgat   6180
agtggaaacc gacgccccag cactcgtccg agggcaaagg aatagacgcg tgctgtaagt   6240
ctgcagaaat tgatgatcta ttaaacaata aagatgtcca ctaaaatgga agtttttcct   6300
gtcatacttt gttaagaagg gtgagaacag agtacctaca ttttgaatgg aaggattgga   6360
gctacggggg tgggggtggg gtgggattag ataaatgcct gctctttact gaaggctctt   6420
tactattgct ttatgataat gtttcatagt tggatatcat aatttaaaca agcaaaacca   6480
aattaagggc cagctcattc ctcccactca tgatctatgg atctatagat ctctcgtgca   6540
gctggggctc tagggggtat ccccacgcgc cctgtagcgg cgcattaagc gcggcgggtg   6600
tggtggttac gcgcagcgtg accgctacac ttgccagcgc cctagcgccc gctcctttcg   6660
ctttcttccc ttcctttctc gccacgttcg ccggctttcc ccgtcaagct ctaaatcggg   6720
ggctcccttt agggttccga tttagtgctt tacggcacct cgaccccaaa aaacttgatt   6780
agggtgatgg ttcacgtagt gggccatcgc cctgatagac ggtttttcgc cctttgacgt   6840
tggagtccac gttctttaat agtggactct tgttccaaac tggaacaaca ctcaacccta   6900
tctcggtcta ttcttttgat ttataaggga ttttgccgat ttcggcctat tggttaaaaa   6960
atgagctgat ttaacaaaaa tttaacgcga attaattctg tggaatgtgt gtcagttag    7019
```

<210> SEQ ID NO 41
<211> LENGTH: 2272
<212> TYPE: DNA
<213> ORGANISM: Artificial
<220> FEATURE:
<223> OTHER INFORMATION: Synthetic construct

<400> SEQUENCE: 41 tagttattaa tagtaatcaa ttacggggtc attagttcat agcccatata tggagttccg 60 cgttacataa cttacggtaa atggcccgcc tggctgaccg cccaacgacc cccgcccatt 120 gacgtcaata atgacgtatg ttcccatagt aacgccaata gggactttcc attgacgtca 180 atgggtggag tatttacggt aaactgccca cttggcagta catcaagtgt atcatatgcc 240 aagtacgccc cctattgacg tcaatgacgg taaatggccc gcctggcatt atgcccagta 300 catgacctta tgggactttc ctacttggca gtacatctac gtattagtca tcgctattac 360 catggtgatg cggttttggc agtacatcaa tgggcgtgga tagcggtttg actcacgggg 420 atttccaagt ctccacccca ttgacgtcaa tgggagtttg ttttggcacc aaaatcaacg 480 ggactttcca aaatgtcgta acaactccgc cccattgacg caaatgggcg gtaggcgtgt 540 acggtgggag gtctatataa gcagagctca tgatagaagc actctactat tcgtcgaccg 600 atcctgagaa cttcagggtg agtttgggga cccttgattg ttctttcttt ttcgctattg 660 taaaattcat gttatatgga gggggcaaag ttttcagggt gttgtttaga atgggaagat 720 gtcccttgta tcaccatgga ccctcatgat aattttgttt ctttcacttt ctactctgtt 780 gacaaccatt gtctcctctt attttctttt cattttctgt aactttttcg ttaaacttta 840 gcttgcattt gtaacgaatt tttaaattca cttttgttta tttgtcagat tgtaagtact 900 ttctctaatc actttttttt caaggcaatc agggtatatt atattgtact tcagcacagt 960 tttagagaac aattgttata attaaatgat aaggtagaat atttctgcat ataaattctg 1020 gctggcgtgg aaatattctt attggtagaa acaactacac cctggtcatc atcctgcctt 1080 tctctttatg gttacaatga tatacactgt ttgagatgag gataaaatac tctgagtcca 1140 aaccgggccc ctctgctaac catgttcatg ccttcttctc tttcctacag ctcctgggca 1200 acgtgctggt tgttgtgctg tctcatcatt ttggcaaaga attaagctta tactcgagct 1260 ctagattggg aacccgggtc tctcgaattc gagatctcca ccatgcacag acctagacgt 1320 cgtggaactc gtccacctcc actggcactg ctcgctgctc tcctcctggc tgcacgtggt 1380 gctgatgcag acatccagat gacccagtct ccatcctccc tgtctgcatc tgtaggagac 1440 agagtcacca tcacttgccg ggcgagtcag ggcattagcg attatttagc ctggtatcag 1500 cagaaaccag ggaaagttcc taacctcctg atctatgctg cgtccgcttt acaatcaggg 1560 gtcccatctc gtttcagtgg cagtggatct gggacagatt tcactctcac catcagcagc 1620 ctgcagcctg aggatgttgc aacttattac tgtcaaaatt ataacactgc cccgctcact 1680 ttcggcgggg ggaccaaggt ggaaatcaaa cgaactgtgg ctgcaccatc tgtcttcatc 1740 ttcccgccat ctgatgagca gttgaaatct ggaactgcct ctgttgtgtg cctgctgaat 1800 aacttctatc ccagagaggc caaagtacag tggaaggtgg ataacgccct ccaatcgggt 1860 aactcccagg agagtgtcac agagcaggac agcaaggaca gcacctacag cctcagcagc 1920 accctgacgc tgagcaaagc agactacgag aaacacaaag tctacgcctg cgaagtcacc 1980 catcagggcc tgagctcgcc cgtcacaaag agcttcaaca ggggagagtg ttaggcggcc 2040 gctaatcagc cataccacat ttgtagaggt tttacttgct ttaaaaaacc tcccacacct 2100

```
ccccctgaac ctgaaacata aaatgaatgc aattgttgtt gttaacttgt ttattgcagc   2160

ttataatggt tacaaataaa gcaatagcat cacaaatttc acaaataaag catttttttc   2220

actgcattct agttgtggtt tgtccaaact catcaatgta tcttatcatg tc           2272


<210> SEQ ID NO 42
<211> LENGTH: 6335
<212> TYPE: DNA
<213> ORGANISM: Artificial
<220> FEATURE:
<223> OTHER INFORMATION: Synthetic plasmid

<400> SEQUENCE: 42

tcgagctcta gattgggaac ccgggtctct cgaattcgag atctccacca tgcacagacc     60

tagacgtcgt ggaactcgtc cacctccact ggcactgctc gctgctctcc tcctggctgc    120

acgtggtgct gatgcagaca tccagatgac ccagtctcca tcctccctgt ctgcatctgt    180

aggagacaga gtcaccatca cttgccgggc gagtcagggc attagcgatt atttagcctg    240

gtatcagcag aaaccaggga aagttcctaa cctcctgatc tatgctgcgt ccgctttaca    300

atcaggggtc ccatctcgtt tcagtggcag tggatctggg acagatttca ctctcaccat    360

cagcagcctg cagcctgagg atgttgcaac ttattactgt caaaattata acactgcccc    420

gctcactttc ggcgggggga ccaaggtgga aatcaaacga actgtggctg caccatctgt    480

cttcatcttc ccgccatctg atgagcagtt gaaatctgga actgcctctg ttgtgtgcct    540

gctgaataac ttctatccca gagaggccaa agtacagtgg aaggtggata acgccctcca    600

atcgggtaac tcccaggaga gtgtcacaga gcaggacagc aaggacagca cctacagcct    660

cagcagcacc ctgacgctga gcaaagcaga ctacgagaaa cacaaagtct acgcctgcga    720

agtcacccat cagggcctga gctcgcccgt cacaaagagc ttcaacaggg gagagtgtta    780

ggcggccgct aatcagccat accacatttg tagaggtttt acttgcttta aaaaacctcc    840

cacacctccc cctgaacctg aaacataaaa tgaatgcaat tgttgttgtt aacttgttta    900

ttgcagctta taatggttac aaataaagca atagcatcac aaatttcaca aataaagcat    960

ttttttcact gcattctagt tgtggtttgt ccaaactcat caatgtatct tatcatgtct   1020

accggtaggg cccctctctt catgtgagca aaaggccagc aaaaggccag gaaccgtaaa   1080

aaggccgcgt tgctggcgtt tttccatagg ctccgccccc ctgacgagca tcacaaaaat   1140

cgacgctcaa gtcagaggtg gcgaaacccg acaggactat aaagatacca ggcgtttccc   1200

cctggaagct ccctcgtgcg ctctcctgtt ccgaccctgc cgcttaccgg atacctgtcc   1260

gcctttctcc cttcgggaag cgtggcgctt tctcaatgct cacgctgtag gtatctcagt   1320

tcggtgtagg tcgttcgctc caagctgggc tgtgtgcacg aaccccccgt tcagcccgac   1380

cgctgcgcct tatccggtaa ctatcgtctt gagtccaacc cggtaagaca cgacttatcg   1440

ccactggcag cagccactgg taacaggatt agcagagcga ggtatgtagg cggtgctaca   1500

gagttcttga agtggtggcc taactacggc tacactagaa ggacagtatt tggtatctgc   1560

gctctgctga agccagttac cttcggaaaa agagttggta gctcttgatc cggcaaacaa   1620

accaccgctg gtagcggtgg tttttttgtt tgcaagcagc agattacgcg cagaaaaaaa   1680

ggatctcaag aagatccttt gatcttttct acggggtctg acgctcagtg gaacgaaaac   1740

tcacgttaag ggattttggt catgggcgcg ggcatgagat tatcaaaaag gatcttcacc   1800

tagatccttt taaattaaaa atgaagtttt aaatcaatct aaagtatata tgagtaaact   1860

tggtctgaca gttaccaatg cttaatcagt gaggcaccta tctcagcgat ctgtctattt   1920
```

```
cgttcatcca tagttgcctg actccccgtc gtgtagataa ctacgatacg ggagggctta   1980
ccatctggcc ccagtgctgc aatgataccg cgagacccac gctcaccggc tccagattta   2040
tcagcaataa accagccagc cggaagggcc gagcgcagaa gtggtcctgc aactttatcc   2100
gcctccatcc agtctattaa ttgttgccgg gaagctagag taagtagttc gccagttaat   2160
agtttgcgca acgttgttgc cattgctaca ggcatcgtgg tgtcacgctc gtcgtttggt   2220
atggcttcat tcagctccgg ttcccaacga tcaaggcgag ttacatgatc ccccatgttg   2280
tgcaaaaaag cggttagctc cttcggtcct ccgatcgttg tcagaagtaa gttggccgca   2340
gtgttatcac tcatggttat ggcagcactg cataattctc ttactgtcat gccatccgta   2400
agatgctttt ctgtgactgg tgagtactca accaagtcat tctgagaata gtgtatgcgg   2460
cgaccgagtt gctcttgccc ggcgtcaata cgggataata ccgcgccaca tagcagaact   2520
ttaaaagtgc tcatcattgg aaaacgttct tcggggcgaa aactctcaag gatcttaccg   2580
ctgttgagat ccagttcgat gtaacccact cgtgcaccca actgatcttc agcatctttt   2640
actttcacca gcgtttctgg gtgagcaaaa acaggaaggc aaaatgccgc aaaaaaggga   2700
ataagggcga cacggaaatg ttgaatactc atactcttcc tttttcaata ttattgaagc   2760
atttatcagg gttattgtct catgagcgga tacatatttg aatgtattta gaaaaataaa   2820
caaatagggg ttccgcgcac atttccccga aaagtgccac ctgacgtcag gtacacttag   2880
gcgcgccatt agagttcctg caggctacat ggtaccaagc ctaggcctcc aaaaaagcct   2940
cctcactact tctggaatag ctcagaggca gaggcggcct cggcctctgc ataaataaaa   3000
aaaattagtc agccatgggg cggagaatgg gcggaactgg gcggagttag gggcgggatg   3060
ggcggagtta ggggcgggac tatggttgct gactaattga gatgcatgct ttgcatactt   3120
ctgcctgctg gggagcctgg ggactttcca cacctggttg ctgactaatt gagatgcatg   3180
ctttgcatac ttctgcctgc tggggagcct ggggactttc cacaccggat ccaccatgga   3240
tagatccgga aagcctgaac tcaccgcgac gtctgtcgag aagtttctga tcgaaaagtt   3300
cgacagcgtc tccgacctga tgcagctctc ggagggcgaa gaatctcgtg ctttcagctt   3360
cgatgtagga gggcgtggat atgtcctgcg ggtaaatagc tgcgccgatg gtttctacaa   3420
agatcgttat gtttatcggc actttgcatc ggccgcgctc ccgattccgg aagtgcttga   3480
cattggggag ttcagcgaga gcctgaccta ttgcatctcc cgccgtgcac agggtgtcac   3540
gttgcaagac ctgcctgaaa ccgaactgcc cgctgttctg cagccggtcg cggaggccat   3600
ggatgcgatc gctgcggccg atcttagcca gacgagcggg ttcggcccat tcggaccgca   3660
aggaatcggt caatacacta catggcgtga tttcatatgc gcgattgctg atccccatgt   3720
gtatcactgg caaactgtga tggacgacac cgtcagtgcg tccgtcgcgc aggctctcga   3780
tgagctgatg ctttgggccg aggactgccc cgaagtccgg cacctcgtgc acgcggattt   3840
cggctccaac aatgtcctga cggacaatgg ccgcataaca gcggtcattg actggagcga   3900
ggcgatgttc ggggattccc aatacgaggt cgccaacatc ttcttctgga ggccgtggtt   3960
ggcttgtatg gagcagcaga cgcgctactt cgagcggagg catccggagc ttgcaggatc   4020
gccgcggctc cgggcgtata tgctccgcat tggtcttgac caactctatc agagcttggt   4080
tgacggcaat ttcgatgatg cagcttgggc gcagggtcga tgcgacgcaa tcgtccgatc   4140
cggagccggg actgtcgggc gtacacaaat cgcccgcaga agcgcggccg tctggaccga   4200
tggctgtgta gaagtactcg ccgatagtgg aaaccgacgc cccagcactc gtccgagggc   4260
```

```
aaaggaatag acgcgtgctg taagtctgca gaaattgatg atctattaaa caataaagat   4320
gtccactaaa atggaagttt ttcctgtcat actttgttaa gaagggtgag aacagagtac   4380
ctacattttg aatggaagga ttggagctac gggggtgggg gtggggtggg attagataaa   4440
tgcctgctct ttactgaagg ctctttacta ttgctttatg ataatgtttc atagttggat   4500
atcataattt aaacaagcaa aaccaaatta agggccagct cattcctccc actcatgatc   4560
tatggatcta tagatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcgggggctc cctttagggt tccgatttag tgctttacgg   4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga cccccgccca ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc cccctattga   5340
cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg gatagcggtt tgactcacgg ggatttccaa gtctccaccc   5520
cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
aagcagagct catgatagaa gcactctact attcgtcgac cgatcctgag aacttcaggg   5700
tgagtttggg gacccttgat tgttctttct ttttcgctat tgtaaaattc atgttatatg   5760
gagggggcaa agttttcagg gtgttgttta gaatgggaag atgtcccttg tatcaccatg   5820
gaccctcatg ataattttgt ttctttcact ttctactctg ttgacaacca ttgtctcctc   5880
ttattttctt ttcattttct gtaacttttt cgttaaactt tagcttgcat ttgtaacgaa   5940
tttttaaatt cacttttgtt tatttgtcag attgtaagta ctttctctaa tcactttttt   6000
ttcaaggcaa tcagggtata ttatattgta cttcagcaca gttttagaga acaattgtta   6060
taattaaatg ataaggtaga atatttctgc atataaattc tggctggcgt ggaaatattc   6120
ttattggtag aaacaactac accctggtca tcatcctgcc tttctcttta tggttacaat   6180
gatatacact gtttgagatg aggataaaat actctgagtc caaaccgggc ccctctgcta   6240
accatgttca tgccttcttc tctttcctac agctcctggg caacgtgctg gttgttgtgc   6300
tgtctcatca ttttggcaaa gaattaagct tatac                              6335
```

<210> SEQ ID NO 43
<211> LENGTH: 115
<212> TYPE: PRT
<213> ORGANISM: Artificial
<220> FEATURE:
<223> OTHER INFORMATION: consensus sequence
<220> FEATURE:
<221> NAME/KEY: MISC_FEATURE <222> LOCATION: (1)..(1)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: Xaa can be any naturally occurring amino acid
<220> FEATURE:
<221> NAME/KEY: MISC_FEATURE
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (111)..(111)
<220> FEATURE:
<221> NAME/KEY: MISC_FEATURE
<222> LOCATION: (114)..(114)
<223> OTHER INFORMATION: Xaa can be any naturally occurring amino acid

<400> SEQUENCE: 43

Xaa Asp Val Trp Gly Gln Gly Thr Thr Val Xaa Val Ser Ser Ala Ser
1 5 10 15

Thr Lys Gly Pro Ser Val Phe Pro Leu Ala Pro Xaa Ser Xaa Ser Thr
20 25 30

Ser Xaa Xaa Thr Ala Ala Leu Gly Cys Leu Val Lys Asp Tyr Phe Pro
35 40 45

Glu Pro Val Thr Val Ser Trp Asn Ser Gly Ala Leu Thr Ser Gly Val
50 55 60

His Thr Phe Pro Ala Val Leu Gln Ser Ser Gly Leu Tyr Ser Leu Ser
65 70 75 80

Ser Val Val Thr Val Pro Ser Ser Ser Leu Gly Thr Xaa Thr Tyr Xaa
85 90 95

Cys Asn Val Xaa His Lys Pro Ser Asn Thr Lys Val Asp Lys Xaa Val
100 105 110

Glu Xaa Lys
115

<210> SEQ ID NO 44
<211> LENGTH: 225
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Xaa can be any naturally occurring amino acid <220> FEATURE:
<221> NAME/KEY: MISC_FEATURE
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (75)..(75)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be any naturally occurring amino acid
<220> FEATURE:
<221> NAME/KEY: MISC_FEATURE
<222> LOCATION: (109)..(110)
<223> OTHER INFORMATION: Xaa can be any naturally occurring amino acid
<220> FEATURE:
<221> NAME/KEY: MISC_FEATURE
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: Xaa can be any naturally occurring amino acid
<220> FEATURE:
<221> NAME/KEY: MISC_FEATURE
<222> LOCATION: (198)..(198)
<223> OTHER INFORMATION: Xaa can be any naturally occurring amino acid
<220> FEATURE:
<221> NAME/KEY: MISC_FEATURE
<222> LOCATION: (224)..(224)
<223> OTHER INFORMATION: Xaa can be any naturally occurring amino acid

<400> SEQUENCE: 44

```
Tyr Gly Pro Pro Cys Pro Pro Cys Pro Ala Pro Glu Xaa Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser Xaa Glu
        35                  40                  45

Asp Pro Glu Val Xaa Phe Asn Trp Tyr Val Asp Gly Val Glu Val His
    50                  55                  60

Asn Ala Lys Thr Lys Pro Arg Glu Glu Gln Xaa Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Xaa Leu Pro Xaa Xaa Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Xaa Xaa Glu Xaa Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Xaa Leu Thr Val Asp
            180                 185                 190

Lys Ser Arg Trp Gln Xaa Gly Asn Val Phe Ser Cys Ser Val Met His
        195                 200                 205

Glu Ala Leu His Asn His Tyr Thr Gln Lys Ser Leu Ser Leu Ser Xaa
```

```
    210                 215                 220

Gly
225


<210> SEQ ID NO 45
<211> LENGTH: 60
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (21)..(22)
<223> OTHER INFORMATION: Xaa can be any naturally occurring amino acid
<220> FEATURE:
<221> NAME/KEY: MISC_FEATURE
<222> LOCATION: (24)..(27)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: Xaa can be any naturally occurring amino acid
<220> FEATURE:
<221> NAME/KEY: MISC_FEATURE
<222> LOCATION: (56)..(56)
<223> OTHER INFORMATION: Xaa can be any naturally occurring amino acid

<400> SEQUENCE: 45

Ser Asp Tyr Leu Ala Trp Tyr Gln Gln Lys Pro Gly Xaa Xaa Pro Xaa
1               5                   10                  15

Leu Leu Ile Tyr Xaa Xaa Ser Xaa Xaa Xaa Xaa Gly Val Pro Xaa Arg
            20                  25                  30

Phe Xaa Gly Ser Gly Ser Gly Thr Asp Phe Thr Leu Thr Ile Ser Xaa
        35                  40                  45

Leu Xaa Pro Glu Asp Xaa Ala Xaa Tyr Tyr Cys Gln
    50                  55                  60


<210> SEQ ID NO 46
<211> LENGTH: 118
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa can be any naturally occurring amino acid
```

-continued

```
<400> SEQUENCE: 46

Thr Phe Gly Xaa Gly Thr Lys Val Glu Ile Lys Arg Thr Val Ala Ala
1               5                   10                  15

Pro Ser Val Phe Ile Phe Pro Pro Ser Asp Glu Gln Leu Lys Ser Gly
            20                  25                  30

Thr Ala Ser Val Val Cys Leu Leu Asn Asn Phe Tyr Pro Arg Glu Ala
        35                  40                  45

Lys Val Gln Trp Lys Val Asp Asn Ala Leu Gln Ser Gly Asn Ser Gln
    50                  55                  60

Glu Ser Val Thr Glu Gln Asp Ser Lys Asp Ser Thr Tyr Ser Leu Ser
65                  70                  75                  80

Ser Thr Leu Thr Leu Ser Lys Ala Asp Tyr Glu Lys His Lys Val Tyr
                85                  90                  95

Ala Cys Glu Val Thr His Gln Gly Leu Ser Ser Pro Val Thr Lys Ser
            100                 105                 110

Phe Asn Arg Gly Glu Cys
        115
```

What is claimed:

1. An isolated polynucleotide comprising a nucleotide sequence, which encodes an endoplasmic reticulum degradation-enhancing alpha-mannosidase-like protein 2 (EDEM2), a promoter, and a multi-subunit protein, wherein the EDEM2 comprises an amino acid sequence that is at least 92% identical to SEQ ID NO: 1, and wherein the multi-subunit protein comprises at least one *antibody* heavy chain [antibody and] *or* at least one *antibody* light chain [antibody].

2. The isolated polynucleotide of claim 1, wherein the promoter is selected from the group consisting of ubiquitin C, CMV-IE and SV40.

3. The isolated polynucleotide of claim 2, wherein the EDEM2 comprises the amino acid sequence of SEQ ID NO: 8.

4. The isolated polynucleotide of claim 2, wherein the EDEM2 consists essentially of the amino acid sequence of SEQ ID NO: 8.

5. The isolated polynucleotide of claim 2, wherein the EDEM2 comprises the amino acid sequence selected from the group consisting of SEQ ID NO: 1, SEQ ID NO: 2, SEQ ID NO: 3, SEQ ID NO: 4, SEQ ID NO: 5, *and* SEQ ID NO: 6 [and SEQ ID NO: 7].

6. The isolated polynucleotide of claim 2, wherein the EDEM2 consists essentially of the amino acid sequence of SEQ ID NO: 1.

7. The isolated polynucleotide of claim 1, wherein the [nucleotide sequence further] *multi-subunit protein* comprises at least one antibody heavy chain [or] *and* at least one antibody light chain.

8. The isolated polynucleotide of claim 7, wherein the nucleotide sequence encodes the heavy chain comprising amino acid sequences SEQ ID NO: 43 and SEQ ID NO: 44 and the light chain comprising amino acid sequences SEQ ID NO: 45 and SEQ ID NO: 46.

9. The isolated polynucleotide of claim 7, where the nucleotide sequence encodes an anti-GDF8 antibody heavy chain, operably linked to a mammalian ubiquitin C promoter or a human CMV-IE promoter.

10. The isolated polynucleotide of claim 9, wherein the anti-GDF8 antibody heavy chain comprises the amino acid sequence of SEQ ID NO: 20.

11. The isolated polynucleotide of claim 9, wherein the anti-GDF8 antibody heavy chain comprises the amino acid sequence of SEQ ID NO: 19.

12. The isolated polynucleotide of claim 9 comprising the nucleotide sequence of SEQ ID NO: 23.

13. The isolated polynucleotide of claim 9 comprising the nucleotide sequence of SEQ ID NO: 24.

14. The isolated polynucleotide of claim 7, wherein the nucleotide sequence encodes an anti-GDF8 antibody light chain, operably linked to a mammalian ubiquitin C promoter or a human CMV-IE promoter.

15. The isolated polynucleotide of claim 14, wherein the anti-GDF8 antibody light chain comprises the amino acid sequence of SEQ ID NO: 22.

16. The isolated polynucleotide of claim 14, wherein the anti-GDF8 antibody light chain comprises the amino acid sequence of SEQ ID NO: 21.

17. The isolated polynucleotide of claim 14 comprising the nucleotide sequence of SEQ ID NO: 25.

18. The isolated polynucleotide claim 14 comprising the nucleotide sequence of SEQ ID NO: 26.

19. The isolated polynucleotide of claim 7, wherein the nucleotide sequence encodes an anti-ANG2 antibody heavy chain, operably linked to a mammalian ubiquitin C promoter or a human CMV-IE promoter.

20. The isolated polynucleotide of claim 19, wherein the anti-ANG2 antibody heavy chain comprises the amino acid sequence of SEQ ID NO: 28.

21. The isolated polynucleotide of claim 19, wherein the anti-ANG2 antibody heavy chain comprises the amino acid sequence of SEQ ID NO: 27.

22. The isolated polynucleotide of claim 19 comprising the nucleotide sequence of SEQ ID NO: 31.

23. The isolated polynucleotide of claim 19 comprising the nucleotide sequence of SEQ ID NO: 32.

24. The isolated polynucleotide of claim 7, wherein the nucleotide sequence encodes an anti-ANG2 antibody light chain, operably linked to a promoter.

25. The isolated polynucleotide of claim 24, wherein the anti-ANG2 antibody light chain comprises the amino acid sequence of SEQ ID NO: 30.

26. The isolated polynucleotide of claim 24, wherein the anti-ANG2 antibody light chain comprises the amino acid sequence of SEQ ID NO: 29.

27. The isolated polynucleotide of claim 24 comprising the nucleotide sequence of SEQ ID NO: 33.

28. The isolated polynucleotide of claim 24 comprising the nucleotide sequence of SEQ ID NO: 34.

29. The isolated polynucleotide of claim 7, wherein the nucleotide sequence encodes an anti-AngPtl4 antibody heavy chain, operably linked to a mammalian ubiquitin C promoter or a human CMV-IE promoter.

30. The isolated polynucleotide of claim 29, wherein the anti-AngPtl4 antibody heavy chain comprises the amino acid sequence of SEQ ID NO: 36.

31. The isolated polynucleotide of claim 29, wherein the anti-AngPtl4 antibody heavy chain comprises the amino acid sequence of SEQ ID NO: 35.

32. The isolated polynucleotide of claim 29 comprising the nucleotide sequence of SEQ ID NO: 39.

33. The isolated polynucleotide of claim 29 comprising the nucleotide sequence of SEQ ID NO: 40.

34. The isolated polynucleotide of claim 7, wherein the nucleotide sequence encodes an anti-AngPtl4 antibody light chain, operably linked to a mammalian ubiquitin C promoter or a human CMV-IE promoter.

35. The isolated polynucleotide of claim 34, wherein the anti-AngPtl4 antibody light chain comprises the amino acid sequence of SEQ ID NO: 38.

36. The isolated polynucleotide of claim 34, wherein the anti-AngPtl4 antibody light chain comprises the amino acid sequence of SEQ ID NO: 37.

37. The isolated polynucleotide of claim 34 comprising the nucleotide sequence of SEQ ID NO: 41.

38. The isolated polynucleotide of claim 34 comprising the nucleotide sequence of SEQ ID NO: 42.

* * * * *